(12) United States Patent
Shoseyov et al.

(10) Patent No.: US 9,687,583 B2
(45) Date of Patent: Jun. 27, 2017

(54) ADHESIVE BIOPOLYMERS AND USES THEREOF

(75) Inventors: Oded Shoseyov, Karmei Yosef (IL); Shaul Lapidot, Kibbutz Tzora (IL); Amit Rivkin, Beer-Yaacov (IL)

(73) Assignees: Yissum Research Development Company of the Hebrew University of Jerusalem Ltd., Jerusalem (IL); CollPlant Ltd., Ness Ziona (IL)

( * ) Notice: Subject to any disclaimer, the term of this patent is extended or adjusted under 35 U.S.C. 154(b) by 0 days.

(21) Appl. No.: 14/342,392

(22) PCT Filed: Aug. 30, 2012

(86) PCT No.: PCT/IL2012/050340
§ 371 (c)(1),
(2), (4) Date: Mar. 3, 2014

(87) PCT Pub. No.: WO2013/030840
PCT Pub. Date: Mar. 7, 2013

(65) Prior Publication Data
US 2014/0371131 A1 Dec. 18, 2014

Related U.S. Application Data

(60) Provisional application No. 61/530,167, filed on Sep. 1, 2011.

(51) Int. Cl.
*A61L 24/10* (2006.01)
*C08J 3/24* (2006.01)
*C09J 189/00* (2006.01)
*C08B 37/00* (2006.01)
*C08H 1/00* (2006.01)
*C07K 14/435* (2006.01)

(52) U.S. Cl.
CPC ...... *A61L 24/108* (2013.01); *C07K 14/43563* (2013.01); *C08B 37/00* (2013.01); *C08H 1/00* (2013.01); *C08J 3/24* (2013.01); *C09J 189/00* (2013.01); *A61L 2430/06* (2013.01); *C08J 2300/16* (2013.01)

(58) Field of Classification Search
None
See application file for complete search history.

(56) References Cited

U.S. PATENT DOCUMENTS

| | | | |
|---|---|---|---|
| 6,982,298 | B2 | 1/2006 | Calabro et al. |
| 8,431,158 | B2 * | 4/2013 | Shoseyov et al. ......... 424/484 |
| 2002/0111694 | A1 * | 8/2002 | Ellingsen et al. ......... 623/23.57 |
| 2004/0234609 | A1 | 11/2004 | Collier et al. |
| 2007/0099231 | A1 | 5/2007 | Elvin |
| 2007/0275408 | A1 | 11/2007 | Elvin |
| 2011/0269826 | A1 * | 11/2011 | Kingsman et al. ......... 514/44 R |
| 2013/0225793 | A1 | 8/2013 | Shoseyov et al. |
| 2014/0256641 | A1 | 9/2014 | Shoseyov et al. |
| 2015/0094452 | A1 | 4/2015 | Shoseyov et al. |
| 2016/0145311 | A1 | 5/2016 | Shoseyov et al. |

FOREIGN PATENT DOCUMENTS

| | | |
|---|---|---|
| CN | 1390937 | 1/2003 |
| JP | 2000-503206 | 3/2000 |
| JP | 2004-504803 | 2/2004 |
| JP | 2007-507495 | 3/2007 |
| JP | 2007-531506 | 11/2007 |
| WO | WO 97/26358 | 7/1997 |
| WO | WO 01/34091 | 5/2001 |
| WO | WO 01/44401 | 6/2001 |
| WO | WO 2004/063388 | 7/2004 |
| WO | WO 2004/104020 | 12/2004 |
| WO | WO 2004/104042 | 12/2004 |
| WO | WO 2004/104043 | 12/2004 |
| WO | WO 2006/035442 | 4/2006 |
| WO | WO 2007/020449 | 2/2007 |
| WO | WO 2009/069123 | 6/2009 |
| WO | WO 2013/030840 | 3/2013 |

OTHER PUBLICATIONS

Tamburro AM, et al Molecular and supramolecular structural studies on significant repetitive sequences of resilin, Chembiochem. Jan. 4, 2010;11(1):83-93.*
Technical Brief 2009 vol. 8 Particle Sciences (two pages).*
Communication Pursuant to Article 94(3) EPC Dated Dec. 3, 2010 From the European Patent Office Re. Application No. 08853290.8.
Communication Pursuant to Article 94(3) EPC Dated Feb. 6, 2013 From the European Patent Office Re. Application No. 08853290.8.
Communication Pursuant to Rules 70(2) and 70a(2) EPC and Reference to Rule 39(1) EPC Dated Jun. 10, 2013 From the European Patent Office Re. Application No. 12196826.7.
Communication Relating to the Results of the Partial International Search Dated Mar. 15, 2013 From the International Searching Authority Re. Application No. PCT/IL2012/050340.

(Continued)

*Primary Examiner* — Thomas S Heard

(57) ABSTRACT

Provided herein are polymers having the general formula I as defined herein,

A-L-B                                    Formula I as well as crosslinked polymers having the general formula III:

B'-L'-A'-A"-L"-B"                        Formula III and methods of preparing the polymers, wherein A is a dihydroxyphenyl moiety; A'-A" is a pair of crosslinked dihydroxyphenyl moieties; B, B' and B" are each a biopolymer; and L, L' and L" are each a linking moiety. Further provided are crosslinked adhesives prepared from the polymers, methods of generating same by oxidizing a polymer, and uses thereof. Further provided are kits comprising an adhesive and an oxidizing agent.

22 Claims, 15 Drawing Sheets
(8 of 15 Drawing Sheet(s) Filed in Color)

(56) References Cited

OTHER PUBLICATIONS

Communication Relating to the Results of the Partial International Search Dated Apr. 21, 2009 From the International Searching Authority Re.: Application No. PCT/IL2008/001542.
Communications Pursuant to Article 94(3) EPC Dated Oct. 21, 2013 From the European Patent Office Re. Application No. 08853290.8.
Corrected Notice of Allowability Dated Jan. 17, 2013 From the US Patent and Trademark Office Re. U.S. Appl. No. 12/744,703.
European Search Report and the European Search Opinion Dated May 8, 2013 From the European Patent Office Re. Application No. 12196826.7.
International Search Report and the Written Opinion Dated Nov. 5, 2009 From the International Searching Authority Re.: Application No. PCT/IL2008/001542.
International Search Report and the Written Opinion Dated May 24, 2013 From the International Searching Authority Re. Application No. PCT/IL2012/050340.
Notice of Allowance Dated Oct. 4, 2013 From the US Patent and Trademark Office Re. U.S. Appl. No. 13/870,032.
Notice of Allowance Dated Dec. 17, 2012 From the US Patent and Trademark Office Re. U.S. Appl. No. 12/744,703.
Notification of European Publication Number and Information on the Application of Article 67(3) EPC Dated May 8, 2013 From the European Patent Office Re. Application No. 12196826.7.
Office Action Dated Oct. 2, 2013 From the Israel Patent Office Re. Application No. 206004 and Its Translation Into English.
Office Action Dated Dec. 28, 2011 From the Israel Patent Office Re. Application No. 206004 and Its Translation Into English.
Official Action Dated Aug. 24, 2012 From the US Patent and Trademark Office Re. U.S. Appl. No. 12/744,703.
Patent Examination Report Dated Dec. 19, 2012 From the Australian Government, IP Australia Re. Application No. 2008331099.
Response Dated Mar. 27, 2011 to Communication Pursuant to Article 94(3) EPC of Dec. 3, 2010 From the European Patent Office Re. Application No. 08853290.8.
Restriction Official Action Dated Dec. 21, 2011 From the US Patent and Trademark Office Re. U.S. Appl. No. 12/744,703.
Restriction Official Action Dated Feb. 28, 2012 From the US Patent and Trademark Office Re. U.S. Appl. No. 12/744,703.
Restriction Official Action Dated Jul. 29, 2013 From the US Patent and Trademark Office Re. U.S. Appl. No. 13/870,032.
Restriction Official Action Dated May 30, 2012 From the US Patent and Trademark Office Re. U.S. Appl. No. 12/744,703.
Supplemental Notice of Allowability Dated Jan. 7, 2014 From the US Patent and Trademark Office Re. U.S. Appl. No. 13/870,032.
Translation of Notice of Reason for Rejection Dated Jul. 19, 2013 From the Japanese Patent Office Re. Application No. 2010-535508.
Aaron et al. "Elastin as a Random-Network Elastomer: A Mechanical and Optical Analysis of Single Elastin Fibers", Biopolymers, 20: 1247-1260, 1981.
Abo et al. "Peptide Sequences for Sucrose Splitting and Glucan Binding Within *Streptococcus sobrinus* Glucosyltransferase (Water-Insoluble Glucan Synthetase)", Journal of Bacteriology, 173(3): 989-996, Feb. 1991.
Adams et al. "RecName: Full=Pro-Resilin; Flags: Precursor; *Drosophila melanogaster* (Fruit Fly)", Database UniProt [Online], XP002519331, Retrieved From EBI Accession No. UNIPROT:Q9V7U0, Database Accession No. Q9V7U0, May 1, 2000.
Adams et al. "The Genome Sequence of *Drosophila melanogaster*", Science, XP000961051, 287(5461): 2185-2195, Mar. 24, 2000. p. 2185-2195.
Ali et al. "Metal Catalyzed Oxidation of Tyrosine Residues by Different Oxidation Systems of Copper/Hydrogen Peroxide", Journal of Inorganic Biochemistry, 98: 173-184, 2004.
Alper "Stretching the Limits. Stretchy Proteins Perform a Variety of Critical Functions for Many Organisms. Researchers Are Now Finding out How They Work and Are Beinning to Apply That Knowledge to New Products", Science, 297: 329-330, Jul. 19, 2002.
Andersen "The Cross-Links in Resilin Identified as Dityrosine and Trityrosine", Biochimica et Biophysica Acta, 93: 213-215, 1964.
Ardell et al. "Tentative Identification of a Resilin Gene in *Drosophila melanogaster*", Insect Biochemistry and Molecular Biology, XP002998361, 31(10): 965-970, Sep. 1, 2001. p. 965-970.
Barroso et al. "Nucleotide Sequence of Clostridium Difficile Toxin B Gene", Nucleic Acids Research, 18(13): 4004, May 25, 1990. EMBL Accession No. X53138.
Beerhues et al. "Primary Structure and Expression of mRNAs Encoding Basic Chitinase and 1,3-Beta-Glucanase in Potato", Plant Molecular Biology, 24: 353-367, 1994.
Belshaw et al. "Specificity of the Binding Domain of Glucoamylase 1", European Journal of Biochemistry, 211: 717-724, 1993.
Bitter et al. "Expression and Secretion Vectors for Yeast", Methods in Enzymology, 153(Art.33): 516-544, 1987.
Bochicchio et al. "Investigating by CD the Molecular Mechanism of Elasticity of Elastomeric Proteins", Chirality, 20: 985-994, 2008.
Booth et al. "The Use of A 'Universal' Yeast Expression Vector to Produce An Antigenic Protein of Mycobacterium Leprae", Immunology Letters, 19: 65-70, 1988.
Boraston et al. "Carbohydrate-Binding Modules: Fine-Tuning Polysaccharide Recognition", Biochemical Journal, 382: 769-781, 2004.
Brisson et al. "Expression of a Bacterial Gene in Plants by Using a Viral Vector", Nature, 310: 511-514, Aug. 9, 1984.
Broekaert et al. "Antimicrobial Peptides From Amaranthus Caudatus Seeds With Sequence Homology to the Cysteine/Glycine-Rich Domain of Chitin-Binding Proteins", Biochemistry, 31: 4308-4314, 1992.
Broekaert et al. "Wound-Induced Accumulation of mRNA Containing a Hevein Sequence in Laticifers of Rubber Tree (Hevea Brasiliensis)", Proc. Natl. Acad. Sci. USA, 87: 7633-7637, Oct. 1990.
Broglie et al. "Ethylene-Regulated Gene Expression: Molecular Cloning of the Genes Encoding an Endochitinase From Phaseolus Vulgaris", Proc. Natl. acad. Sci. USA, 83: 6820-6824, Sep. 1986.
Broglie et al. "Functional Analysis of DNA Sequences Responsible for Ethylene Regulation of a Bean Chitinase Gene in Transgenic Tobacco", The Plant Cell, 1: 599-607, Jun. 1989.
Broglie et al. "Light-Regulated Expression of a Pea Ribulose-1,5-Bisphosphate Carboxylase Small Subunit Gene in Transformed Plant Cells", Science, 224: 838-843, May 25, 1984.
Charati et al. "Hydrophilic Elastomeric Biomaterials Based on Resilin-Like Polypeptides", Soft Matter, 5(18): 3412-3416, 2009.
Chen et al. "Isolation and Characterization of a Novel Chitosan-Binding Protein From Non-Headling Chinese Cabbage Leaves", Journal of Integrative Plant Biology, 47(4): 452-456, 2005.
Clarke et al. "Wound-Induced and Developmental Activation of a Poplar Tree Chitinase Gene Promoter in Transgenic Tobacco", Plant Molecular Biology, 25: 799-815, 1994.
Coles "Studies on Resilin Biosynthesis", Journal of Insect Physiology, 12: 679-691, 1966.
Coruzzi et al. "Tissue-Specific and Light-Regulated Expression of a Pea Nuclear Gene Encoding the Small Subunit of Ribulose-1,5-Bisphosphate Carboxylase", The EMBO Journal, 3(8): 1671-1684, 1984.
Davis et al. "Populus Chitinase Genes: Structure, Organization, and Similarity of Translated Sequences to Herbaceous Plant Chitinases", Plant Molecular Biology, 17: 631-639, 1991.
De Block et al. "Expression of Foreign Genes in Regenerated Plants and in Their Progeny", The EMBO Journal, 3(8): 1681-1689, 1984.
Diaz et al. "EJ-1, A Temperate Bacteriophage of *Streptococcus pneumoniae* Eith a Myoviridae Morphotype", Journal of Bacteriology, 174(17): 5516-5525, Sep. 1992.
Dutta et al. "Physical Approaches for Fabrication of Organized Nanostructure of Resilin-Mimeric Elastic Protein Rec1-Resilin", Biomaterials, 30: 4868-4876, 2009.
Duvic et al. "Purification and Characterization of A ?-1,3-Glucan Binding Protein From Plasma of the Crayfish Pacifastacus Leniusculus", the Journal of Biological Chemistry, 265(16): 9327-9332, Jun. 5, 1990.
Elvin et al. "Synthesis and Properties of Crosslinked Recombinant Pro-Resilin", Nature, XP002407576, 437(7061): 999-1002, Oct. 13, 2005. p. 999-1002.

(56) References Cited

OTHER PUBLICATIONS

Fahnestock et al. "Production of Synthetic Spider Daragline Silk Protein in Pichia Pastoris", Applied Microbiology and Biotechnology, 47: 33-39, 1997.
Fahnestock et al. "Synthetic Spider Dragline Silk Proteins and Their Production in *Escherichia coli*", Applied Microbiology and Biotechnology, 47: 23-32, 1997.
Favier et al. "Mechanical Percolation in Cellulose Whisker Nanocomposites", Polymer Engineering and Science, 37(10): 1732-1739, Oct. 1997.
Ferretti et al. "Nucleotide Sequence of a Glucosyltransferase Gene From *Streptococcus sobrinus* MFe28", Journal of Bacteriology, 169(9): 4271-4278, Sep. 1987.
Fromm et al. "Stable Transformation of Maize After Gene Transfer by Electroporation", Nature, 319: 791-793, Feb. 27, 1987.
Fukuda et al. "Specific Inhibition by Cyclodextrins of Raw Starch Digestion by Fungal Glucoamylase", Bioscience, Biotechnology, and Biochemistry, 56(4): 556-559, 1992.
Garcia et al. "Modular Organization of the Lytic Enzymes of *Streptococcus pneumoniae* and Its Bacteriophages", Gene, 86: 81-88, 1990.
Garcia et al. "Molecular Evolution of Lytic Enzymes of *Streptococcus pneumoniae* and Its Bacteriophages", Proc. Natl. Acad. Sci. USA, 85: 914-918, Feb. 1988.
Garcia et al. "Nucleotide Sequence and Expression of the *Pneumococcal autolysin* Gene Fron Its Own Promoter in *Escherichia coli*", Gene, 43: 265-272, 1986.
Gardella et al. "Expression of Human Parathyroid Hormone-(1-84) in *Escherichia coli* as A Factor X-Cleavable Fusion Protein", The Journal of Biological Chemistry, 265(26): 15854-15859, Sep. 15, 1990.
Giffard et al. "Molecular Characterization of a Cluster of at Least Two Glucosyltransferase Genes in *Strptococcus salivarius* ATCC 25975", Journal of General Microbiology, 137: 2577-2593, 1991.
Gilboa et al. "Transfer and Expression of Cloned Genes Using Retroviral Vectors", BioTechniques, 4(6): 504-512, 1986.
Gilkes et al. "Domains in Microbial ?-1,4-Glycanases: Sequence Conservation, Function, and Enzyme Families", Microbiological Reviews, 55(2): 303-315, Jun. 1991.
Gurley et al. "Upstream Sequences Required for Efficient Expression of a Soybean Heat Shock Gene", Molecular and Cellular Biology, 6(2): 559-565, Feb. 1986.
Hamel et al. "Nucleotide Sequence of a Brassica Napus Endochitinase Gene", Plant Physiology, 101: 1403, 1993.
Haynes et al. "Globular Proteins at Solid/Liquid Interfaces", Colloids and Surfaces B: Biointerfaces, 2: 517-566, 1994.
Hedrick et al. "Chitinase cDNA Cloning and mRNA induction by Fungal Elicitor, Wounding, and Infection", Plant Physiology, 86: 182-186, 1988.
Honda et al. "Nucleotide Sequence of the *Streptococcus mutans* GtfD Gene Encoding the Glucosyltransferase-S Enzyme", Journal of General Microbiology, 136: 2099-2105, 1990.
Jespersen et al. "Comparison of the Domain-Level Organization of Starch Hydrolases and Related Enzymes", Biochemical Journal, 280: 51-55, 1991.
Jones et al. "Isolation and Characterization of Genes Encoding Two Chitinase Enzymes From Serratia Marcescens", The EMBO Journal, 5(3): 467-473, 1986.
Kato et al. "The Hydrogen Peroxide/Copper Ion System, But Not Other Metal-Catalyzed Oxidation Systems, Produces Protein-Bound Dityrosine", Free Radical Biology & Medicine, 31(5): 624-632, 2001.
Kim et al. "High Yield Expression of Recombinant Pro-Resilin: Lactose-Induced Fermentation in *E. coli* and Facile Purification", Protein Expression & Purification, 52: 230-236, 2007.
Klebl et al. "Molecular Cloning of a Cell Wall Exo-?-1,3-Glucanase From *Saccharomyces cerevisiae*", Journal of Bacteriology, 171(11): 6259-6264, Nov. 1989.
Klee et al. "Agrobacterium-Mediated Plants Transformation and Its Further Applications to Plant Biology", Annual Review of Plant Physiology, 38: 467-486, 1987.
Kumar et al. "Designer Protein-Based Performance Materials", Biomacromolecules, 7: 2543-2551, 2006.
Kuranda et al. "Chitinase Is Required for Cell Separation During Growth of *Saccharomyces cerevisiae*", The Journal of Biological Chemistry, 266(29): 19758-19767, Oct. 15, 1991.
Langer "Biomaterials in Drug Delivery and Tissue Engineering: One Laboratory's Experience", Accounts of Chemical Research, 33(2): 94-101, 2000.
Langer "Selected Advances in Drug Delivery and Tissue Engineering", Journal of Controlled Release, 62: 7-11, 1999.
Lawson et al. "Nucleotide Sequence and X-Ray Structure of Cyclodextrin Glycosyltransferase From *Bacillus circulans* Strain 251, in a Maltose-Dependent Cystal Form", Journal of Molecular Biology, 236(Chap.2): 590-600, 1994.
Lazaris et al. "Spider Silk Fibers Spun From Soluble Recombinant Silk Produced in Mammalian Cells", Science, 295: 472-476, Jan. 18, 2002.
Lee et al. "Co—and Post-Translational Processing of the Hevein Preproprotein of Latex of the Rubber Tree (Hevea Brasiliensis)", The Journal of Biological Chemistry, 266(24): 15944-15948, Aug. 25, 1991.
Lehrer et al. "Ultraviolet Irradiation Effects in Poly-L-Tyrosine and Model Compounds. Identification of Bityrosine as a Photoproduct", Biochemistry, 6(3): 757-767, Mar. 1967.
Lerner et al. "The Gene for Stinging Nettle Lectin (Urtica Dioica Agglutinin) Encodes Both a Lectin and a Chitinase", The Journal of Biological Chemistry, 267(16): 11085-11091, Jun. 5, 1992.
Levy et al. "Cross Bridging Proteins in Nature and Their Utilization in Bio—and Nanotechnology", Current Protein and Peptide Science, XP009169155, 5(1): 33-49, Jan. 1, 2004.
Levy et al. "Engineering a Bifunctional Starch-Cellulose Cross-Bridge Protein", Biomaterials, XP004485099, 25(10): 1841-1849, May 1, 2004. p. 1841-1849.
Levy et al. "Recombinant Cellulose Crosslinking Protein: A Novel Paper-Modification Biomaterial", Cellulose, XP055060901, 9(1): 91-98, Jan. 1, 2002.
Lewis et al. "Expression and Purification of a Spider Silk Protein: A New Strategy for Producing Repetitive Proteins", Protein Expression and Purification, 7: 400-406, 1996.
Lim et al. "Cationic Hyperbranched Poly(Amino Ester): A Novel Class of DNA Condensing Molecule With Cationic Surface, Biodegradable Three-Dimensional Structure, and Tertiary Amine Groups in the Interior", Journal of the American Chemical Society, 123: 2460-2461, 2001.
Lucas et al. "Amino-Terminal Sequence of Ethylene-Induced Bean Leaf Chitinase Reveals Similarities to Sugar-Binding Domains of Wheat Germ Agglutinin", The FEBS Letters, 193(2): 208-210, Dec. 1985.
Lyons et al. "Design and Facile Production of Recombinant Resilin-Like Polypeptides: Gene Construction and a Rapid Protein Purification Method", Protein Engineering, Design & Selection, 20(1): 25-32, Jan. 11, 2007.
Malencik et al. "Dityrosine Formation in Calmodulin: Cross-Linking and Polymerization Catalyzed by Arthromyces Peroxidase", Biochemistry, 35: 4375-4386, 1996.
Martino et al. "Biopolymers and Biomaterials Based on Elastomeric Proteins", Macromolecular Bioscience, 2: 319-328, 2002.
Meirovitch et al. "Protein Engineering of Cellulose—Spider Silk Composite", Poster Abstract Presented at the MRS Spring Meeting Symposium T: The Nature of Design—Utilizing Biology's Portfolio, XP002519708, [Online], Apr. 10-Apr. 13, 2007, p. 1-10, Apr. 10, 2007. Retrieved From the Internet. Abstract.
Murray et al. "Dodon Usage in Plant Genes", Nucleic Acids Research, 17(2): 477-498, 1989.
Nazarov et al. "Porous 3-D Scaffolds From Regenerated Silk Fibroin", Biomacromolecules, 5: 718-726, 2004.
Neff et al. "Identification of Resilin in the Leg of Cockroach, Periplaneta Americana: Confirmation by a Simple Method Using pH Dependence of UV Fluorescence", Arthropod Structure and Development, 29: 75-83, 2000.

(56) References Cited

OTHER PUBLICATIONS

Neuhaus et al. "Plant Transformation by Microinjection Techniques", Physiologia Plantarum, 79: 213-217, 1990.
Nishizawa et al. "Rice Chitinase Gene: cDNA Cloning and Stress-induced Expression", Plant Science, 76: 211-218, 1991.
Noishiki et al. "Mechanical Properties of Silk Fibroin-Microcrystalline Cellulose Composite Films", Journal of Applied Polymer Science, 86: 3425-3429, 2002.
Ohta "High-Efficiency Genetic Transformation of Maize by a Mixture of Pollen and Exogenous DNA", Proc. Natl. Acad. Sci. USA, 83: 715-719, Feb. 1986.
Outchkourov et al. "The Promoter-Terminator of Chrysanthemum RbcS1 Directs Very High Expression Levels in Plants", Planta, XP002519330, 216(6): 1003-1012, Apr. 2003. p. 1003-1012.
Ponstein et al. "A Novel Pathogen—and Wound-Inducible Tobacco (Nicotiana Tabacum) Protein With Antifungal Activity", Plant Physiology, 104: 109-118, 1994.
Potrykus "Gene Transfer to Plants: Assessment of Published Approaches and Results", Annual Review of Plant Physiology and Plant Molecular Biology, 42: 205-225, 1991.
Potter et al. "Regulation of a Hevein-Like Gene in Arabidopsis", Molecular Plant-Microbe Interactions, MPMI, 6(6): 680-685, 1993.
Qin et al. "Expression, Cross-Linking, and Characterization of Recombinant Chitin, Binding Resilin", Biomacromolecules, 10: 3227-3234, 2009.
Qin et al. "Recombinant Exon-Encoded Resilins for Elastomeric Biomaterials", Biomaterials, XP028308445, 32(35): 9231-9243, Nov. 29, 20911.
Raikhel et al. "Isolation and Characterization of a cDNA Clone Encoding Wheat Germ Agglutinin", Proc. Natl. Acad. Sci. USA, 84: 6745-6749, Oct. 1987.
Romero et al. "Sequence of the *Streptococcus pneumoniae* Bacteriophage HB-3 Amidase Reveals High Homology With the Major Host Autolysin", Journal of Bacteriology, 172(9): 5064-5070, Sep. 1990.
Samac et al. "Isolation and Characterization of the Genes Encoding Basic and Acidic Chitinase in Arabidopsis Thalinana", Plant Physiology, 93: 907-914, 1990.
Sanford "Biolistic Plant Transformation", Physiologia Plantarum, 79: 206-209, 1990.
Scheller et al. "Production of Spider Silk Proteins in Tobacco and Potato", Nature Biotechnology, 19: 573-577, Jun. 2001.
Seki et al. "Horseshoe Crab (1,3)-?-D-Glucan-Sensitive Coagulation Factor G. A Serine Protease Zymogen Heterodimer With Similarities to ?-Glutan-Binding Proteins", The Journal of Biological Chemistry, 269(2): 1370-1374, Jan. 14, 1994.
Shareck et al. "Sequences of the Three Genes Specifying Xylanases in *Streptomyces lividans*", Gene, 107: 75-82, 1991.
Shen et al. "Primary Sequence of the Glucanase Gene From Oerskovia Xanthineolytica", the Journal of Biological Chemistry, 266(2): 1058-1063, Jan. 15, 1991.
Shimamoto et al. "Fertile Transgenic Rice Plants Regenerated From Transformed Protoplasts", Nature, 338: 274-276, Mar. 16, 1989.
Shimoi et al. "Characterization of Rarobacter Faecitabidus Protease I, A Yeast-Lytic Serine Protease Having Mannose-Binding Activity", Journal of Biochemistry, 110: 608-613, 1991.
Shimoi et al. "Molecular Structure of Rarobacter Faecitabidus Protease I. A Yeast-Lytic Serine Protease Having Mannose-Binding Activity", The Journal of Biological Chemistry, 267(35): 25189-25195, Dec. 15, 1992.
Shiroza et al. "Sequence Analysis of the GtfB Gene From *Streptococcus mutans*", Journal of Bacteriology, 169(9): 4263-4270, Sep. 1987.
Shoseyov et al. "Carbohydrate Binding Modules: Biochemical Properties and Novel Applications", Microbiology and Molecular Biology Reviews, XP002496582, 70(2): 283-295, Jun. 2006. p. 283-295.
Shoseyov et al. "Sp1 as a Thermostable Protein Scaffold Building Block for Self-Assembly of Composite Materials", Symposium DD: From Biological Materilas to Biomimetic Material Synthesis,
XP002546728, [Online], MRS Spring Meeting San Francisco, CA, USA, Mar. 24-28, 2008, DD3.6, Mar. 26, 2008. Abstract.
Sidhu et al. "*Streptomyces griseus* Protease C. A Novel Enzyme of the Chymotrypsin Superfamily", The Journal of Biological Chemistry, 269(31): 20167-20171, Aug. 5, 1994.
Sigurskjold et al. "Thermodynamics of Ligand Binding to the Starch-Binding Domain of Glucoamylase From *Aspergillus niger*", European Journal of Biochemistry, 225: 133-144, 1994.
Smith et al. "Nucleotide Sequences of cDNA Clones Encoding Wheat Germ Agglutinin Isolectins A and D", Plant Molecular Biology, 13: 601-603, 1989.
Soegaard et al. "Site-Directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley ?-Amylase 1", The Journal of Biological Chemistry, 268(30): 22480-22484, Oct. 25, 1993.
Stanford et al. "Differential Expression Within a Family of Novel Wound-Induced Genes in Potato", Molecular and General Genetics, 215: 200-208, 1989. Abstract.
Studier et al. "Use of T7 RNA Polymerase to Direct Expression of Cloned Genes", Methods in Enzymology, 185(Art.6): 60-89, 1990.
Sun et al. "Cloning and DNA Sequencing of the Dextranase Inhibitor Gene (Dei) From *Streptococcus sobrinus*", Journal of Bacteriology, 176(23): 7213-7222, Dec. 1994.
Svensson et al. "Sequence Homology Between Putative Raw-Starch Binding Domains From Different Starch-Degrading Enzymes", Biochemical Journal Letters, 264: 309-311, 1989.
Takamatsu et al. "Expression of Bacterial Chloramphenicol Acetyltransferase Gene in Tobacco Plants Mediated by TMV-RNA", The EMBO Journal, 6(2): 307-311, 1987.
Tatham et al. "Comparative Structures and Properties of Elastic Proteins", Philosophical Transactions of the Royal Society B: Biological Sciences, 357(1418): 229-234, Feb. 28, 2002.
Tomme et al. "Characterization and Affinity Applications of Cellulose-Binding Domains", Journal of Chromatography B, 715: 283-296, 1998.
Tsujibo et al. "Cloning. Sequence, and Expression of a Chitinase Gene From a Marine Bacterium, Alteromonas Sp. Strain O-7", Journal of Bacteriology, 175(1): 176-181, Jan. 1993.
Ueda et al. "Molecular Cloning and Nucleotide Sequence of the Gene Encoding Chitinase II From Aeromonas Sp. No. 10S-24", Journal of Fermentation and Bioengineering, 78(3): 205-211, 1994.
Ueda et al. "Sequence Analysis of the GtfC Gene From *Streptococcus mutans* GS-5", Gene, 69: 101-109, 1988.
Uhrich et al. "Polymeric Systems for Controlled Drug Release", Chemical Reviews, 99: 3181-3198, 1999.
Vad et al. "Accumulation of Defense-Related Transcripts and Cloning of a Chitinase mRNA From Pea Leaves (Pisum Sativum L.) Inoculated With Ascochyta Pisi Lib.", Plant Science, 92: 69-79, 1993.
Velema et al. "Biopolymer-Based Biomaterials as Scaffolds for Tissue Engineering", Advances in Biochemical Engineering, XP009122920, 102: 187-238, Jul. 18, 2006. p. 187-238.
Vendrely et al. "Biotechnological Production of Spider-Silk Proteins Enables New Applications", Macromolecular Bioscience, XP002546726, 7(4): 401-409, Apr. 10, 2007. p. 401-409.
Villette et al. "Cyclomaltodextrin Glucanotransferase From Bacillus Circulans E 192", Biotechnology and Applied Biochemistry, 16: 57-63, 1992.
Von Eichel-Streiber et al. "Comparative Sequence Analysis of the Clostridium Difficile Toxins A and B", Molecular and General Genetics, 233: 260-268, 1992.
Wang et al. "A Novel Biogradable Gene Carrier Based on Polyphosphoester", Journal of the American Chemical Society, 123: 9480-9481, 2001.
Watanabe et al. "Gene Cloning of Chitinase A1 From Bacillus Circulans WL-12 Revealed Its Evolutionary Relationship to Serratia Chitinase and to the Type III Homology Units of Fibronectin", The Journal of Biological Chemistry, 265(26): 15659-15665, Sep. 15, 1990.
Watanabe et al. "Structure of the Gene Encoding Chitinase D of Bacillus Circulans WL-12 and Possible Homology of the Enzyme

(56) References Cited

OTHER PUBLICATIONS to Other Prokaryotic Chitinases and Class III Plant Chitinases", Journal of Bacteriology, 174(2): 408-414, Jan. 1992.
Weis-Fogh "A Rubber-Like Protein in Insect Cuticle", Journal of Experimental Biology, 37(4): 889-907, 1960.
Weselake et al. "Inhibition of Alpha-Amylase-Catalyzed Starch Granule Hydrolysis by Cycloheptaamylose", Cereal Chemistry, 60(2): 98-101, 1983.
Wren et al. "Nucleotide Sequence of Clostridium Difficile Toxin a Gene Fragment and Detection of Toxigenic Strains by Polymerase Chain Reaction", FEMS Microbiology Letters, 70: 1-6, 1990.
Wright et al. "Primary Structure of Wheat Germ Agglutinin Isolectin 2. Peptide Order Deduced From X-Ray Structure", Biochemistry, 23: 280-287, 1984.
Wright et al. "Sequence Variability in Three Wheat Germ Agglutinin Isolectins: Products of Multiple Genes in Polyploid Wheat", Journal of Molecular Evolution, 28: 327-336, 1989.
Yahata et al. "Structure of the Gene Encoding ?-1,3-Glucanase A1 of Bacillus Circulans WL-12", Gene, 86: 113-117, 1990.
Yamagami et al. "The Complete Amino Acid Sequence of Chitinase-A From the Seeds of Rye (Secale Cereal)", Bioscence, Biotechnology, and Biochemistry, 58(2): 322-329, 1994.
Yanai et al. "Purification of Two Chitinases From Rhizopus Oligosporus and Isolation and Sequencing of the Encoding Genes", Journal of Bacteriology, 174(22): 7398-7406, Nov. 1992.
Yang et al. "Structure and Microporous Formation of Cellulose/Silk Fibroin Blend Membranes. I. Effect of Coagulants", Journal of Membrane Science, 177: 153-161, 2000.
Yoda "Elastomer for Biomedical Applications", Journal of Biomaterials Science, Polymer Edition, 9(6): 561-626, 1998.
Yother et al. "Structural Properties and Evolutionary Relationships of PspA, A Surface Protein of *Strptococcus pneumoniae*, as Revealed by Sequence Analysis", Journal of Bacteriology, 174(2): 601-609, Jan. 1992.
Communication Pursuant to Article 94(3) EPC Dated Aug. 26, 2014 From the European Patent Office Re. Application No. 08853290.8.
Notice of Reason for Rejection Dated May 13, 2014 From the Japanese Patent Office Re. Application No. 2010-535508 and Its Translation Into English.
International Preliminary Report on Patentability Dated Mar. 13, 2013 From the International Bureau of WIPO Re. Application No. PCT/IL2012/050340.
Notice of Allowance Dated Nov. 22, 2014 From the US Patent and Trademark Office Re. U.S. Appl. No. 13/870,032.
Official Action Dated Dec. 31, 2014 From the US Patent and Trademark Office Re. U.S. Appl. No. 14/207,864.
Communication Under Rule 164(2)(a) EPC Dated Jan. 16, 2015 From the European Patent Office Re. Application No. 12766719.4.
Official Action Dated May 18, 2015 From the US Patent and Trademark Office Re. U.S. Appl. No. 14/562,849.
Communication Pursuant to Rule 164(2)(b) and Article 94(3) EPC Dated May 7, 2015 From the European Patent Office Re. Application No. 12766719.4.
Burzio et al. "Reactivity of Peptidyl-Tyrosine to Hydroxylation and Cross-Linking", Protein Science, XP055053855, 10: 753-740, Jan. 2001. p. 736, col. 1, Para 2—p. 739, col. 1, Para 3.
Cha et al. "Bulk Adhesive Strength of Recombinant Hybrid Mussel Adhesive Protein", Biofouling: The Journal of Bioadhesion and Biofilm Research, XP055186011, 25(2): 99-107, Feb. 2009. p. 101, col. 2—p. 102, col. 1, p. 106, col. 1, Para 1.
Fante et al. "Synthesis and Biological Evaluation of a Polyglutamic Acid-Dopamine Conjugate: A New Antiangiogenic Agent", Journal of Medicinal Chemistry, XP055186234, 54(14): 5255-5259, Jun. 28, 2011. p. 5255, col. 2, Para 2—p. 5256, col. 1, Para 1, Fig. Scheme 1.
Kim et al. "Controlled Gene-Eluting Metal Stent Fabricated by Bio-Inspired Surface Modification With Hyaluronic Acid and Deposition of DNA/PEI Polyplexes", International Journal of Pharmaceutics, XP026790385, 384(1-2): 181-188, Available Online Sep. 30, 2009. Para [2.2.].
Qu et al. "An Electrochemical Biosensor for the Detection of Tyrosine Oxidation Induced by Fenton Reaction", Biosensors and Bioelectronics, XP027580155, 26(5): 2292-2296, Available Online Oct. 8, 2010.
Restriction Official Action Dated Feb. 26, 2015 From the US Patent and Trademark Office Re. U.S. Appl. No. 14/562,849.
Office Action Dated May 17, 2015 From the Israel Patent Office Re. Application No. 219461 and Its Translation Into English.
Dismissal of Amendment Dated Nov. 21, 2014 From the Japanese Patent Office Re. Application No. 2010-535508 and Its Translation Into English.
Official Decision of Rejection Dated Nov. 21, 2014 From the Japanese Patent Office Re. Application No. 2010-535508 and Its Translation Into English.
Notice of Reason for Rejection Dated Mar. 4, 2016 From the Japanese Patent Office Re. Application No. 2015-057103 and Its Translation Into English.
Samir et al. "Review of Recent Research Into Cellulosic Whiskers, Their Properties and Their Application in Nanocomposite Field", Biomacromolecules, 6(2): 612-626, Published on Web Jan. 21, 2005.
Office Action Dated Aug. 16, 2016 From the Israel Patent Office Re. Application No. 231220 and Its Translation Into English.
Communication Pursuant to Article 94(3) EPC Dated Jun. 21, 2016 From the European Patent Office Re. Application No. 12766719.4.
Official Action Dated Sep. 28, 2016 From the US Patent and Trademark Office Re. U.S. Appl. No. 15/011,738.
Restriction Official Action Dated Apr. 21, 2016 From the US Patent and Trademark Office Re. U.S. Appl. No. 15/011,738.

\* cited by examiner

| | |
|---|---|
| 1 | MVRPEPPVNS YLPPSDSYGA PGQSGPGGRP SDSYGAPGGG NGGRPSDSYG |
| 51 | APGQGQGQGQ GQGGYAGKPS DTYGAPGGGN GNGGRPSSSY GAPGGGNGGR |
| 101 | PSDTYGAPGG GNGGRPSDTY GAPGGGGNGN GGRPSSSYGA PGQGQGNGNG |
| 151 | GRSSSSYGAP GGGNGGRPSD TYGAPGGGNG GRPSDTYGAP GGGNNGGRPS |
| 201 | SSYGAPGGGN GGRPSDTYGA PGGGNGNGSG GRPSSSYGAP GQGQGGFGGR |
| 251 | PSDSYGAPGQ NQKPSDSYGA PGSGNGNGGR PSSSYGAPGS GPGGRPSDSY |
| 301 | GPPASGSGAG GAGGSGPGGA DYDNDEPAKY EFNYQVEDAP SGLSFGHSEM |
| 351 | RDGDFTTGQY NVLLPDGRKQ IVEYEADQQG YRPQIRYEGD ANDGSGPSGP |
| 401 | GGPGGQNLGA DGYSSGRPGN GNGNGNGGYS GGRPGGQDLG PSGYSGGRPG |
| 451 | GQDLGAGGYS NGKPGGQDLG PGGYSGGRPG GQDLGRDGYS GGRPGGQDLG |
| 501 | ASGYSNGRPG GNGNGGSDGG RVIIGGRVIG GQDGGDQGYS GGRPGGQDLG |
| 551 | RDGYSSGRPG GRPGGNGQDS QDGQGYSSGR PGQGGRNGFG PGGQNGDNDG |
| 601 | SGYRY |

FIG. 1 atgtcgtactaccatcaccatcaccatcacgattacgatatcccaacgaccgaaaacctg
 M  S  Y  Y  H  H  H  H  H  H  D  Y  D  I  P  T  T  E  N  L
tattttcagggcgccatgggaccggagccaccagttaactcgtatctacctccgtccgat
 Y  F  Q  G  A  M  G  P  E  P  P  V  N  S  Y  L  P  P  S  D
agctatggagcaccgggtcagagtggtcccggcggcaggccgtcggattcctatggagct
 S  Y  G  A  P  G  Q  S  G  P  G  G  R  P  S  D  S  Y  G  A
cctggtggtggaaacggtggacggccctcagacagctatggcgctccaggccagggtcaa
 P  G  G  N  G  R  P  S  D  S  Y  G  A  P  G  Q  G  Q
ggacagggacaaggacaaggtggatatgcaggcaagccctcagatacctatggagctcct
 G  Q  G  Q  G  Q  G  G  Y  A  G  K  P  S  D  T  Y  G  A  P
ggtggtggaaatggcaacggaggtcgtccatcgagcagctatggcgctcctggcggtgga
 G  G  G  N  G  N  G  R  P  S  S  S  Y  G  A  P  G  G  G
aacggtggtcgtccttcggatacctacggtgctcctggtggcggaaatggtggacgccca
 N  G  G  R  P  S  D  T  Y  G  A  P  G  G  G  N  G  G  R  P
tcggacacttatggtgctcctggtggtggtggaaatggcaacggcggacgaccttcaagc
 S  D  T  Y  G  A  P  G  G  G  N  G  N  G  R  P  S  S
agctatggagctcctggtcaaggacaaggcaacggaaatggcggtcgctcatcgagcagc
 S  Y  G  A  P  G  Q  G  Q  G  N  G  N  G  G  R  S  S  S
tatggtgctcctggcggtggaaacggcggtcgtccttcggatacctacggtgctcccggt
 Y  G  A  P  G  G  G  N  G  G  R  P  S  D  T  Y  G  A  P  G
ggtggaaacggtggtcgtccttcggatacttacggcgctcctggtggcggcaataatggc
 G  G  N  G  G  R  P  S  D  T  Y  G  A  P  G  G  N  N  G
ggtcgtccctcaagcagctacggcgctcctggtggtggaaacggtggtcgtccatctgac
 G  R  P  S  S  S  Y  G  A  P  G  G  N  G  G  R  P  S  D
acctatggcgctcctggtggcggtaacggaaacggcagcggtggtcgtccttcaagcagc
 T  Y  G  A  P  G  G  G  N  G  N  G  S  G  G  R  P  S  S  S
tatggagctcctggtcagggccaaggtggatttggtggtcgtccatcggactcctatggt
 Y  G  A  P  G  Q  G  Q  G  G  F  G  G  R  P  S  D  S  Y  G
gctcctggtcagaaccaaaaaccatcagattcatatggcgcccctggtagcggcaatggc
 A  P  G  Q  N  Q  K  P  S  D  S  Y  G  A  P  G  S  G  N  G
aacggcggacgtccttcgagcagctatggagctccaggctcaggacctggtggccgaccc
 N  G  G  R  P  S  S  S  Y  G  A  P  G  S  G  P  G  G  R  P
tccgactcctacggacccccagcttctggatcgggagcaggtggcgctggaggcagtgga
 S  D  S  Y  G  P  P  A  S  G  S  G  A  G  G  A  G  G  S  G
cccggcggcgctgactacgataacgatgagggatccaatcactagtgaattcgcggccgc
 P  G  G  A  D  Y  D  N  D  E  G  S  N  H  *

FIG. 2

```
catatgtcgtactaccatcaccatcaccatcacgattacgatatcccaacgaccgaaaac
 M  S  Y  Y  H  H  H  H  H  H  D  Y  D  I  P  T  T  E  N
ctgtattttcagggcgccatgggaccggagccaccagttaactcgtatctacctccgtcc
 L  Y  F  Q  G  A  M  G  P  E  P  P  V  N  S  Y  L  P  P  S
gatagctatggagcaccgggtcagagtggtcccggcggcaggccgtcggattcctatgga
 D  S  Y  G  A  P  G  Q  S  G  P  G  G  R  P  S  D  S  Y  G
gctcctggtggtggaaacggtggacggccctcagacagctatggcgctccaggccagggt
 A  P  G  G  G  N  G  G  R  P  S  D  S  Y  G  A  P  G  Q  G
caaggacagggacaaggacaaggtggatatgcaggcaagccctcagatacctatggagct
 Q  G  Q  G  Q  G  Q  G  G  Y  A  G  K  P  S  D  T  Y  G  A
cctggtggtggaaatggcaacggaggtcgtccatcgagcagctatggcgctcctggcggt
 P  G  G  G  N  G  N  G  G  R  P  S  S  S  Y  G  A  P  G  G
ggaaacggtggtcgtccttcggatacctacggtgctcctggtggcggaaatggtggacgc
 G  N  G  G  R  P  S  D  T  Y  G  A  P  G  G  G  N  G  G  R
ccatcggacacttatggtgctcctggtggtggtggaaatggcaacggcggacgaccttca
 P  S  D  T  Y  G  A  P  G  G  G  G  N  G  N  G  G  R  P  S
agcagctatggagctcctggtcaaggacaaggcaacggaaatggcggtcgctcatcgagc
 S  S  Y  G  A  P  G  Q  G  Q  G  N  G  N  G  R  S  S  S
agctatggtgctcctggcggtggaaacggcggtcgtccttcggatacctacggtgctccc
 S  Y  G  A  P  G  G  G  N  G  G  R  P  S  D  T  Y  G  A  P
ggtggtggaaacggtggtcgtccttcggatacttacggcgctcctggtggcggcaataat
 G  G  G  N  G  G  R  P  S  D  T  Y  G  A  P  G  G  G  N  N
ggcggtcgtccctcaagcagctacggcgctcctggtggtggaaacggtggtcgtccatct
 G  G  R  P  S  S  S  Y  G  A  P  G  G  G  N  G  G  R  P  S
gacacctatggcgctcctggtggcggtaacggaaacggcagcggtggtcgtccttcaagc
 D  T  Y  G  A  P  G  G  G  N  G  N  G  S  G  G  R  P  S  S
agctatggagctcctggtcagggccaaggtggatttggtggtcgtccatcggactcctat
 S  Y  G  A  P  G  Q  G  Q  G  G  F  G  G  R  P  S  D  S  Y
ggtgctcctggtcagaaccaaaaaccatcagattcatatggcgcccctggtagcggcaat
 G  A  P  G  Q  N  Q  K  P  S  D  S  Y  G  A  P  G  S  G  N
ggcaacggcggacgtccttcgagcagctatggagctccaggctcaggacctggtggccga
 G  N  G  G  R  P  S  S  S  Y  G  A  P  G  S  G  P  G  G  R
ccctccgactcctacggacccccagcttctggatcgggagcaggtggcgctggaggcagt
 P  S  D  S  Y  G  P  P  A  S  G  S  G  A  G  G  A  G  G  S
ggacccggcggcgctgactacgataacgatgagcccgccaagtacgaatttaattaccag
 G  P  G  G  A  D  Y  D  N  D  E  P  A  K  Y  E  F  N  Y  Q
gttgaggacgcgcccagcggactctcgttcgggcattcagagatgcgcgacggtgacttc
 V  E  D  A  P  S  G  L  S  F  G  H  S  E  M  R  D  G  D  F
accaccggccagtacaatgtcctgttgcccgacggaaggaagcaaattgtggagtatgaa
 T  T  G  Q  Y  N  V  L  L  P  D  G  R  K  Q  I  V  E  Y  E
gccgaccagcagggctaccggccacagatccgctacgaaggcgatgccaacgatggcagt
 A  D  Q  Q  G  Y  R  P  Q  I  R  Y  E  G  D  A  N  D  G  S
ggtcccagcggtccttaaggatccgagctccgtcgacaagcttgcggccgc
 G  P  S  G  P  *
```

FIG. 3

```
catatgtcgtactaccatcaccatcaccatcacgattacgatatcccaacgaccgaaaac
  M  S  Y  Y  H  H  H  H  H  H  D  Y  D  I  P  T  T  E  N
ctgtattttcagggcgccatgggaccggagccaccagttaactcgtatctacctccgtcc
  L  Y  F  Q  G  A  M  G  P  E  P  P  V  N  S  Y  L  P  P  S
gatagctatggagcaccgggtcagagtggtcccggcggcaggccgtcggattcctatgga
  D  S  Y  G  A  P  G  Q  S  G  P  G  G  R  P  S  D  S  Y  G
gctcctggtggtggaaacggtggacggccctcagacagctatggcgctccaggccagggt
  A  P  G  G  N  G  G  R  P  S  D  S  Y  G  A  P  G  Q  G
caaggacagggacaaggacaaggtggatatgcaggcaagccctcagatacctatggagct
  Q  G  Q  G  Q  G  Q  G  G  Y  A  G  K  P  S  D  T  Y  G  A
cctggtggtggaaatggcaacggaggtcgtccatcgagcagctatggcgctcctggcggt
  P  G  G  N  G  N  G  G  R  P  S  S  S  Y  G  A  P  G  G
ggaaacggtggtcgtccttcggatacctacggtgctcctggtggcggaaatggtggacgc
  G  N  G  G  R  P  S  D  T  Y  G  A  P  G  G  N  G  G  R
ccatcggacacttatggtgctcctggtggtggtggaaatggcaacggcggacgaccttca
  P  S  D  T  Y  G  A  P  G  G  G  N  G  N  G  G  R  P  S
agcagctatggagctcctggtcaaggacaaggcaacggaaatggcggtcgctcatcgagc
  S  S  Y  G  A  P  G  Q  G  Q  G  N  G  N  G  G  R  S  S  S
agctatggtgctcctggcggtggaaacggcggtcgtccttcggatacctacggtgctccc
  S  Y  G  A  P  G  G  N  G  G  R  P  S  D  T  Y  G  A  P
ggtggtggaaacggtggtcgtccttcggatacttacggcgctcctggtggcggcaataat
  G  G  G  N  G  G  R  P  S  D  T  Y  G  A  P  G  G  N  N
ggcggtcgtccctcaagcagctacggcgctcctggtggtggaaacggtggtcgtccatct
  G  G  R  P  S  S  S  Y  G  A  P  G  G  G  N  G  G  R  P  S
gacacctatggcgctcctggtggcggtaacggaaacggcagcggtggtcgtccttcaagc
  D  T  Y  G  A  P  G  G  N  G  N  G  S  G  G  R  P  S  S
agctatggagctcctggtcagggccaaggtggatttggtggtcgtccatcggactcctat
  S  Y  G  A  P  G  Q  G  Q  G  G  F  G  G  R  P  S  D  S  Y
ggtgctcctggtcagaaccaaaaaaccatcagattcatatggcgcccctggtagcggcaat
  G  A  P  G  Q  N  Q  K  P  S  D  S  Y  G  A  P  G  S  G  N
ggcaacggcggacgtccttcgagcagctatggagctccaggctcaggacctggtggccga
  G  N  G  G  R  P  S  S  S  Y  G  A  P  G  S  G  P  G  G  R
ccctccgactcctacggaccccagcttctggatcgggagcaggtggcgctggaggcagt
  P  S  D  S  Y  G  P  P  A  S  G  S  G  A  G  G  A  G  G  S
ggacccggcggcgctgactacgataacgatgaggggatccccgaccccggcatggcagcg
  G  P  G  G  A  D  Y  D  N  D  E  G  I  P  D  P  G  M  A  A
acatcatcaatgtcagttgaattttacaactctaacaaatcagcacaaacaaactcaatt
  T  S  S  M  S  V  E  F  Y  N  S  N  K  S  A  Q  T  N  S  I
acaccaataatcaaaattactaacacatctgacagtgatttaaatttaaatgacgtaaaa
  T  P  I  I  K  I  T  N  T  S  D  S  D  L  N  L  N  D  V  K
gttagatattattacacaagtgatggtacacaaggacaaactttctggtgtgaccatgct
  V  R  Y  Y  Y  T  S  D  G  T  Q  G  Q  T  F  W  C  D  H  A
ggtgcattattaggaaatagctatgttgataacactagcaaagtgacagcaaacttcgtt
  G  A  L  L  G  N  S  Y  V  D  N  T  S  K  V  T  A  N  F  V
aaagaaacagcaagcccaacatcaacctatgatacatatgttgaatttggatttgcaagc
  K  E  T  A  S  P  T  S  T  Y  D  T  Y  V  E  F  G  F  A  S
ggacgagctactcttaaaaaggacaatttataactattcaaggaagaataacaaaatca
  G  R  A  T  L  K  K  G  Q  F  I  T  I  Q  G  R  I  T  K  S
gactggtcaaactacactcaaacaaatgactattcatttgatgcaagtagttcaacacca
  D  W  S  N  Y  T  Q  T  N  D  Y  S  F  D  A  S  S  S  T  P
gttgtaaatccaaaagttacaggatatataggtggagctaaagtacttggtacagcacca
  V  V  N  P  K  V  T  G  Y  I  G  G  A  K  V  L  G  T  A  P
taggatcgatccagatgtac
  *
```

FIG. 4

```
catatgtcgtactaccatcaccatcaccatcacgattacgatatcccaacgaccgaaaac
    M  S  Y  Y  H  H  H  H  H  H  D  Y  D  I  P  T  T  E  N
ctgtattttcagggcgccatggcagcgacatcatcaatgtcagttgaattttacaactct
  L  Y  F  Q  G  A  M  A  A  T  S  S  M  S  V  E  F  Y  N  S
aacaaagcagcacaaacaaactcaattacaccaataatcaaaattactaacacagctgac
  N  K  A  A  Q  T  N  S  I  T  P  I  I  K  I  T  N  T  A  D
agtgatttaaatttaaatgacgtaaaagttagatattattacaagtgatggtacacaa
  S  D  L  N  L  N  D  V  K  V  R  Y  Y  Y  T  S  D  G  T  Q
ggacaaactttctggggtgatcatgctggtgcattattaggaaatagctatgttgataac
  G  Q  T  F  W  G  D  H  A  G  A  L  L  G  N  S  Y  V  D  N
actggcaaagtgacagcaaacttcgttaaagaaacagcaagcccaacatcaacctatgat
  T  G  K  V  T  A  N  F  V  K  E  T  A  S  P  T  S  T  Y  D
acatatgttgaatttggatttgcaagcggagcagctactcttaaaaaggacaatttata
  T  Y  V  E  F  G  F  A  S  G  A  A  T  L  K  K  G  Q  F  I
actattcaaggaagaataacaaaatcagactggtcaaactacgctcagacaaatgactat
  T  I  Q  G  R  I  T  K  S  D  W  S  N  Y  A  Q  T  N  D  Y
tcatttgatgcaagtagttcaacaccagttgtaaatccaaaagttacaggatatataggt
  S  F  D  A  S  S  S  T  P  V  V  N  P  K  V  T  G  Y  I  G
ggagctaaagtacttggtacagcaccaggtccagatgtaccatcttcaataattaatcct
  G  A  K  V  L  G  T  A  P  G  P  D  V  P  S  S  I  I  N  P
acttctgcaacatttgatccggagccaccagttaactcgtatctacctccgtccgatagc
  T  S  A  T  F  D  P  E  P  P  V  N  S  Y  L  P  P  S  D  S
tatggagcaccgggtcagagtggtcccggcggcaggccgtcggattcctatggagctcct
  Y  G  A  P  G  Q  S  G  P  G  G  R  P  S  D  S  Y  G  A  P
ggtggtggaaacggtggacggccctcagacagctatggcgctccaggccagggtcaagga
  G  G  G  N  G  G  R  P  S  D  S  Y  G  A  P  G  Q  G  Q  G
cagggacaaggacaaggtggatatgcaggcaagccctcagatacctatggagctcctggt
  Q  G  Q  G  Q  G  Y  A  G  K  P  S  D  T  Y  G  A  P  G
ggtggaaatggcaacggaggtcgtccatcgagcagctatggcgctcctggcggtggaaac
  G  G  N  G  N  G  R  P  S  S  S  Y  G  A  P  G  G  G  N
ggtggtcgtccttcggatacctacggtgctcctggtggcggaaatggtggacgcccatcg
  G  G  R  P  S  D  T  Y  G  A  P  G  G  N  G  G  R  P  S
gacacttatggtgctcctggtggtggtggaaatggcaacggcggacgaccttcaagcagc
  D  T  Y  G  A  P  G  G  G  N  G  N  G  G  R  P  S  S  S
tatggagctcctggtcaaggacaaggcaacggaaatggcggtcgctcatcgagcagctat
  Y  G  A  P  G  Q  G  Q  G  N  G  N  G  G  R  S  S  S  S  Y
ggtgctcctggcggtggaaacggcggtcgtccttcggatacctacggtgctcccggtggt
  G  A  P  G  G  G  N  G  G  R  P  S  D  T  Y  G  A  P  G  G
ggaaacggtggtcgtccttcggatacttacggcgctcctggtggcggcaataatggcggt
  G  N  G  G  R  P  S  D  T  Y  G  A  P  G  G  G  N  N  G  G
cgtccctcaagcagctacggcgctcctggtggtggaaacggtggtcgtccatctgacacc
  R  P  S  S  S  Y  G  A  P  G  G  G  N  G  G  R  P  S  D  T
tatggcgctcctggtggcggtaacggaaacggcagcggtggtcgtccttcaagcagctat
  Y  G  A  P  G  G  G  N  G  N  G  S  G  G  R  P  S  S  S  Y
ggagctcctggtcagggccaaggtggatttggtggtcgtccatcggactcctatggtgct
  G  A  P  G  Q  G  Q  G  G  F  G  G  R  P  S  D  S  Y  G  A
cctggtcagaaccaaaaaccatcagattcatatggcgcccctggtagcggcaatggcaac
  P  G  Q  N  Q  K  P  S  D  S  Y  G  A  P  G  S  G  N  G  N
ggcggacgtccttcgagcagctatggagctccaggctcaggacctggtggccgaccctcc
  G  G  R  P  S  S  S  Y  G  A  P  G  S  P  G  G  R  P  S
gactcctacggacccccagcttctggatcgggagcaggtggcgctggaggcagtggaccc
  D  S  Y  G  P  P  A  S  G  S  G  A  G  G  A  G  G  S  G  P
ggcggcgctgactacgataacgatgagtaaggatccgagctccgtcgacaagcttgcggc
  G  G  A  D  Y  D  N  D  E  *
```

FIG. 5

ADHESIVE BIOPOLYMERS AND USES THEREOF

RELATED APPLICATIONS

This application is a National Phase of PCT Patent Application No. PCT/IL2012/050340 having International filing date of Aug. 30, 2012, which claims the benefit of priority under 35 USC §119(e) of U.S. Provisional Patent Application No. 61/530,167 filed on Sep. 1, 2011. The contents of the above applications are all incorporated by reference as if fully set forth herein in their entirety.

SEQUENCE LISTING STATEMENT

The ASCII file, entitled 58307SequenceListing.txt, created on Jan. 5, 2014, comprising 47,515 bytes, submitted concurrently with the filing of this application is incorporated herein by reference.

FIELD AND BACKGROUND OF THE INVENTION

The present invention, in some embodiments thereof, relates to adhesive biopolymers and uses thereof.

The replacement or repair of damaged or diseased tissues or organs by implantation has been, and continues to be, a long-standing goal of medicine towards which tremendous progress has been made. Working toward that goal, there is an increasing interest in tissue engineering techniques where biocompatible, biodegradable materials are used as adhesives.

A variety of adhesives found in nature, such as barnacle glue, appear to have excellent polymerization and mechanical properties. However, development of natural product based glues has been hampered by the ability to purify appreciable quantities of such materials, as well as persistent concerns about the triggering of an immune response by foreign glycoproteins.

Owing to the above-described limitations, considerable development effort has been directed towards finding a suitable synthetic composition operative as a tissue glue. To this end, cyanoacrylates, polyurethanes, polymethylmethacrylates, among other synthetic polymers, have been investigated as tissue glues. Each of these synthetic compositions has met with limited success owing to a variety of problems such as toxic degradation products, poor mechanical properties, cure exotherms that overheat surrounding tissue, and not being biodegradable. The replacement or repair of damaged or diseased tissues or organs by implantation has been, and continues to be, a long-standing goal of medicine towards which tremendous progress has been made. Working toward that goal, there is an increasing interest in tissue engineering techniques where biocompatible, biodegradable materials are used as adhesives.

Many elastomeric proteins are found in a diverse range of animal species and tissues and possess rubber-like elasticity, undergoing high deformation without rupture, storing the energy involved in deformation, and then returning to their original state when the stress is removed [33]. Protein elasticity remains to be fully described due to the large size and complexity of these proteins which has led to difficulties in isolation and purification [32]. Only a few elastomeric proteins, especially elastin, abductin, resilin and some spider silks, have been studied for mechanical and biochemical properties, and their potential as biomaterials for industrial and biomedical applications has been documented [16, 18, 34, 35]. In nature, resilin and elastin have achieved near-perfect elasticity, and these two elastomeric proteins can be stretched more than twice their original length and recover more than 90% of the deformation energy once the stretching (compression) force is removed [32]. The latter property is called resilience, hence the name "resilin".

Resilin is found in specialized cuticle regions in many insects, especially in areas where high resilience and low stiffness are required, or as an energy storage system. It is best known for its roles in insect flight and the remarkable jumping ability of fleas and spittlebugs. The protein was initially identified in 1960 by Weis-Fogh who isolated it from cuticles of locusts and dragonflies and described it as a rubber-like material.

Resilin displays unique mechanical properties that combine reversible deformation with very high resilience. It has been reported to be the most highly efficient elastic material known.

Ardell et al. identified the gene product CG15920 as a tentative *D. melanogaster* resilin precursor, which had the three exons: N-terminal region (exon 1, containing signal peptide and elastic repeats), chitin-binding domain (ChBD; exon 2), and C-terminal region (exon 3, with other types of elastic repeats) [9]. Exon 2 in *D. melanogaster* resilin, identified as ChBD type R&R-2, has been studied experimentally for chitin binding to resilin [12]. Exon 1 and exon 3 domains contain regions of highly repetitive segments (elastic repeats), which are rich in proline and glycine similar to most proteins that have long-range elasticity.

Based on the first exon of CG15920, a recombinant resilin-like protein (rec1) was successfully expressed, purified and photo-chemically cross-linked to form a resilient elastic biomaterial [16]. Surface-induced assembly of this biomaterial has been investigated through direct imaging using AFM [17], and the recombinant materials from exon 1 exhibited potentially useful mechanical and cell adhesion behavior [18].

The full length resilin containing all three exons in *D. melanogaster* CG15920 have also expressed, purified without affinity tags, and cross-linked by HRP (horseradish peroxidase). A high degree of disorder and high resilience were exhibited by the full length resilin (exon 1+exon 2+exon 3) [12].

Resilin and composites thereof have been described in International Application No. WO 2009/069123.

Elastic proteins often contain repeat sequences forming elastomeric domains, and additional domains that form intermolecular cross-links [39, 40]. Elasticity depends on the length of elastic sequence and the extent of cross-linking. The presence of a network of cross-links (covalent or noncovalent) is a common feature to most of these proteins [14, 37].

Natural resilin is cross-linked in insect cuticle via di-tyrosine formation via enzymes, resulting in an almost perfect 3D elastomer. Both enzyme-based and Ru-based methods have been reported for resilin polymerization [12, 16].

Cross-linking of resilin proteins has been reported to produce high molecular weight cross-linked polymeric material by using horseradish peroxidase, an enzyme known to catalyze di-tyrosine formation, and present in extracts of resilin from the adult desert locust (*Schistocerca gregaria*) [4, 41].

SUMMARY OF THE INVENTION

According to an aspect of some embodiments of the present invention there is provided a polymer having the general formula I:

A-L-B                                      Formula I wherein:
B is a biopolymer;
L is a linking moiety; and
A is a dihydroxyphenyl moiety having the general formula II:

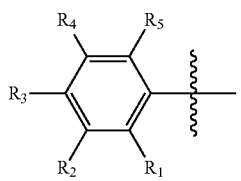

Formula II wherein each of $R_1$-$R_5$ is independently selected from the group consisting of hydrogen, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, and at least two of $R_1$-$R_5$ are hydroxy.

According to an aspect of some embodiments of the present invention there is provided a method of preparing the polymer of the invention, the method comprising:
a) providing a compound comprising the dihydroxyphenyl moiety and the reactive group; and
b) contacting the compound with a biopolymer comprising at least one of the functional group to form the covalent bond,
thereby preparing the polymer.

According to an aspect of some embodiments of the present invention there is provided a method of preparing the polymer of the invention, the method comprising:
a) providing a biopolymer comprising at least one hydroxyphenyl moiety; and
b) oxidizing at least one of the at least one hydroxyphenyl moiety to form the dihydroxyphenyl moiety,
thereby preparing the polymer.

According to an aspect of some embodiments of the present invention there is provided a polymer prepared according to any of the described methods.

According to an aspect of some embodiments of the present invention there is provided a method of generating a crosslinked adhesive, the method comprising contacting the polymer of the invention with an oxidizing agent, to thereby crosslink the dihydroxyphenyl moieties of the polymer.

According to an aspect of some embodiments of the present invention there is provided a crosslinked adhesive generated according to the method of the present invention.

According to an aspect of some embodiments of the present invention there is provided a method of binding a first agent to a second agent, the method comprising contacting the first agent with the agent in a presence of the polymer of the present invention and an oxidizing agent.

According to an aspect of some embodiments of the present invention there is provided a kit comprising:
a) an adhesive comprising the polymer the invention; and
b) an oxidizing agent.

According to an aspect of some embodiments of the present invention there is provided a kit comprising:
a) an adhesive comprising a biopolymer which comprises at least one hydroxyphenyl moiety; and
b) agents for performing a Fenton reaction.

According to an aspect of some embodiments of the present invention there is provided a crosslinked polymer having the general formula III:

B'-L'-A'-A"-L"-B"                        Formula III wherein:
B' and B" are each a biopolymer;
L' and L" are each a linking moiety; and
A'-A" is a pair of crosslinked dihydroxyphenyl moieties, the pair having a formula selected from the group consisting of:

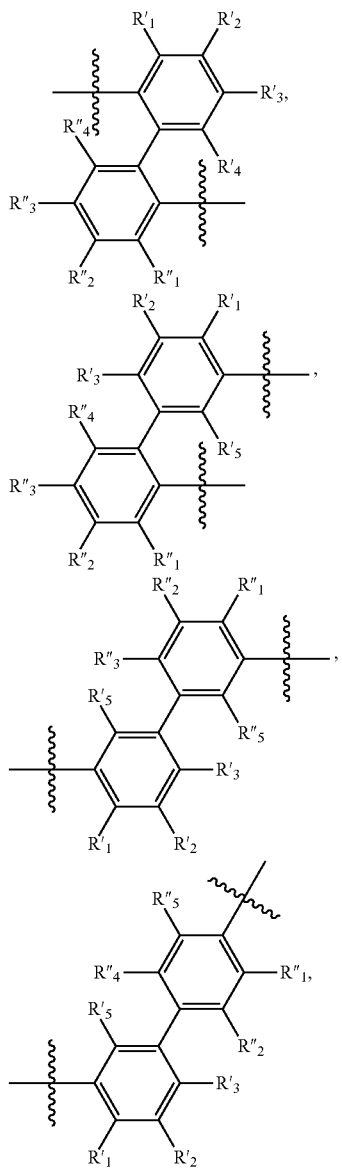

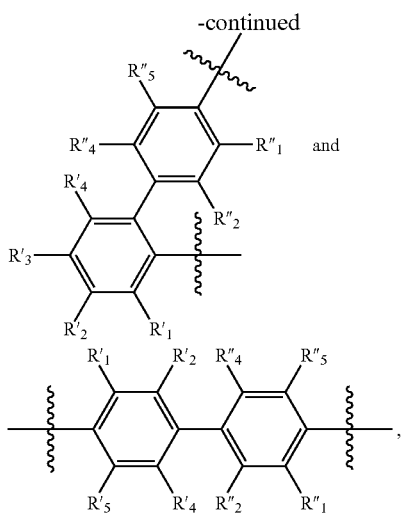

wherein each of $R'_1$-$R'_5$ and $R''_1$-$R''_5$ is independently selected from the group consisting of hydrogen, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, and at least two of $R'_1$-$R'_5$ and at least two of $R''_1$-$R''_5$ are hydroxy, with the proviso that the biopolymer is not comprised by a polysaccharide-fibrous polypeptide composite.

According to some embodiments of the invention, the $R_3$ is hydroxy.

According to some embodiments of the invention, the $R_2$ is hydroxy.

According to some embodiments of the invention, at least one of $R_1$-$R_5$ is hydrogen.

According to some embodiments of the invention, the $R_1$, $R_4$ and $R_5$ are each hydrogen.

According to some embodiments of the invention, the biopolymer is selected from the group consisting of a polypeptide and a polysaccharide.

According to some embodiments of the invention, the polypeptide comprises at least one resilin amino acid sequence.

According to some embodiments of the invention, the at least one resilin amino acid sequence comprises a sequence as set forth in SEQ ID NO: 1 or 2.

According to some embodiments of the invention, the at least one resilin amino acid sequence further comprises a sequence as set forth in SEQ ID NO: 3 or 6.

According to some embodiments of the invention, the polymer is substantially devoid of crosslinking by the dihydroxyphenyl moiety.

According to some embodiments of the invention, the dihydroxyphenyl moiety and the linking moiety form a part of a DOPA residue.

According to some embodiments of the invention, the dihydroxyphenyl moiety and the linking moiety do not form a part of a DOPA residue.

According to some embodiments of the invention, the linking moiety is attached to the biopolymer via a covalent bond formed between a reactive group in the linking moiety and a functional group on the biopolymer.

According to some embodiments of the invention, the functional group is selected from the group consisting of amine, carboxylic acid and thiohydroxy.

According to some embodiments of the invention, the covalent bond is selected from the group consisting of amide, amine and thioether.

According to some embodiments of the invention, the linking moiety comprises a hydrocarbon chain linking the reactive group to the dihydroxyphenyl moiety, the hydrocarbon chain being saturated or unsaturated, and substituted or non-substituted.

According to some embodiments of the invention, the polymer comprises a plurality of the dihydroxyphenyl moiety.

According to some embodiments of the invention, the polymer comprises from 3 to 15 dihydroxyphenyl moieties.

According to some embodiments of the invention, the polymer is characterized by a ratio of molecular weight to dihydroxyphenyl moieties in a range of from 1.5 KDa per dihydroxyphenyl moiety to 12 KDa per dihydroxyphenyl moiety.

According to some embodiments of the invention, the ratio is in a range of from 2.5 KDa per dihydroxyphenyl moiety to 8 KDa per dihydroxyphenyl moiety.

According to some embodiments of the invention, the polymer is a polypeptide wherein a percentage of amino acid residues of the polypeptide which comprise the dihydroxyphenyl moiety is in a range of from 0.5% to 5%.

According to some embodiments of the invention, the percentage of the amino acid residues which comprise the dihydroxyphenyl moiety is in a range of from 1% to 3%.

According to some embodiments of the invention, the polymer is a polypeptide comprising at least one DOPA residue, wherein a ratio of a number of DOPA residues to a number of tyrosine residues in the polypeptide is at least 1:5.

According to some embodiments of the invention, the polymer exhibits an adhesiveness to a surface, the adhesiveness being characterized by resistance to stress of 1 KPa in a direction perpendicular to said surface.

According to some embodiments of the invention, the hydroxyphenyl moiety is comprised by a tyrosine residue in the biopolymer.

According to some embodiments of the invention, the oxidizing converts the tyrosine residue to a DOPA residue.

According to some embodiments of the invention, the oxidizing is effected by contacting the biopolymer with a tyrosine hydroxylase.

According to some embodiments of the invention, the polymer comprising the dihydroxyphenyl moiety is substantially devoid of crosslinking by the dihydroxyphenyl moiety.

According to some embodiments of the invention, the oxidizing is effected by a Fenton reaction.

According to some embodiments of the invention, the method comprises contacting the biopolymer with iron-(II), hydrogen peroxide and citrate.

According to some embodiments of the invention, the Fenton reaction is induced by illumination.

According to some embodiments of the invention, the oxidizing further crosslinks a portion of the dihydroxyphenyl moieties, so as to form a crosslinked polymer.

According to some embodiments of the invention, the oxidizing agent is selected from the group consisting of a periodate, a peroxide, a hypochlorite, a tyrosinase, a peroxidase, a photosensitizer, and ionizing radiation.

According to some embodiments of the invention, the polymer is used as an adhesive, by contacting the polymer with an oxidizing agent.

According to some embodiments of the invention, the contacting is effected in vivo.

According to some embodiments of the invention, the oxidizing agent is selected from the group consisting of a periodate, a peroxide, a hypochlorite, a tyrosinase, a peroxidase, a photosensitizer, and ionizing radiation.

According to some embodiments of the invention, the oxidizing agent is selected from the group consisting of a periodate, a peroxide, a hypochlorite, a tyrosinase, a peroxidase, and a photosensitizer.

According to some embodiments of the invention, the agents comprise iron-(II), hydrogen peroxide and citrate.

According to some embodiments of the invention, the $R'_3$ and $R''_3$ are each hydroxy.

According to some embodiments of the invention, at least one of $R'_2$ and $R'_4$ is hydroxy, and at least one of $R''_2$ and $R''_4$ is hydroxy.

According to some embodiments of the invention, each of $R'_1$-$R'_5$ and $R''_1$-$R''_5$ is independently selected from the group consisting of hydrogen and hydroxy.

According to some embodiments of the invention, the B' and B" are each independently a biopolymer selected from the group consisting of a polypeptide and a polysaccharide.

According to some embodiments of the invention, at least one of B' and B" comprises at least one resilin amino acid sequence.

According to some embodiments of the invention, neither B' nor B" is a resilin.

According to some embodiments of the invention, wherein A'-L' or A"-L" each form a part of a DOPA residue.

According to some embodiments of the invention, at least one of A'-L' and A"-L" does not form a part of a DOPA residue.

According to some embodiments of the invention, wherein at least one of L' and L" is attached to the biopolymer via a covalent bond formed between a reactive group in the linking moiety and a functional group on the biopolymer.

According to some embodiments of the invention, the functional group is selected from the group consisting of amine, carboxylic acid and thiohydroxy.

According to some embodiments of the invention, the covalent bond is selected from the group consisting of amide, amine and thioether.

According to some embodiments of the invention, at least one of L' and L" comprises a hydrocarbon chain linking the reactive group to the dihydroxyphenyl moiety, the hydrocarbon chain being saturated or unsaturated, and substituted or non-substituted.

According to some embodiments of the invention, the crosslinked polymer comprises a plurality of the pair of crosslinked dihydroxyphenyl moieties.

According to some embodiments of the invention, the crosslinked polymer comprises from 3 to 15 pairs of crosslinked dihydroxyphenyl moieties.

According to some embodiments of the invention, the crosslinked polymer is characterized by a ratio of molecular weight to crosslinked dihydroxyphenyl moieties in a range of from 1.5 KDa per crosslinked dihydroxyphenyl moiety to 12 KDa per crosslinked dihydroxyphenyl moiety.

According to some embodiments of the invention, the ratio is in a range of from 2.5 KDa to 8 KDa per crosslinked dihydroxyphenyl moiety.

According to some embodiments of the invention, wherein a percentage of amino acid residues of the crosslinked polypeptide which comprise the dihydroxyphenyl moiety is in a range of from 0.5% to 5%.

According to some embodiments of the invention, wherein a percentage of the amino acid residues which comprise the dihydroxyphenyl moiety is in a range of from 1% to 3%.

According to some embodiments of the invention, the crosslinked polypeptide comprises at least one DOPA residue, wherein a ratio of a number of DOPA residues to a number of tyrosine residues in the crosslinked polypeptide is at least 1:5.

According to some embodiments of the invention, the crosslinked polymer exhibits an adhesiveness to a surface, the adhesiveness being characterized by resistance to shear stress of 1.5 MPa.

According to some embodiments of the invention, the crosslinked polymer exhibits an adhesiveness to a surface, the adhesiveness being characterized by resistance to stress of 10 KPa in a direction perpendicular to said surface.

According to some embodiments of the invention, the surface comprises collagen.

According to some embodiments of the invention, the surface comprises cartilage.

According to some embodiments of the invention, the crosslinked polymer is characterized as being elastic under a compression strain of 60%.

According to some embodiments of the invention, the crosslinked polymer is characterized as being elastic under a compression stress of 150 KPa.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 6:
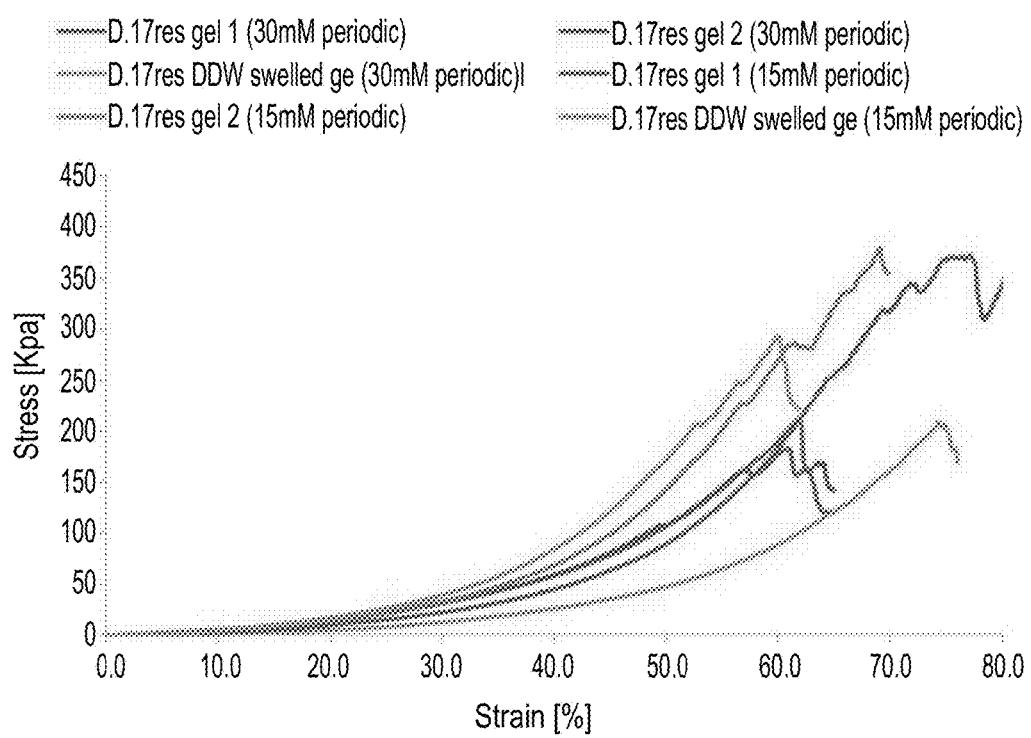
Figure 7:
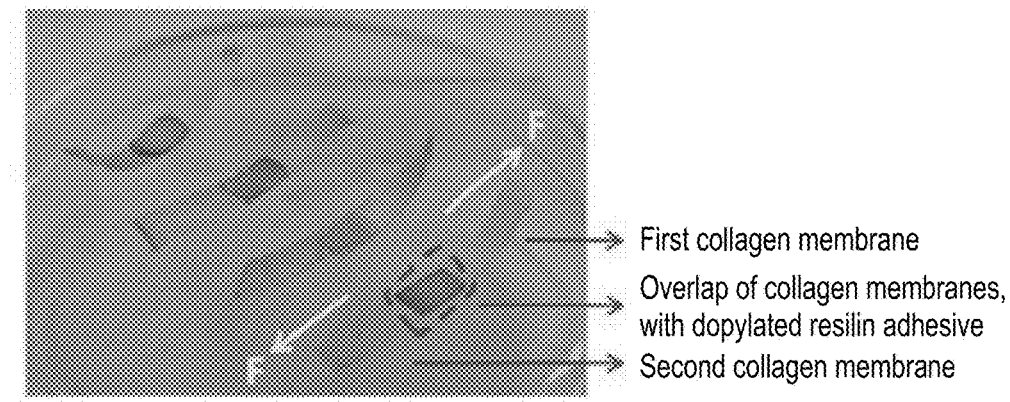
Figure 8:
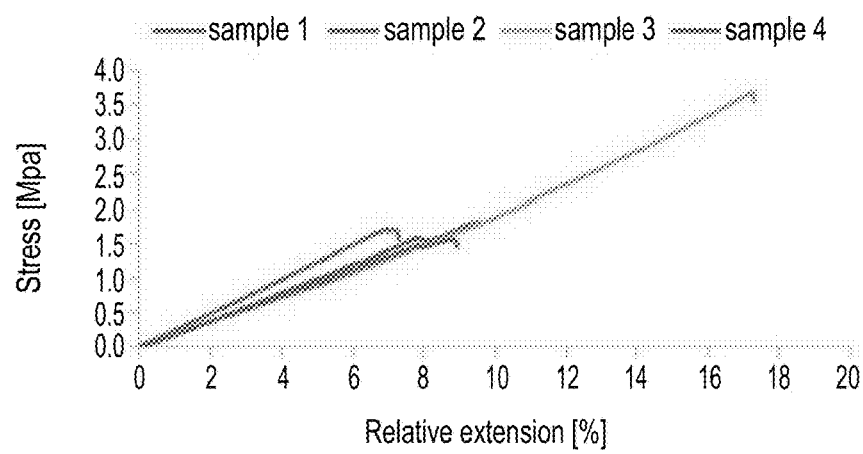
Figures 9A, 9B:
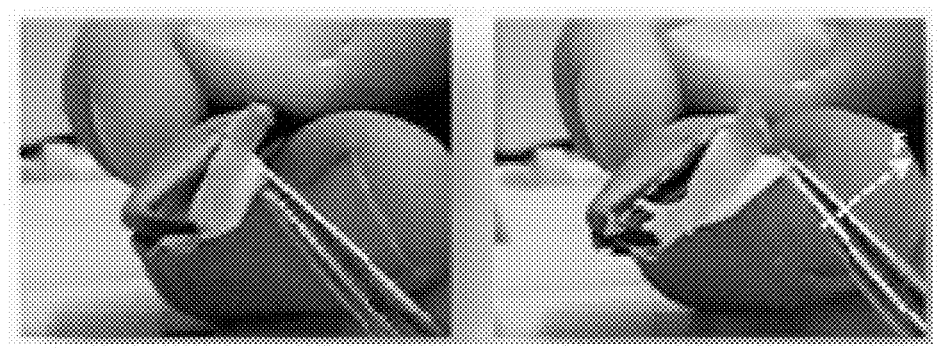
Figures 10A, 10B, 10C:
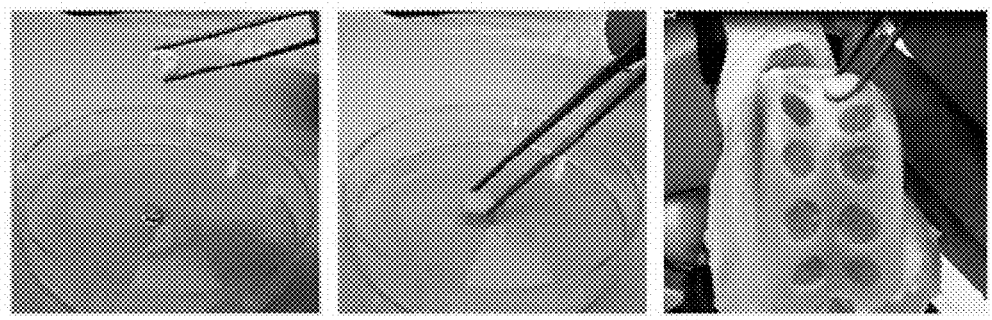
Figure 11:
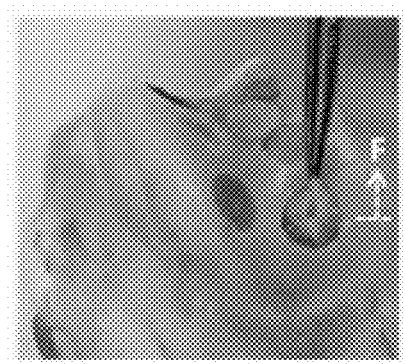
Figure 12:
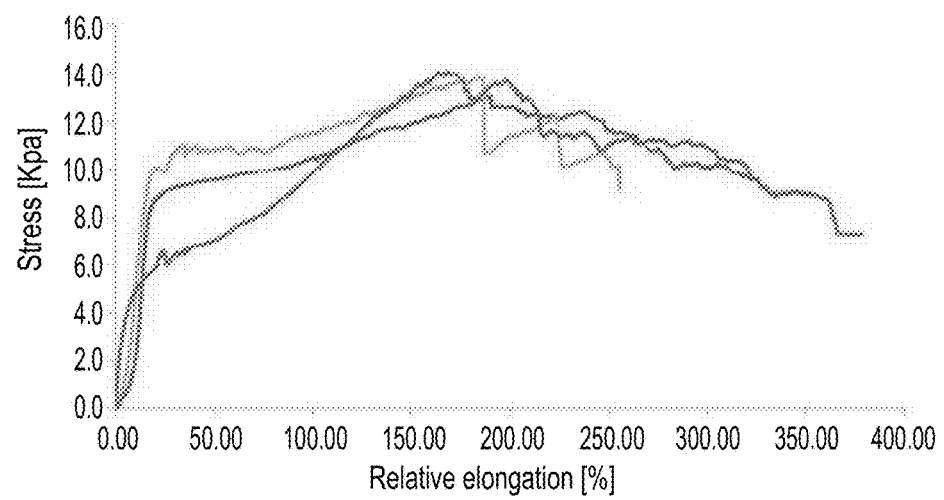
Figure 13A:
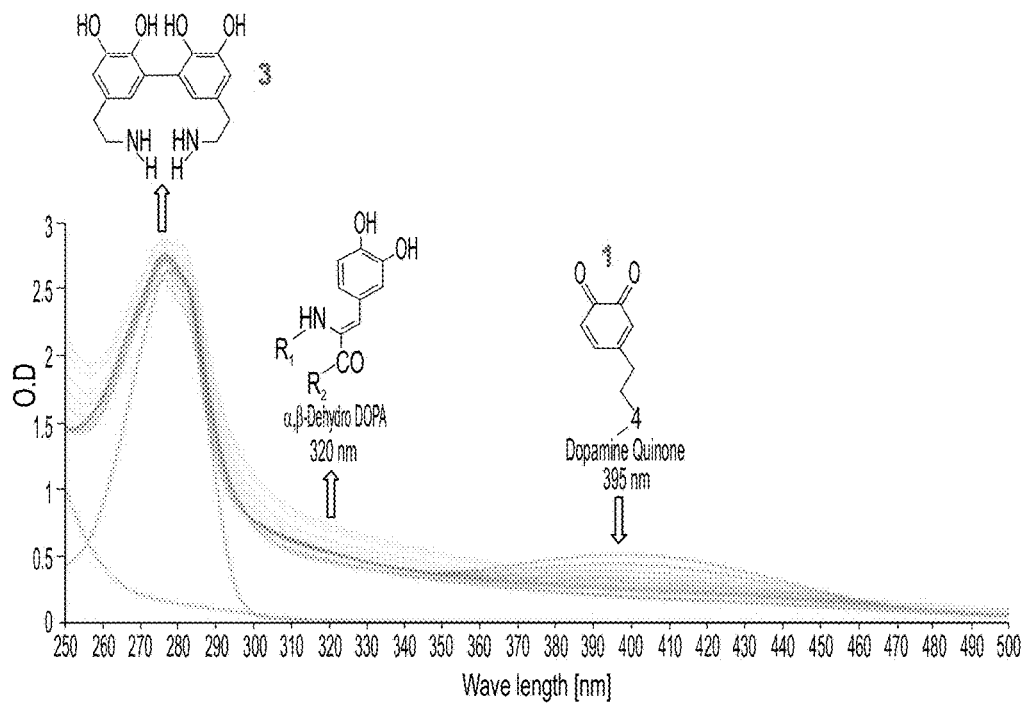
Figure 13B:
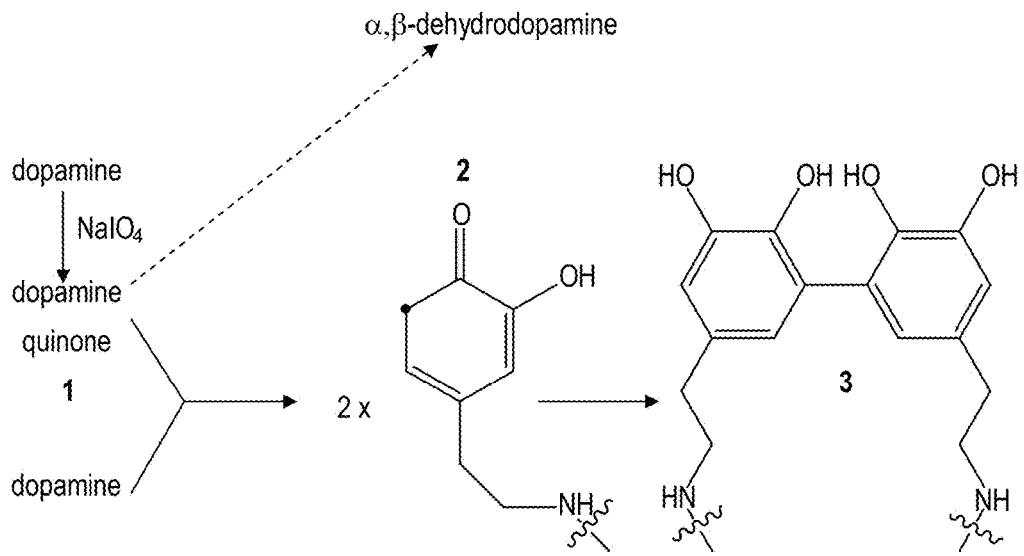
Figure 14:
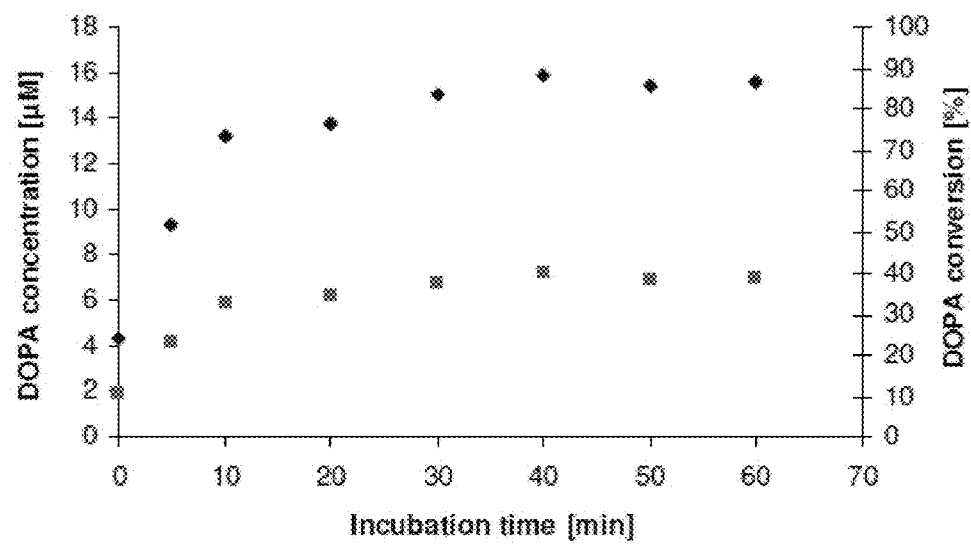
Figure 15:
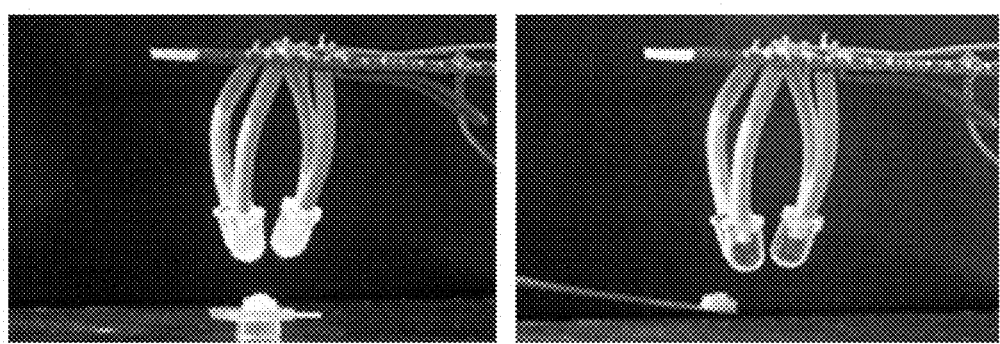
Figure 16:
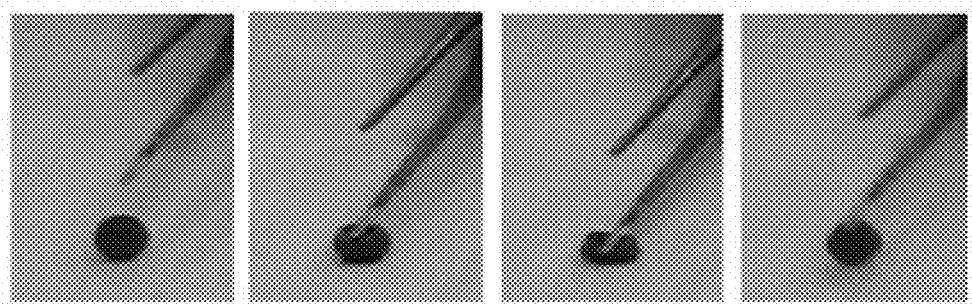
Figure 17:
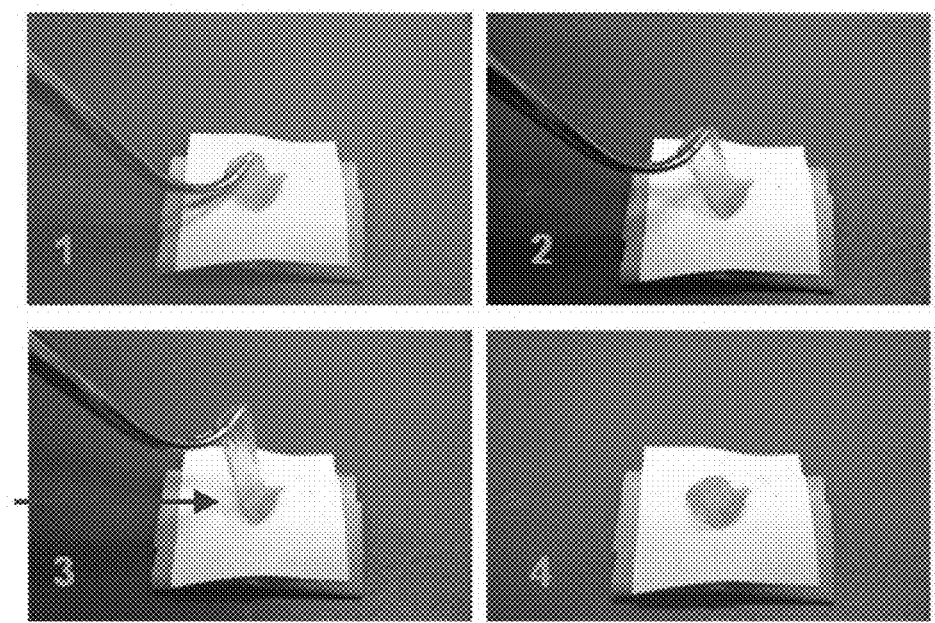
Figure 18:
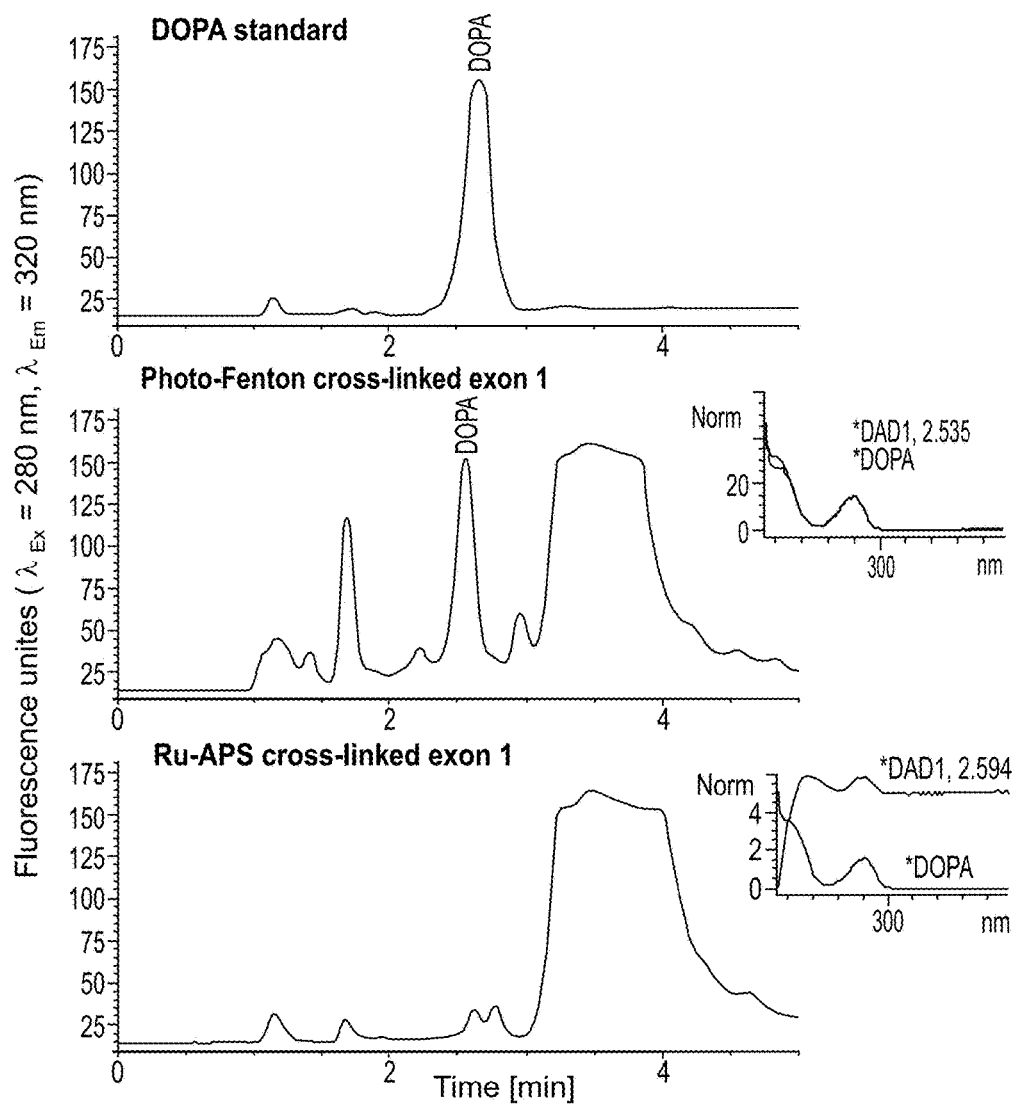
Figure 19:
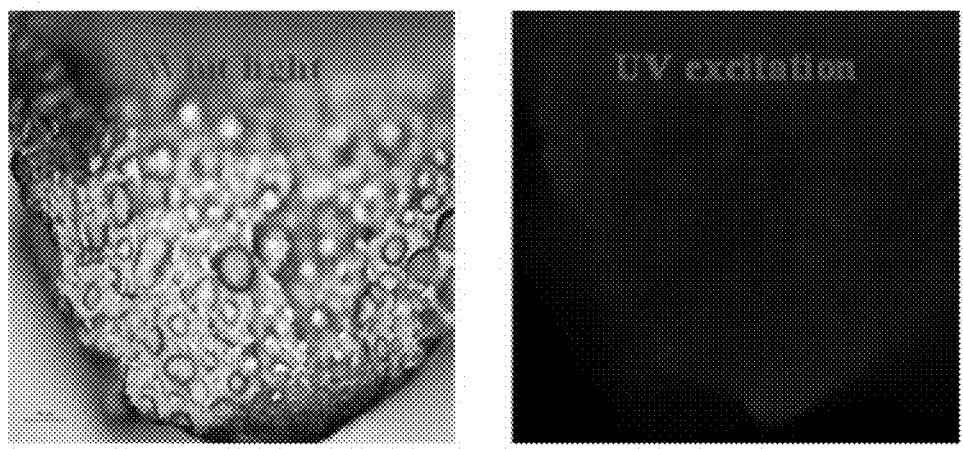
Figure 20:
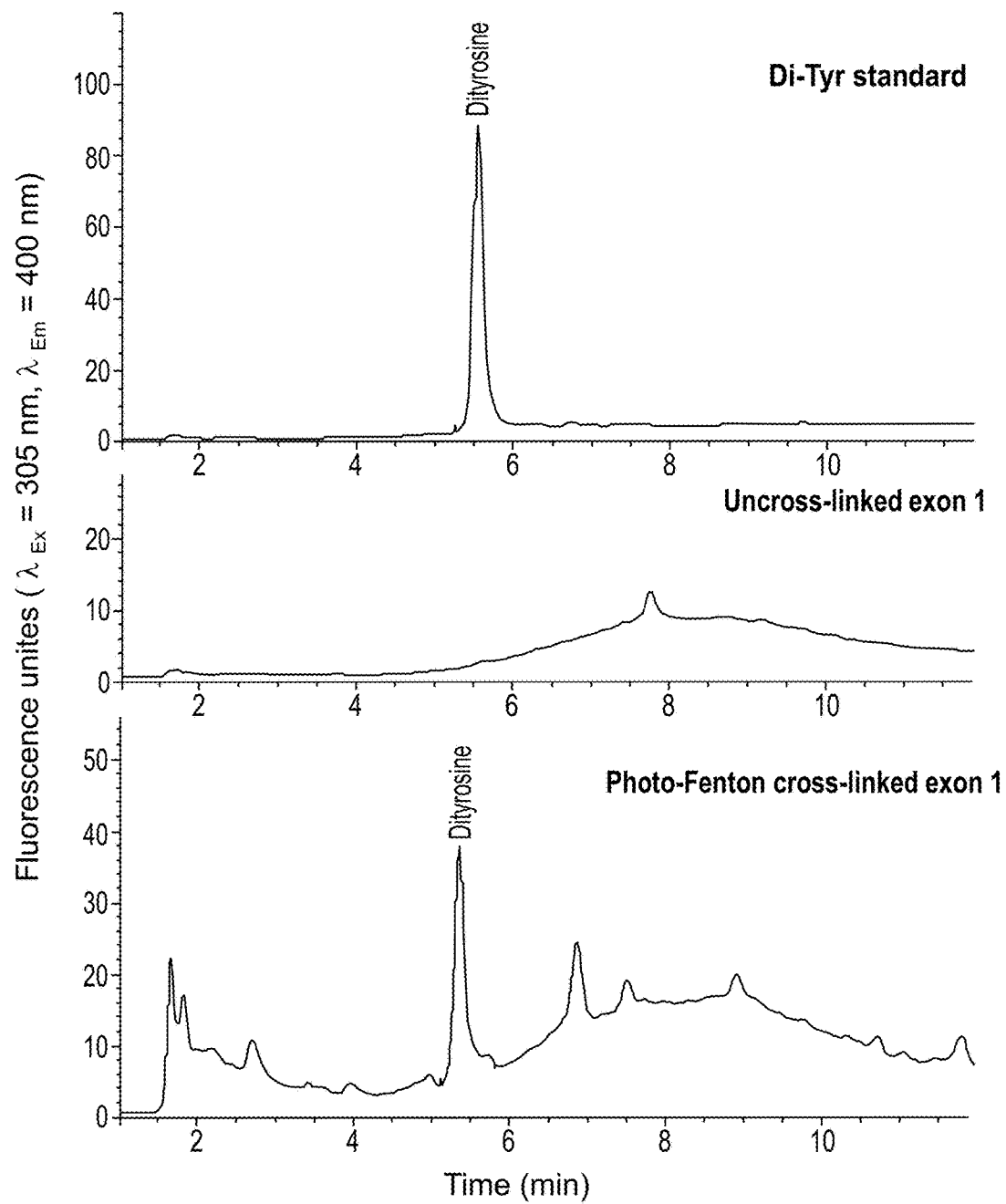
Figure 21:
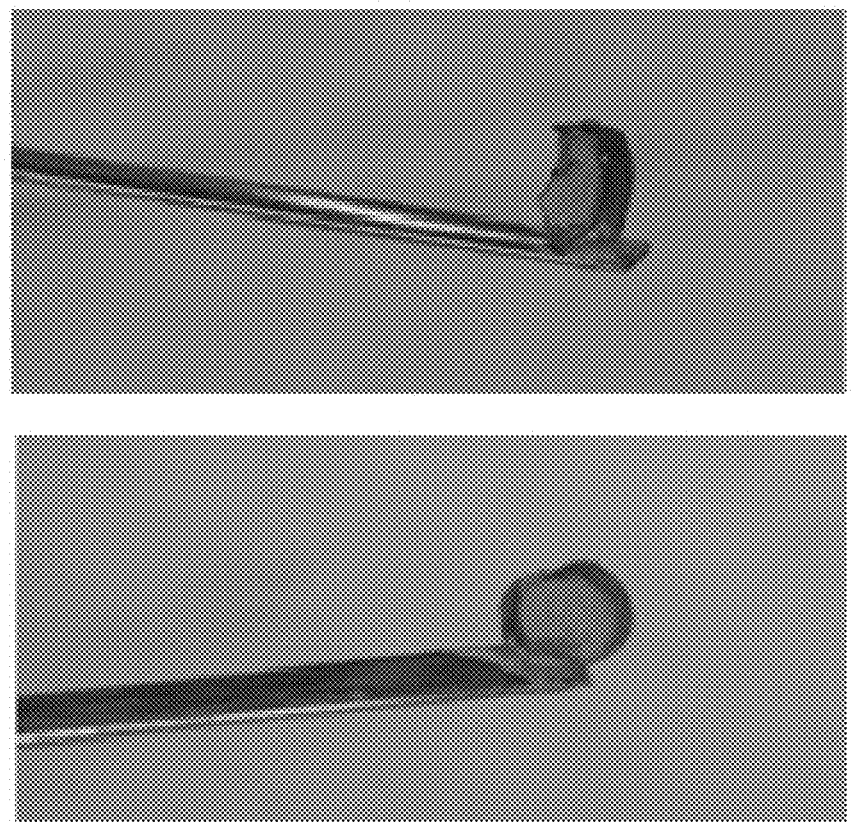

FIG. 1 presents an amino acid sequence of *Drosophila* gene product CG15920 after cleavage of the signal peptide, showing regions corresponding to exon 1 (italics), exon 2 (bold) and exon 3 (underline) of native resilin (SEQ ID NO: 24);

FIG. 2 presents an exemplary DNA sequence (SEQ ID NO: 11) and protein sequence (SEQ ID NO: 12) of 6H-tagged resilin (exon 1), showing a His tag (underline), a spacer (wavy underline), a TEV protease cleavage sequence (double underline; cleavage site is between the gray QG), amino acids added from the cloning process (dashed underline), and native resilin linker (bold underline);

FIG. 3 presents an exemplary DNA sequence (SEQ ID NO: 13) and protein sequence (SEQ ID NO: 14) of 6H-tagged resilin (exons 1 and 2), showing a His tag (underline), a spacer (wavy underline), a TEV protease cleavage sequence (double underline; cleavage site is between the gray QG), amino acids added from the cloning process (dashed underline), native resilin linker (bold underline), and chitin-binding domain (exon 2; bold italics);

FIG. 4 presents an exemplary DNA sequence (SEQ ID NO: 15) and protein sequence (SEQ ID NO: 16) of 6H-tagged resilin (exon 1) fused to a cellulose-binding domain (CBD), showing a His tag (underline), a spacer (wavy underline), a TEV protease cleavage sequence (double underline; cleavage site is between the gray QG), amino acids added from the cloning process (dashed underline), native resilin linker (bold underline) and cellulose-binding domain (bold wavy underline);

FIG. 5 presents an exemplary DNA sequence (SEQ ID NO: 17) and protein sequence (SEQ ID NO: 18) of 6H-tagged resilin (exon 1) fused to a cellulose-binding domain (CBD), showing a His tag (underline), a spacer (wavy underline), a TEV protease cleavage sequence (double underline; cleavage site is between the gray QG), native resilin linker (bold underline) and cellulose-binding domain (bold wavy underline);

FIG. 6 is a graph showing a stress-strain curve upon compression of two samples (gel 1 and gel 2) of an exemplary resilin derivative (D.17res) treated with 15 mM or 30 mM periodic acid (some of the cured resilin derivatives were swelled upon immersion in double distilled water (DDW);

FIG. 7 is an image showing four samples of two collagen membranes glued together (in area indicated for one sample by dotted line) with an exemplary dopylated resilin treated with 30 mM periodic acid, as well as the direction of extension forces (indicated by yellow arrows) to which the glued membranes were subjected during testing;

FIG. 8 is a graph showing stress-strain curves upon extension of each of the four samples of glued collagen membranes shown in FIG. 7;

FIGS. 9A and 9B are images showing a collagen membrane glued to a porcine artery with an exemplary dopylated resilin treated with 30 mM periodic acid, before (FIG. 9A) and after (FIG. 9B) extension of the membrane by tweezers (direction of extension forces indicated by arrows);

FIGS. 10A-10C are images showing a collagen sponge (held by tweezers) crown coated with an exemplary dopylated resilin, a sodium periodate solution for activating the dopylated resilin (FIGS. 10A and 10B; liquid in Petri dish), activation of the dopylated resilin by contacting collagen sponge with the periodate solution (FIG. 10B; orange solution is formed upon activation), and subsequent placement of the collagen sponge in a sheep knee defect (FIG. 10C);

FIG. 11 is an image showing a collagen sponge glued to a sheep knee defect with an exemplary dopylated resilin treated with 25 mM periodic acid, and withstanding an extension force applied by tweezers (direction of extension force indicated by arrow);

FIG. 12 is a graph showing stress-strain (elongation) curves upon extension of three collagen sponges glued to sheep knee defects as shown in FIG. 10A to FIG. 11;

FIGS. 13A and 13B present a graph showing absorption at various times following incubation of an exemplary dopylated resilin with sodium periodate (FIG. 13A), and a scheme (FIG. 13B) describing a possible mechanism explaining the changes in absorption over time; dopamine quinone (1) concentrations decrease and crosslinked dopamine (3) concentrations increases as dopamine quinone is converted to a radical (2) which forms crosslinked dopamine (3), while some dopamine quinone is converted to α,β-dehydrodopamine;

FIG. 14 is a graph showing a concentration of DOPA residues in an exemplary sample of a resilin derivative (diamonds), as determined by a colorimetric assay, as well as the calculated percentage of tyrosine residues converted to DOPA residues (squares) (resilin concentration in assay is 30 μg/ml);

FIG. 15 presents images showing UV illumination of unmodified resilin in the presence of $FeSO_4$ and $H_2O_2$ (left panel) and subsequent removal of the cured resilin derivative (right panel);

FIG. 16 presents images showing the high elasticity of an exemplary crosslinked resilin derivative under compression (time sequence of panels is indicated by numbers);

FIG. 17 presents images showing the high elasticity of an exemplary crosslinked resilin derivative under extension via tweezers, as well as the strong adhesion of the resilin derivative to the underlying cellulose sheet (emphasized by arrow) (time sequence of panels is indicated by numbers);

FIG. 18 presents graphs showing amino acid analysis by HPLC of exemplary photo-Fenton crosslinked resilin according to some embodiments of the invention, Ru-APS crosslinked resilin, and a DOPA standard, following separation of acid hydrolyzed resilin samples on a C-18 reverse phase column (detection via fluorescence measurement);

FIG. 19 presents photomicrographs showing an exemplary photo-Fenton crosslinked resilin under illumination by white light (left panel) and UV light (right panel);

FIG. 20 presents graphs showing amino acid analysis by HPLC of exemplary photo-Fenton crosslinked resilin according to some embodiments of the invention, non-crosslinked resilin and a di-tyrosine (Di-Tyr) standard, following separation of acid hydrolyzed resilin samples on a C-18 reverse phase column (detection via fluorescence measurement); and FIG. 21 presents images showing samples of a control polymer prepared by reacting resilin with sodium periodate.

DESCRIPTION OF SPECIFIC EMBODIMENTS
OF THE INVENTION

The present invention, in some embodiments thereof, relates to adhesive biopolymers and uses thereof.

While studying the properties of biopolymers, the present inventors have uncovered that introduction of dihydroxyphenyl moieties to biopolymers results in considerable adhesive properties. The inventors have envisioned and demonstrated novel methods for preparing modified biopolymers comprising dihydroxyphenyl moieties and further shown that such modified biopolymers can serve as highly effective adhesives.

The use of biopolymers results in adhesives properties, which allows for their use in a variety of medical applications.

In addition, certain biopolymers (e.g., resilin) may be selected so as to exhibit highly elastic and resilient properties. The combination of strong adhesiveness and high elasticity and resilience is highly advantageous for a variety of applications, for example, use as a sealant or binder of organic and inorganic surfaces or surfaces.

According to an aspect of some embodiments of the invention, there is provided a polymer having a dihydroxyphenyl moiety. The polymer optionally has the general formula I:

$$A\text{-}L\text{-}B \qquad \text{Formula I}$$

wherein:
B is a biopolymer;
L is a linking moiety; and
A is a dihydroxyphenyl moiety having the general formula II:

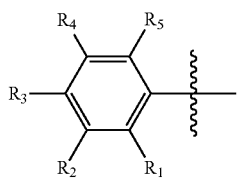

Formula II wherein each of $R_1$-$R_5$ is independently selected from the group consisting of hydrogen, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, and at least two of $R_1$-$R_5$ are hydroxy. It is to be understood that moieties comprising more than two hydroxy groups are herein encompassed by the term "dihydroxyphenyl".

As used herein, the term "biopolymer" refers to a biomolecule that includes at least two monomer units attached to one another. A "biomolecule" refers to an organic molecule that is of biological origin. It will be appreciated that the biopolymer does not have to be limited to one found in nature, but may also be a derivative or portion thereof. Exemplary biomolecules include nucleic acids, nucleotides, amino acids, polypeptides (e.g. recombinant polypeptides), peptides, peptide fragments, polysaccharides (sugars), fatty acids, steroids, lipids, and combinations of these biomolecules (e.g., glycoproteins, ribonucleoproteins, or lipoproteins).

According to a specific embodiment, the biopolymer is not a polypeptide.

According to another embodiment, the biopolymer is not collagen or resilin.

According to one embodiment, the biopolymer is a polycarboxylate, including glutamic and aspartic acids-based proteins (e.g. collagen, silks, elastin, resilin) and corresponding synthetic copolymers. According to another embodiment, the biopolymer is a glycosaminoglycan (e.g. hyaluronan, heparin, heparin sulfate, dermatan sulfate) or a carboxylate-containing polysaccharide (e.g. carboxymethyl cellulose (CMC) and other oxidized polysaccharides.

According to one embodiment, the biopolymer is not a component of a polysaccharide/fibrous polypeptide composite, such as those described in International Patent Application PCT/IL2008/001542 (published as WO 2009/069123), the contents of which are incorporated herein by reference.

The above Formula I is not intended to suggest that only one dihydroxyphenyl moiety (and linking moiety) is attached to each biopolymer moiety. A plurality (e.g., at least two) of a dihydroxyphenyl moiety (and linking moiety) described herein may optionally be attached to each biopolymer moiety. When a plurality of dihydroxyphenyl moieties and linking moieties are attached to a biopolymer, the dihydroxyphenyl moieties and linking moieties may be the same or different from one another.

In some embodiments, the polymer comprises from 3 to 15 dihydroxyphenyl moieties (on average) per biopolymer moiety, and optionally from 4 to 10 dihydroxyphenyl moieties per biopolymer moiety.

Optionally, the polymer comprises a single species of biopolymer (e.g., a single species of polypeptide, a single species of polysaccharide).

Optionally, the biopolymer is a crosslinked biopolymer. Alternatively, the biopolymer is substantially non-crosslinked.

In some embodiments, the dihydroxyphenyl moiety comprises a hydroxy group at a para position (with respect to the linking moiety), i.e., $R_3$ is hydroxy.

In some embodiments, the dihydroxyphenyl moiety comprises at least one hydroxy group at a meta position (with respect to the linking moiety), i.e., $R_2$ is hydroxy. One of skill in the art will appreciate that $R_2$ and $R_4$ are equivalent positions on the phenyl ring, and that the description herein of a hydroxy group at a meta position as being $R_2$ rather than $R_4$ is for convenience and does not affect the scope of the claim. Optionally, both $R_2$ and $R_4$ are hydroxy.

In some embodiments, the dihydroxyphenyl moiety comprises both a hydroxy group at a para position and a hydroxy group at a meta position (with respect to the linking moiety), i.e., $R_2$ and $R_3$ are each hydroxy. In some embodiments, only $R_2$ and $R_3$ are hydroxy.

In some embodiments, the phenyl ring comprises at least one non-substituted position, such that at least one of $R_1$-$R_5$ is hydrogen.

Optionally, each position not substituted by a hydroxy group is a non-substituted position. For example, in some embodiments wherein $R_2$ and $R_3$ are hydrogen, $R_1$, $R_4$ and $R_5$ are each hydrogen.

Without being bound by any specific theory, it is believed that a presence of a non-substituted position facilitates convenient crosslinking of the dihydroxyphenyl moieties, and the ability of dihydroxyphenyl moiety-containing polymers described herein to undergo crosslinking provides the polymers with advantageous properties such as described herein.

As mentioned herein above, the biopolymer may be a polypeptide.

Typically, the polypeptide is one which comprises amino acids which comprise hydroxyphenyl moieties—e.g. tyrosine.

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to N' terminus modification, C' terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modifications, D configuration stereoisomers of peptides or proteins, Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylene bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acids such as phenylglycine, 1,2,3,4-tetrahydroisoquinoline-3-carboxylic acid (TIC), naphthylelanine (Nol), ring-methylated derivatives of Phe, halogenated derivatives of Phe or o-methyl-Tyr.

As mentioned, the amino acid sequences of contemplated polypeptides may either be the amino acid sequences of the polypeptides in naturally-occurring proteins or those that comprise either conservative or non-conservative substitutions.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered conservative substitutions.

For producing conservative substitutions by non-naturally occurring amino acids it is also possible to use amino acid analogs (synthetic amino acids) well known in the art. A peptidomimetic of the naturally occurring amino acids is well documented in the literature known to the skilled practitioner.

When effecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CH[(—CH$_2$)$_5$—COOH]—CO— for aspartic acid. Those non-conservative substitutions which fall within the scope of the present invention are those which still constitute a polypeptide being able to form a fibrous protein.

As used herein in the specification and in the claims section below, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-ethylcyclohexylalanine | Mchexa |
| D-α-methylarginine | Dmarg | α-ethylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |

TABLE 2-continued

| Non-conventional amino acid | Code | Non-conventional amino acid | Code |
|---|---|---|---|
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-naphthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-ethylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalanine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethy)glycine | Nthr |
| D-N-methylhistidine | Dnmhis | N-(hydroxyethy)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylamino-isobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α ethylvaline | Mtrp | L-N-methyltyrosine | Mtyr |
| L-α-methylleucine | Mval | L-N-methylhomophenylalanine | Nmhphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenylethylamino)cyclopropane | Nmbc | | |

Recombinant techniques may be used to generate the polypeptides of the present invention since these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce a polypeptide of the present invention using recombinant technology, a polynucleotide encoding a polypeptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

A variety of prokaryotic or eukaryotic cells as well as cell free protein expression systems such as wheat germ and E. coli systems can be used as host-expression systems to express the polypeptides of the present invention. These include, but are not limited to, microorganisms, such as bacteria (for example, E. coli including but not limited to E. coli strains BL21 (DE3) plysS, BL21; (DE3)RP and BL21* and B. subtilis) transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

Various methods can be used to introduce the expression vector of the present invention into the cells of the host expression system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

According to a particular embodiment, the polypeptide comprises a resilin amino acid sequence.

GenBank Accession Nos. of non-limiting examples of resilin are listed in Table 3 below. A resilin of the present invention also refers to homologs (e.g. polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to resilin sequences listed in Table 3 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Table 3 below lists examples of resilin NCBI sequence numbers.

TABLE 3

| Exemplary resilin NCBI sequence number | Organism |
| --- | --- |
| NP 995860 | *Drosophila melanogaster* |
| NP 611157 | *Drosophila melanogaster* |
| Q9V7U0 | *Drosophila melanogaster* |
| AAS64829 | *Drosophila melanogaster* |
| AAF57953 | *Drosophila melanogaster* |
| XP 001817028 | *Tribolium castaneum* |
| XP001947408 | *Acyrthosiphon pisum* |

According to one embodiment, the resilin amino acid sequence comprises the full length resilin amino acid sequence (i.e. comprises amino acids from each of exon 1, exon 2 and exon 3—see FIG. 1—SEQ ID NO: 24).

According to another embodiment, the resilin amino acid sequence comprises an exon 1 resilin amino acid sequence (SEQ ID NOs: 1, 2 or 19). The resilin amino acid sequence may be 70% homologous, 75% homologous, 80% homologous, 85% homologous, 90% homologous, 91% homologous, 92% homologous, 93% homologous, 94% homologous, 95% homologous, 96% homologous, 97% homologous, 98% homologous, 99% homologous or 100% homologous to the sequence as set forth in SEQ ID NOs: 1, 2 or 19 as determined using BlastP software of the National Center of Biotechnology Information (NCBI) using default parameters. The homolog may also refer to a deletion, insertion, or substitution variant, including an amino acid substitution, thereof and biologically active polypeptide fragments thereof.

Alternatively, the resilin amino acid sequence comprises an exon 1 resilin amino acid sequence and a polysaccharide binding domain (e.g. a cellulose binding domain (CBD) and/or a chitin binding domain (ChBD), such as that encoded in exon 2).

An exemplary ChBD binding sequence found in exon 2 of resilin is provided in SEQ ID NO: 3 or 6.

Exemplary cellulose binding domain amino acid sequences are provided in SEQ ID NOs: 20 and 22. Additional polysaccharide binding domains are provided in WO2009/069123, incorporated herein by reference.

The polysaccharide binding domain may be linked to the C terminal domain of exon 1 or the N terminal domain of exon 1 (either directly or via a linker).

Exemplary amino acid sequences or exon 1 resilin amino acid sequences linked to chitin binding domains or cellulose binding domains are provided in FIGS. 2-5.

According to still another embodiment, the resilin amino acid sequence comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen or more resilin repeating unit as set forth in SEQ ID NO: 4 (Gly Gly Arg Pro Ser Asp Ser Tyr Gly Ala Pro Gly Gly Gly Asn).

According to still another embodiment the resilin amino acid sequence comprises at least one, at least two, at least three, at least four, at least five, at least six, at least seven, at least eight, at least nine, at least ten, at least eleven, at least twelve, at least thirteen, at least fourteen, at least fifteen, at least sixteen, at least seventeen or more resilin repeating unit as set forth in SEQ ID NO: 5 (GRPSDSYGA).

According to still another embodiment the resilin amino acid sequence is devoid of exon 3 amino acid sequence.

According to yet another embodiment, the resilin amino acid sequence comprises the exon 3 amino acid sequence.

Examples of polynucleotides which can be used to express resilin are set forth in SEQ ID NO: 7, 11, 13, 15 and 17.

Other exemplary polypeptide and polynucleotide sequences that may be used are provided in International Application No. WO 2009/069123, incorporated herein by reference and in the enclosed Appendix.

Polynucleotides of the present invention may be prepared using PCR techniques as described in the Examples section below, can be chemically synthesized or by any other method or procedure known in the art for ligation of two different DNA sequences. See, for example, "Current Protocols in Molecular Biology", eds. Ausubel et al., John Wiley & Sons, 1992.

Polypeptides of the present invention can be purified using a variety of standard protein purification techniques, such as, but not limited to, heat treatments, salting out for example with ammonium sulfate, polyethyleneimines (PEI) precipitation, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety e.g. histidine. Such a fusion protein can be designed so that the polypeptide can be readily isolated by affinity chromatography; e.g., by immobilization on a column specific for the cleavable moiety (see Examples section, herein below).

Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in a "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Following expression and optional purification of the polypeptides of the present invention, the polypeptides may be polymerized to form an insoluble material from a solution, preferably one with a relatively high concentration of polypeptide. According to one embodiment, the critical concentration of a resilin polypeptide of the present invention is about 50 mg/ml. According to one embodiment, the polypeptide is concentrated by ultracentrifugation.

The dihydroxyphenyl moiety of the above Formula II is a non-crosslinked moiety, that is, they are attached to a biopolymer only at one position (via the linking moiety). However, the polymer having the formula I may optionally further comprise one or more crosslinked dihydroxyphenyl moieties.

Herein, a "crosslinked dihydroxyphenyl moiety" refers to a dihydroxyphenyl moiety attached to a biopolymer (directly or via a linking moiety) at two positions of the phenyl ring thereof. The crosslinking may be between two biopolymer molecules (optionally identical polymer molecules) and/or between different sites on a single biopolymer molecule. A crosslinked dihydroxyphenyl moiety may be crosslinked to another dihydroxyphenyl moiety (an identical dihydroxyphenyl moiety and/or a different dihydroxyphenyl moiety), to a different moiety (e.g., a hydroxyphenyl moiety), or crosslink directly to a biopolymer.

According to some embodiments, the polymer is substantially devoid of crosslinking by the dihydroxyphenyl moiety.

As used herein, the term "substantially devoid of crosslinking" means that at least 90%, optionally at least 99%, and optionally at least 99.9% of the total amount of dihydroxyphenyl moieties of the polymer are not crosslinked.

According to optional embodiments, a dihydroxyphenyl moiety and a linking moiety may form a part of the biopolymer (e.g., part of a monomer residue of the biopolymer), optionally by modification of a naturally existing form of the biopolymer. Thus, for example, the dihydroxyphenyl moiety and linking moiety may together form a side chain of the biopolymer, the linking moiety being attached to the backbone of the biopolymer.

In exemplary embodiments, the dihydroxyphenyl moiety and the linking moiety form a part of a DOPA (i.e., 3,4-dihydroxyphenylalanine) residue, for example, a DOPA residue side chain, wherein the dihydroxyphenyl is 3,4-dihydroxyphenyl, and the linking moiety is $CH_2$. Optionally, the DOPA is L-DOPA.

According to another embodiment, the dihydroxyphenyl moiety is not DOPA.

In alternative embodiments, the dihydroxyphenyl moiety and linking moiety do not form a part of a DOPA residue, that is, the dihydroxyphenyl is not 3,4-dihydroxyphenyl and/or the linking moiety is not $CH_2$, and/or the linking moiety is not attached to the backbone of a peptide residue. Optionally, the dihydroxyphenyl moiety and linking moiety do not form a DOPA side chain, that is the dihydroxyphenyl is not 3,4-dihydroxyphenyl and/or the linking moiety is not $CH_2$.

According to some embodiments, the linking moiety is attached to a side chain of the biopolymer rather than to the backbone thereof. Thus, the linking moiety may optionally be conjugated to a naturally occurring side chain of the biopolymer. Alternatively or additionally, the linking moiety may optionally be conjugated to a side chain which is a modification of a naturally occurring side chain of the biopolymer.

Optionally, linking moiety is attached to the biopolymer via a covalent bond (e.g., an amide bond, an amine bond, a thioether bond) formed between a reactive group in the linking moiety and a functional group on the biopolymer.

Thus, for example, an amine functional group on the biopolymer (e.g., an amine of a lysine residue) may be attached via an amide bond to a reactive group which is a carboxylic acid or an activated derivative thereof. Activated carboxylic acid groups (e.g., N-hydroxysuccinimide esters) are known in the art.

Similarly, a carboxylic acid functional group on the biopolymer (e.g., a carboxylic acid of a glutamate or aspartate residue) may be attached via an amide bond to a reactive group which is an amine. The carboxylic acid may optionally be converted to an activated carboxylic acid group in order to facilitate reaction with the amine group.

An amine functional group on the biopolymer (e.g., an amine of a lysine residue) may be attached via an amine bond to a suitable reactive group. A non-limiting example of a suitable reactive group is maleimide, which may react with an amine via Michael addition to generate a succinimide group attached via an amine bond.

A thiohydroxy functional group on the biopolymer (e.g., a thiohydroxy of a cysteine residue) may be attached via a thioether bond to a suitable reactive group. A non-limiting example of a suitable reactive group is maleimide, which may react with a thiohydroxy via Michael addition to generate a succinimide group attached via a thioether bond.

In some embodiments, the reactive group is a leaving group (e.g., halide, sulfate) which is substituted by the functional group of the biopolymer, such that the reactive group is absent from the linking group after being covalently bound to the biopolymer. For example an amine or thiohydroxy group of the biopolymer (e.g., a lysine amine, a cysteine thiohydroxy) may replace a leaving group (e.g., by nucleophilic substitution), resulting in an amine bond or thioether bond.

Additional contemplated functional groups include hydrazine and hydrazide.

Additional techniques for forming covalent bonds (e.g., amide, amine and thioether bonds) will be known to those skilled in the chemical arts.

Optionally, the linking moiety comprises a hydrocarbon chain linking the reactive group to the dihydroxyphenyl moiety. The hydrocarbon chain may be saturated or unsaturated, and substituted or non-substituted. In some embodiments, the hydrocarbon chain is saturated. In some embodiments, the hydrocarbon chain is non-substituted. Examples of suitable hydrocarbon chains include $CH_2$, $CH_2CH_2$, $CH_2CH_2CH_2$, $CH_2CH_2CH_2CH_2$, and $CH_2CH_2CH_2CH_2CH_2$.

As used herein, the phrase "hydrocarbon chain" and the term "hydrocarbon" describes a moiety that is mainly composed of carbon and hydrogen atoms. A hydrocarbon chain can therefore include one or more of alkyl, alkenyl, alkynyl, cycloalkyl and aryl, as these terms are defined herein, whereby each can be unsubstituted or substituted, as described herein. Optionally, the hydrocarbon chain can further be interrupted by one or more heteroatoms, as defined herein. Alternatively, the hydrocarbon chain comprises an uninterrupted chain of carbon atoms from the A moiety to the B moiety (although heteroatoms may optionally be present in a substituent of the hydrocarbon chain).

It will be appreciated by one of skills in the art that the feasibility of each of the substituents and moieties described herein (e.g., $R_1$-$R_5$ and L) to be located at the indicated positions depends on the valence and chemical compatibility of the substituent or moiety, the substituted position and other substituents. Hence, the present invention is aimed at encompassing all the feasible substituents and moieties for any position.

Thus, for example, $R_1$-$R_5$ may be end groups (e.g., any end groups described herein).

Herein throughout, the phrase "end group" describes a group (a substituent) that is attached to another moiety in the compound via one atom thereof.

In addition, the linking moieties described herein (e.g., the variable L) comprise a linking group, or a plurality of linking groups attached to one another (e.g., any linking groups described herein). Optionally, one or more of $R_1$-$R_5$ (preferably only $R_1$ and/or $R_5$) is a linking group, being attached to both the A moiety and to the linking moiety L, thereby forming a ring.

The phrase "linking group" herein describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, oxo, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino.

The alkyl group can be an end group, as this phrase is defined hereinabove, wherein it is attached to a single adjacent atom, or a linking group, as this phrase is defined hereinabove, which connects two or more moieties via at least two carbons in its chain.

The term "alkenyl" describes an alkyl group, as defined hereinabove, except that it consists of at least two carbon atoms and comprises at least one carbon-carbon double bond.

The term "alkynyl" describes an alkyl group, as defined hereinabove, except that it consists of at least two carbon atoms and comprises at least one carbon-carbon triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, oxo, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, oxo, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, oxo, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofuran, tetrahydropyran, morpholine and the like.

As used herein, the terms "amine" and "amino" describe both a —NRxRy group and a —NRx- group, wherein Rx and Ry are each independently hydrogen, alkyl, cycloalkyl, aryl, heteroaryl or heteroalicyclic (wherein the amine nitrogen atom is bound to a carbon atom of Rx and Ry), as these terms are defined herein.

The amine group can therefore be a primary amine, where both Rx and Ry are hydrogen, a secondary amine, where Rx is hydrogen and Ry is alkyl, cycloalkyl, aryl, heteroaryl or heteroalicyclic, or a tertiary amine, where each of R' and R" is independently alkyl, cycloalkyl, aryl, heteroaryl or heteroalicyclic.

The term "halide" and "halo" describes fluorine, chlorine, bromine or iodine.

The term "sulfate" describes a —O—S(=O)$_2$—ORx end group, as this term is defined hereinabove, or an —O—S(=O)$_2$—O— linking group, as these phrases are defined hereinabove, where $R_X$ is as defined hereinabove.

The term "thiosulfate" describes a —O—S(=S)(=O)—ORx end group or a —O—S(=S)(=O)—O— linking group, as these phrases are defined hereinabove, where Rx is as defined hereinabove.

The term "sulfite" describes an —O—S(=O)—O—Rx end group or a —O—S(=O)—O— group linking group, as these phrases are defined hereinabove, where $R_X$ is as defined hereinabove.

The term "thiosulfite" describes a —O—S(=S)—O—Rx end group or an —O—S(=S)—O— group linking group, as these phrases are defined hereinabove, where $R_X$ is as defined hereinabove.

The term "sulfinate" describes a —S(=O)—ORx end group or an —S(=O)—O— group linking group, as these phrases are defined hereinabove, where $R_X$ is as defined hereinabove.

The term "sulfoxide" or "sulfinyl" describes a —S(=O)—Rx end group or an —S(=O)— linking group, as these phrases are defined hereinabove, where Rx is as defined hereinabove.

The term "sulfonate" or "sulfonyl" describes a —S(=O)$_2$—Rx end group or an —S(=O)$_2$— linking group, as these phrases are defined hereinabove, where Rx is as defined herein.

The term "sulfonamido", as used herein, encompasses both S-sulfonamides and N-sulfonamides.

The term "S-sulfonamide" describes a —S(=O)$_2$—NRxRy end group or a —S(=O)$_2$—NRx- linking group, as these phrases are defined hereinabove, with Rx and Ry as defined herein.

The term "N-sulfonamide" describes an RxS(=O)$_2$—NR$_Y$— end group or a —S(=O)$_2$—NRx- linking group, as these phrases are defined hereinabove, where Rx and Ry are as defined herein.

The term "disulfide" refers to a —S—S—Rx end group or a —S—S— linking group, as these phrases are defined hereinabove, where Rx is as defined herein.

The term "carbonyl" as used herein, describes a —C(=O)—Rx end group or a —C(=O)— linking group, as these phrases are defined hereinabove, with Rx as defined herein.

The term "thiocarbonyl" as used herein, describes a —C(=S)—Rx end group or a —C(=S)— linking group, as these phrases are defined hereinabove, with Rx as defined herein.

The term "oxo", as used herein, describes an =O end group.

The term "oxime" describes a =N—OH end group or a =N—O— linking group, as these phrases are defined hereinabove.

The terms "hydroxy" and "hydroxyl" describe a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "ether" describes groups or covalent bonds in which a carbon atom in an alkyl, cycloalkyl, aryl or heteroaryl is attached to an alkoxy or aryloxy group.

The term "thioether" describes groups or covalent bonds in which a carbon atom in an alkyl, cycloalkyl, aryl or heteroaryl is attached to a thioalkoxy or thioaryloxy group.

The terms "cyano" and "nitrile" describe a —C≡N group.

The term "isonitrile" describes a —N≡C group.

The term "isocyanate" describes an —N=C=O group.

The term "nitro" describes an —NO$_2$ group.

The term "azo" or "diazo" describes an —N=NR' end group or an —N=N— linking group, as these phrases are defined hereinabove, with R' as defined hereinabove.

The term "peroxo" describes an —O—ORx end group or an —O—O— linking group, as these phrases are defined hereinabove, with Rx as defined hereinabove.

The term "carboxy", as used herein, encompasses both C-carboxy and O-carboxy groups.

The term "C-carboxy" describes a —C(=O)—ORx end group or a —C(=O)—O— linking group, as these phrases are defined hereinabove, where Rx is as defined herein.

The term "O-carboxy" describes a —OC(=O)—Rx end group or a —OC(=O)— linking group, as these phrases are defined hereinabove, where R' is as defined herein.

The term "carboxylic acid" refers to a —C(=O)OH group.

The term "thiocarboxy", as used herein, encompasses both C-thiocarboxy and O-thiocarboxy groups.

The term "C-thiocarboxy" describes a —C(=S)—ORx end group or a —C(=S)—O— linking group, as these phrases are defined hereinabove, where Rx is as defined herein.

The term "O-thiocarboxy" describes a —OC(=S) Rx end group or a —OC(=S)— linking group, as these phrases are defined hereinabove, where Rx is as defined herein.

The term "urea" describes a —NRxC(=O)—NRyRw end group or a —NR$_X$C(=O)—NR$_Y$— linking group, as these phrases are defined hereinabove, where Rx and Ry are as defined herein and Rw is as defined herein for $R_X$ and Ry.

The term "thiourea" describes a —NRx-C(=S)—NRyRw end group or a —NRx-C(=S)—NRy- linking group, with Rx, Ry and Rw as defined herein.

The terms "amide" and "amido", as used herein, encompasses both C-amido and N-amido.

The term "C-amido" describes a —C(=O)—NRxRy end group or a —C(=O)—NRx- linking group, as these phrases are defined hereinabove, where Rx and Ry are as defined herein.

The term "N-amido" describes a RxC(=O)—NRy- end group or a RxC(=O)—N— linking group, as these phrases are defined hereinabove, where Rx and Ry are as defined herein.

The term "amide bond" refers to a bond between the nitrogen atom and the C=O moiety of an amide group, as defined herein.

The term "carbamyl" or "carbamate", as used herein, encompasses both N-carbamyl and O-carbamyl.

The term "N-carbamyl" describes an RyOC(=O)—NRx- end group or a —OC(=O)—NRx- linking group, as these phrases are defined hereinabove, with Rx and Ry as defined herein.

The term "O-carbamyl" describes an —OC(=O)—NRxRy end group or an —OC(=O)—NRx- linking group, as these phrases are defined hereinabove, with Rx and Ry as defined herein.

The term "thiocarbamyl" or "thiocarbamate", as used herein, encompasses both O-thiocarbamyl and N-thiocarbamyl.

The term "O-thiocarbamyl" describes a —OC(=S)—NRxRy end group or a —OC(=S)—NRx- linking group, as these phrases are defined hereinabove, with Rx and Ry as defined herein.

The term "N-thiocarbamyl" describes an RyOC(=S)NRx- end group or a —OC(=S)NRx- linking group, as these phrases are defined hereinabove, with Rx and Ry as defined herein.

The density of dihydroxyphenyl moieties on the polymer is optionally such that the polymer is characterized by a ratio of molecular weight to dihydroxyphenyl moieties in a range of from 1 KDa per dihydroxyphenyl moiety to 18 KDa per dihydroxyphenyl moiety, optionally from 1.5 KDa to 12 KDa, optionally from 2.5 KDa to 8 KDa, and optionally from 3 KDa to 6 KDa.

In embodiments wherein the biopolymer is a polypeptide, wherein some amino acid residues in the polypeptide comprise a dihydroxyphenyl moiety (e.g., DOPA residues) the density of dihydroxyphenyl moieties on the polymer is such that a percentage of amino acid residues of the polypeptide which comprise the dihydroxyphenyl moiety is in a range of from 0.5% to 5%, optionally from 1% to 3%.

In embodiments wherein the biopolymer is a polypeptide comprising DOPA residues, the number of DOPA residues is optionally at least 20% the number of tyrosine residues in the polypeptide, such that a ratio of a number of DOPA residues to a number of tyrosine residues in the polypeptide is at least 1:5, optionally at least 1:3, optionally at least 1:1.5, and optionally at least 1:1.

As exemplified herein, polymers described hereinabove may be particularly effective as adhesives.

Optionally, the polymer does not exhibit substantial adhesiveness per se, but upon crosslinking of the polymer (e.g., crosslinking of dihydroxyphenyl moieties), the polymer becomes capable of adhering strongly to a surface.

Alternatively, the polymer exhibits substantial adhesiveness per se (i.e., the polymer is sticky). Optionally, the polymer exhibits an adhesiveness to a surface (e.g., a surface as described herein), such that the polymer adheres to the surface upon contact with the surface, wherein the adhesiveness is characterized by resistance to stress of 1 KPa (0.001 MPa) in a direction perpendicular to said surface, optionally resistance to at least 0.01 MPa, optionally resistance to at least 0.1 MPa, optionally resistance to at least 1 MPa, and optionally resistance to at least 10 MPa. Optionally, an adhesiveness of the polymer increases upon crosslinking of the polymer (e.g., crosslinking of dihydroxyphenyl moieties).

As exemplified herein, a polymer comprising dihydroxyphenyl moieties may be prepared by conjugating a dihydroxyphenyl-containing compound to a biopolymer.

Thus, according to another aspect of embodiments of the invention there is provided a method of preparing a polymer described herein, wherein the polymer comprises covalent bond formed between a reactive group in the linking moiety (e.g., a reactive group described herein) and a functional group on the biopolymer (e.g., a functional group described herein). The method comprises providing a compound comprising the dihydroxyphenyl moiety and the reactive group, and contacting the compound with a biopolymer comprising at least one functional group to form the covalent bond.

Optionally, the biopolymer is a polypeptide, optionally comprising at least one resilin amino acid sequence (e.g., as described herein).

As exemplified herein, a resilin amino acid sequence may provide the dihydroxyphenyl moiety-containing polymer, as well as crosslinked derivatives thereof, with considerable elasticity and resilience.

The structure of the compound to be reacted with the biopolymer will depend on the desired structure of the polymer being prepared.

Thus, for example, the compound may comprise any dihydroxyphenyl moiety described herein (e.g., corresponding to the variable A in Formula I), and any linking group and reactive group described herein (corresponding to the variable L in Formula I).

An exemplary compound is dopamine, which comprises a 3,4-hydroxyphenyl moiety attached via a $CH_2CH_2$ hydrocarbon chain to a reactive group which is an amine ($NH_2$).

According to exemplary embodiments, the amine group reacts with carboxylic acid groups of the biopolymer (e.g., glutamate and/or aspartate residues) to form amide bonds.

As exemplified herein, a polymer comprising dihydroxyphenyl moieties may also be prepared by modifying moieties of a biopolymer (e.g., hydroxyphenyl moieties) so as to form dihydroxyphenyl moieties.

Thus according to another aspect of embodiments of the invention, there is provided a method of preparing a polymer described herein, the method comprising providing a biopolymer comprising at least one hydroxyphenyl moiety, and oxidizing at least one of the at least one hydroxyphenyl moiety to form a dihydroxyphenyl moiety such as described herein.

Optionally, the biopolymer is a polypeptide, optionally comprising at least one resilin amino acid sequence (e.g., as described herein).

In some embodiments, the hydroxyphenyl moiety is comprised by a tyrosine residue in the biopolymer, e.g., wherein the biopolymer comprises a polypeptide. Optionally, oxidizing the tyrosine residue results in conversion of the tyrosine reside to a DOPA residue.

In some embodiments, oxidizing of the hydroxyphenyl moiety is effected using an enzyme, for example, by contacting the biopolymer with a tyrosine hydroxylase.

Herein, the term "tyrosine hydroxylase" encompasses any enzyme which hydroxylates tyrosine (e.g., L-tyrosine), including a tyrosine residue, to form DOPA (e.g., L-DOPA), or a DOPA residue. Examples of suitable tyrosine hydroxylases include, without limitation, tyrosinases, for example, mushroom tyrosinase (e.g., 1.14.18.1) and tyrosine 3-monooxygenase (e.g., EC number 1.14.16.2).

In some embodiments, oxidizing of the hydroxyphenyl moieties does not further induce substantial crosslinking of the resulting dihydroxyphenyl moieties, such that the obtained polymer comprising the dihydroxyphenyl moiety is substantially devoid (as this term is defined herein) of crosslinking by the dihydroxyphenyl moiety.

In some embodiments, use of an enzyme (e.g., as described herein) facilitates selective oxidation, wherein dihydroxyphenyl is formed without substantial crosslinking.

Many methods for generating reactive oxygen species (ROS) may result in significant toxicity, as oxidative stress caused by ROS exposure may lead to undesirable formation of protein fragments and/or carbonyl group, particularly in oxygen-rich environments.

Without being bound by any particular theory, it is believed that hydrogen abstraction from tyrosine via .OH generates radicals in hypoxic environments, which leads to cross-links such as described herein, and that .OH generating systems may therefore efficiently cross-link resilin, with relatively little detrimental side reactions.

Thus, according to optional embodiments, oxidizing is effected by an .OH generating system.

According to optional embodiments, oxidizing is effected by a Fenton reaction. The Fenton system is relatively non-toxic, and can serve as a biocompatible method for in situ/vivo polymerization.

Herein, the term "Fenton reaction" refers to a reaction of a metal ion with a peroxide (e.g., hydrogen peroxide, $H_2O_2$) which produces hydroxyl radicals (.OH). Preferably, the metal ion is capable of single electron reduction (i.e. loss of a single electron results in a different, but stable, oxidation state). Preferably, the metal ion is an iron-(II) ion (e.g., $Fe^{2+}$ or a complex thereof), which can readily lose one electron, resulting in an iron-(III) ion (e.g., $Fe^{3+}$ or a complex thereof). Alternatively the metal ion is an iron-(III) ion.

In a Fenton reaction, the metal ion typically reduces the peroxide to produce a hydroxyl radical.

In some embodiments, the metal ion (e.g., iron-(II)) can be regenerated, such that the metal ion serves as a catalyst. Consequently, only a small, catalytic amount of the metal ion is necessary.

Optionally, the Fenton reaction is induced by illumination (e.g., UV illumination). Illumination may regenerate the metal ion and/or produce additional hydroxyl radicals, thereby facilitating the Fenton reaction in the presence of a limited amount of the metal ion. For example, $Fe^{2+}$ reacts with $H_2O_2$ to produce .OH and $FeOH^{2+}$ complex, and illumination (e.g., UV illumination) converts $FeOH^{2+}$ complex to $Fe^{2+}$ and .OH, thereby both regenerating $Fe^{2+}$ and producing additional hydroxyl radicals.

In some embodiments, the Fenton system is characterized by one or both of the following reactions:

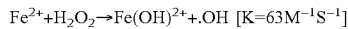  a)

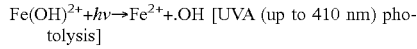  b)

In some embodiments, the Fenton reaction is performed in the presence of a chelator of the metal ion, e.g., a chelator of iron-(II). Optionally, the chelator is selected so as to prevent precipitation of the metal. Citrate is an exemplary chelator.

Without being bound by any particular theory, it is believed that a chelator is useful limiting the amount of available metal ions (e.g., $Fe^{2+}$) for reaction with $H_2O_2$, thereby controlling the rate of —OH production.

Thus, according to exemplary embodiments, the method comprises performing a Fenton reaction by contacting the biopolymer with iron-(II), hydrogen peroxide and citrate (e.g., at concentrations and/or concentration ratios described in the Examples below).

In some embodiments, oxidizing of the hydroxyphenyl moieties further induces substantial crosslinking of a portion of the hydroxyphenyl moieties (e.g., tyrosine side chains) and/or dihydroxyphenyl moieties (e.g., DOPA side chains), so as to form a crosslinked polymer. The crosslinks may be, for example, two hydroxyphenyl moieties crosslinked to one another (e.g., a di-tyrosine bridge), two dihydroxyphenyl moieties crosslinked to one another and/or a hydroxyphenyl moiety crosslinked to a dihydroxyphenyl moiety.

Polymers described herein are optionally prepared according to a method described herein.

The polymers described herein are optionally for use as an adhesive, for example, by contacting the polymer with an oxidizing agent (e.g., as described herein).

As exemplified herein, the dihydroxyphenyl moiety-containing polymers described herein have useful adhesive properties, and the adhesiveness of the polymers may be increased by oxidation.

Hence, according to another aspect of embodiments of the invention, there is provided a method of generating a crosslinked adhesive (e.g., a cured adhesive), the method comprising contacting a polymer comprising a dihydroxyphenyl moiety, as described herein, with an oxidizing agent, to thereby crosslink the dihydroxyphenyl moieties of said polymer.

Without being bound by any particular theory, it is believed that crosslinking of the dihydroxyphenyl moieties is primarily responsible for the increase of adhesiveness which is observed upon oxidation.

As used herein, the term "adhesive" (when used as a noun) refers to a composition (e.g., a composition comprising the polymer described herein, and optionally consisting of the polymer) which is capable of adhering to agents (e.g., solid and/or semi-solid agents) and/or of binding two such agents together.

As used herein, the terms "cure" and "curing" refers to a process (e.g., a chemical reaction) which increases an adhesiveness of an adhesive, for example, by enhancing an adherence of the adhesive to an agent and/or by enhancing the ability of the adhesive to bind two agents together (e.g., by solidifying the adhesive).

In some embodiments, crosslinking further comprises crosslinking other than crosslinking of dihydroxyphenyl moieties.

For example, as exemplified herein, oxidation may produce a double bond (e.g., carbon-carbon double bond) conjugated to dihydroxyphenyl moieties. Example of such an oxidation reaction include conversion of a dopamine moiety to an α,β-dehydrodopamine moiety, and conversion of a DOPA moiety to an α,β-dehydro-DOPA moiety.

Such conjugated double bonds may be quite reactive, thereby resulting in crosslinking reactions. In some embodiments, at least some crosslinking is effected by reaction of a nucleophilic group, such as a thiol (e.g., in a cysteine residue) and/or an amine (e.g., in a lysine residue), with the double bond.

Optionally, the oxidizing agent is oxygen, and crosslinking is effected by exposure to oxygen (e.g., to air) for a suitable period of time (e.g., at least 1 minute, at least 5 minutes, at least 15 minutes, at least 1 hour, at least 1 day).

Alternatively, and preferably, the oxidizing agent is an agent other than oxygen, which is to be provided and contacted with the polymer to effect oxidation. Examples of suitable oxidizing agents include a periodate (e.g., sodium periodate), a peroxide (e.g., hydrogen peroxide), a hypochlorite (e.g., sodium hypochlorite), a tyrosinase, a peroxidase (e.g., horseradish peroxidase), a photosensitizer, and ionizing radiation.

The use of an oxidizing agent other than oxygen has the advantage of allowing for a considerable degree of control over the time, rate and location of oxidation and consequent crosslinking of the polymer, which allows for a more conveniently used adhesive.

Simple oxidizing agents, such as periodate, peroxide, and hypochlorite, may be used alone or in combination with additional agents. For example, a peroxide may optionally be combined with a metal ion (e.g., iron-(II)) in order to effect a Fenton reaction (e.g., as described herein), which may enhance the oxidative potency of the peroxide.

Enzymes such as tyrosinase and peroxidase are preferable used in combination with any substrates and/or cofactors necessary for effecting oxidation. For example, a peroxidase is optionally used in combination with a peroxide (e.g., hydrogen peroxide) which serves as a substrate for the peroxidase. Oxygen (e.g., atmospheric oxygen) is a suitable substrate for a tyrosinase.

Use of a photosensitizer will typically be in combination with illumination (e.g., visible light and/or UV light), preferably in the presence of oxygen (e.g., atmospheric oxygen). Numerous photosensitizers are known in the art which are suitable for effecting oxidation, as well as the wavelengths of illumination which are suitable for activating each photosensitizer.

Ionizing radiation, optionally UV radiation, may optionally be used alone for effecting oxidation. Alternatively, a suitable photosensitizer may be used to enhance the efficacy of the radiation.

According to another aspect of embodiments of the invention there is provided a crosslinked adhesive (e.g., a cured adhesive), generated according to a method described herein.

The crosslinked (e.g., cured) adhesive may optionally be adhered to one or more agents, for example, adhered to two (or more) agents, thereby binding the agents together.

Agents which may efficiently adhere to adhesives described herein include, for example, organic and inorganic materials, metals (e.g., steel), wood and other cellulose-based agents (e.g., paper, cardboard), synthetic polymers (e.g., plastics), proteins and protein-based agents (e.g., collagen and derivatives thereof) and biological tissue (e.g., cartilage).

Thus, according to another aspect of embodiments of the invention, there is provided a method of binding a first agent to a second agent, the method comprising contacting the first agent with said agent in a presence of a dihydroxyphenyl moiety-containing biopolymer described herein and an oxidizing agent (e.g., as described herein).

The agents may be organic or non-organic agent.

Particular applications of the biopolymer are described herein below.

The present invention envisages binding an organic agent to another organic agent, an organic agent to a non-organic agent and/or a non-organic agent to a non-organic agent. Particular applications of the biopolymer are described herein below.

According to one embodiment, the biopolymer is used for increasing the adhesiveness of an implant. The implant may be a tissue, an organ or a synthetic implant such as a collagen based implant, a mechanical device or a scaffold (e.g. sponge). The scaffold may be seeded with cells or not. The implant may be temporary (e.g. biodegradable) or permanent.

According to one embodiment, the polymer is attached to the first agent (e.g. implant) and subsequently oxidized ex vivo. The implant is then implanted into the body whereby it adheres to the required position (i.e. second agent). Alternatively, the polymer is applied to the implant ex vivo, the implant is implanted into the body and oxidization is effected in vivo. The biopolymers may be used to increase the adhesiveness of cosmetic implants or therapeutic implants.

In some embodiments, the implant is contacted with a polymer described herein (crosslinked or non-crosslinked) in order to enhance adhesiveness of the implant.

In some embodiments, a polymer described herein (crosslinked or non-crosslinked) is used to manufacture the implant, such that the implant comprises the polymer. For example, the polymer may optionally be fashioned into an implant or a component thereof. In some embodiments, the implant consists essentially of the polymer.

According to some embodiments, an adhesive polymer described herein is used to strengthen a tissue, for example, by preventing kinking of a tissue, and or inhibiting leakage of a bodily fluid (e.g., blood) from a vessel (e.g., a blood vessel).

In some embodiments, the adhesive polymer is used to treat an aneurysm, for example, by strengthening a vessel wall.

In order to strengthen a tissue, in some embodiments an implant is placed over a surface (e.g., an external surface) of the relevant tissue (e.g., over an aneurysm), and attached to the tissue by the adhesive polymer, thereby allowing the implant to strengthen to strengthen the tissue.

In some embodiments, the adhesive polymer is contacted with the tissue, such that the polymer itself strengthens the tissue, for example, by forming a structure in situ comprising the polymer.

Without being bound by any particular theory, it is believed that treatment of an aneurysm by contacting an external surface of an aneurysm with an adhesive polymer described herein is particularly advantageous in that it does not require invasion of the interior of the blood vessel, as do some other methods for treating an aneurysm.

It is to be appreciated that the considerable elasticity of adhesive polymers according to some embodiments of the invention renders them particularly suitable for strengthening moving materials, such as many types of tissue (e.g., blood vessel walls, ligaments, tendons, tissues in joints).

According to a specific embodiment, the biopolymers are particularly useful for enhancing the adhesiveness of implants which enable bone and/or joint replacement.

In this case the implant (e.g., which has been contacted with the biopolymer) is implanted at a ligament, tendon, cartilage, intervertebral disc or bone tissue.

Thus for example, when administration of the implant is for bone regeneration, the implant is placed at a desired location in bone in such conditions such as non-union fractures, osteoporosis, of periodontal disease or defect, osteolytic bone disease, post-plastic surgery, post-orthopedic implantation, post neurosurgical surgery that involves calvaria bone removal, in alveolar bone augmentation procedures, for spine fusion and in vertebral fractures.

When the administration of the implant is for generation of tendon/ligament tissue, the implant is placed at a desired location in tendon/ligament following tissue tear due to trauma or inflammatory conditions.

When the administration of the implant is for generation of cartilage tissue, the implant is placed at a desired location in cartilage to treat defects due to Rheumatoid Arthritis, Osteoarthritis, trauma, cancer surgery or for cosmetic surgery.

When the administration of the implant is for generation of intervertebral disc tissues including nucleous pulposus and annulus fibrosus, the scaffold is placed at a desired location of nucleous pulposus degeneration, annulus fibrosus tears, or following nucleotomy or discectomy.

Another application of the biopolymers described herein is for enhancing the adhesiveness of dental implants.

Dental implants can be used to treat or repair damaged or missing teeth, and facial bones. In certain embodiments, the dental implant can be entirely for aesthetic purposes. In addition, implants can be use as a filler to augment or form dental tissue as to support the function of natural tissues (such as teeth or bone) or artificial prosthesis.

A further application of the biopolymers described herein is for enhancing the adhesiveness of cardiovascular implants, including but not limited to pacemaker cases and defibrillators, as the carrier structure for replacement heart valves, and for intra-vascular stents. Thus, for example, the present invention therefore envisions coating vascular stents with the biopolymers of the present invention.

It will be appreciated that the biopolymers of the present invention may be used during the course of surgical management or for preventing leakage in a body (e.g., closing wounds), as a glue. Preventing leakage from non-sterile environments, such as a body surface and/or the gastrointestinal tract) is of particular medical importance. For such applications, the biopolymers are optionally administered during the course of surgery and are not contacted with an implant prior to administration.

In some embodiments, the adhesive polymer is placed in an opening (e.g., a wound), to thereby close the opening.

In some embodiments, the adhesive polymer is used to glue in place a material (e.g., a patch, a membrane) which covers an opening (e.g., a wound).

As well as for biological uses, the biopolymers of the present invention may be used for a myriad of additional applications.

Since the biopolymers adhere to non-organic objects as well as organic objects, they may also be used as flexible sealants in industry. The objects may be flexible (e.g. rubber tubes) or non-flexible (cement structures, pipes etc.). The biopolymers may be useful in the case where flexibility of a sealed non-flexible object is required (e.g. in the case of temperature changes, where an object expands or contracts according to the outside temperature).

Examples of applications include, but are not limited to roofing sheets, swimming pool liners, reservoir liners, hoses, bathroom devices, industrial piping, rainwear, boots, covering materials such as food and drinks coverings/containers.

It is to be appreciated that while the biopolymers described herein are particularly suitable for medical applications such as adhesion to tissue, the biopolymers may also be used in a wide variety of applications corresponding to medical applications described herein (e.g., strengthening a material, gluing a material, closing an opening).

In some embodiments, a biopolymer described herein is used to fill a void, for either a medical application (e.g., filling a void in vivo) or a non-medical application (e.g., in industry).

In some embodiments, the void is dynamic, that is, it changes shape (e.g., a void in tissue in vivo). The elasticity of the biopolymer can allow it to effectively fill a dynamic void.

In some embodiments, the void is filled because the void is potentially harmful. For example, some voids in vivo may be particularly susceptible to infection or other complications.

In some embodiments, the void is filled in order to anchor an object in the void. For example, a relatively slender object can be attached to a surface comprising a wider void, by placing the slender object into the void, and filling at least a portion of the remaining volume of the void with the adhesive biopolymer.

In some embodiments, application of a polymer (e.g., a non-cross-linked polymer) described herein as an adhesive comprises co-application of a composition comprising the polymer and a composition comprising an oxidizing agent (e.g., as described herein).

In some embodiments, the polymer is applied in a fluid form, and hardens (e.g., solidifies) following contact with the oxidizing agent. Examples of fluid forms include, without limitation, a gel (e.g., a soft gel), a liquid (e.g., a solution, a suspension), and an aerosol (e.g., a spray generated by a spray nozzle).

In some embodiments, the polymer is applied in a solid form, and hardens (e.g., further solidifies) following contact with the oxidizing agent. Examples of solid forms include, without limitation, a membrane, a sheet, a thread, a homogeneous 3-dimensional bulk, and a scaffold.

In some embodiments, hardens is effected within 1 minute after contact with an oxidizing agent. In some embodiments, hardening is effected within 20 seconds. In some embodiments, hardening is effected within 10 seconds. In some embodiments, hardening is effected within 3 seconds. In some embodiments, hardening is effected within 1 second.

In some embodiments, contact of the polymer with the oxidizing agent is effected prior to contacting the polymer with a surface. In some such embodiments, the polymer, oxidizing agent, and concentrations thereof are selected such that crosslinking occurs over a sufficiently long time period (e.g., at least 5 seconds, at least 10 seconds, at least 20 seconds) as to allow a polymer to be contacted with a surface and adhere to the surface before the crosslinking reaction nears completion.

In some embodiments, contact of the polymer with the oxidizing agent is effected when the polymer is already in contact with a surface, such that oxidization facilitates adhesion of the polymer to the surface. In some such embodiments, the polymer, oxidizing agent, and concentrations thereof are selected such that crosslinking occurs rapidly (e.g., within 20 seconds, within 10 seconds, within 3 seconds, within 1 second).

According to some embodiments, there is provided a device (e.g., a medical device) configured for co-applying a composition comprising the polymer in fluid form (e.g., as described herein) and a composition comprising the oxidizing agent.

In some embodiments, the device comprises separate compartments for each of the compositions, and is configured so as to mix the compositions (e.g., in a predetermined proportion) and immediately thereafter release the mixed compositions.

In some embodiments, the device comprises separate compartments for each of the compositions, and is configured so as release the compositions separately (e.g., in a predetermined proportion) to a selected location, such that the compositions are likely to come into contact in the selected location.

According to some embodiments, a polymer described herein is for use in a treatment such as described herein.

According to an aspect of some embodiments of the invention, there is provided a use of a polymer described herein in the manufacture of a medicament. The medicament may be for any of the medical applications described herein.

An adhesive described herein may be provided per se or as part of a kit.

In some embodiments, the kit comprises an adhesive comprising a polymer (as described herein) and an oxidizing agent (e.g., an oxidizing agent described herein). Optionally, the polymer is substantially devoid of crosslinking by the dihydroxyphenyl moiety.

The kit optionally further includes instructions for using the adhesive, for example, according to a method described herein (e.g., by effecting crosslinking by contacting the polymer with the oxidizing agent).

In some embodiments, the kit comprises a biopolymer (e.g., as described herein) which comprises at least one hydroxyphenyl moiety (e.g., in a tyrosine residue) and agents for performing a Fenton reaction (e.g., as described herein), such as, for example, iron-(II) (e.g., an iron-(II) salt and/or complex), hydrogen peroxide and citrate (e.g., as described herein). Optionally, the polymer comprising a hydroxyphenyl moiety is substantially devoid of crosslinking (e.g., by the hydroxyphenyl moiety).

The kit optionally further includes instructions for using the adhesive by effecting a Fenton reaction, for example, according to a method described herein (e.g., by effecting both conversion of hydroxyphenyl moieties to dihydroxyphenyl moieties and crosslinking via the Fenton reaction).

According to another aspect of embodiments of the invention, there is provided a crosslinked polymer, comprising crosslinked dihydroxyphenyl moieties. The crosslinked polymer optionally has the general formula I:

B'-L'-A'-A"-L"-B"     Formula III wherein:
B' and B" are each a biopolymer;
L' and L" are each a linking moiety; and
A'-A" is a pair of crosslinked dihydroxyphenyl moieties.

The crosslinked dihydroxyphenyl moieties are linked by a bond which may be at any position (i.e., ortho, meta or para) on each of the phenyl rings, relative to the linking moiety. Thus, the pair of crosslinked dihydroxyphenyl moieties may be linked by a bond which is at an ortho position on both rings, at a meta position on both rings, at a para position on both rings, at an ortho position on one ring and at a meta position on a second ring, at an ortho position on one ring and at a para position on a second ring, and/or at a para position on one ring and at a meta position on a second ring, e.g., as shown in the following formulas:

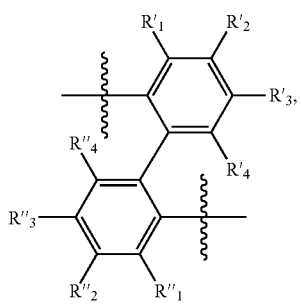

-continued

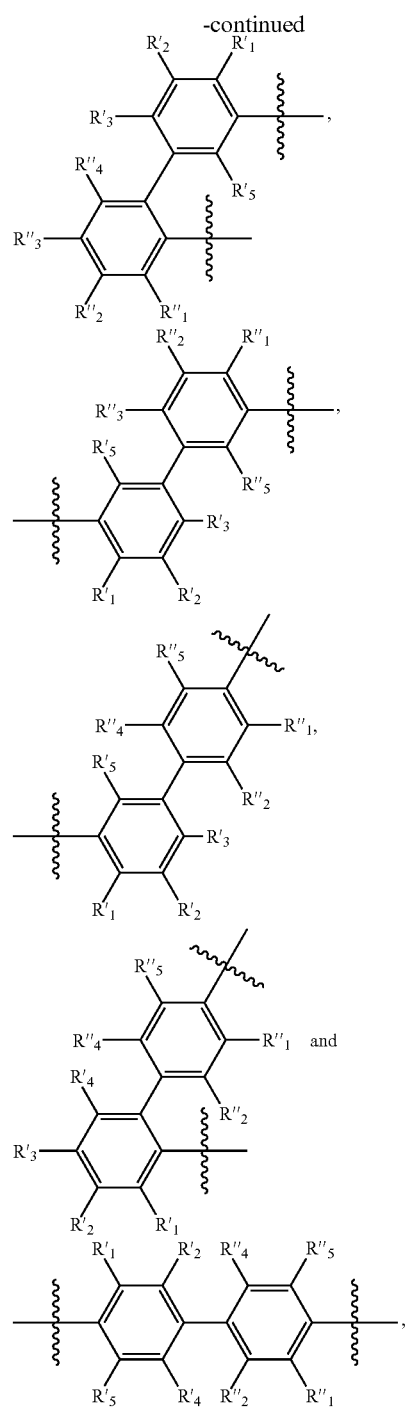

wherein each of $R'_1$-$R'_5$ and $R''_1$-$R''_5$ is independently selected from the group consisting of hydrogen, alkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, and at least two of $R'_1$-$R'_5$ and at least two of $R''_1$-$R''_5$ are hydroxy.

It is to be appreciated that each of B' and B" is a biopolymer corresponding to a biopolymer represented by the variable B herein, and each of B' and B" may be defined according to the definition of the variable B of Formula I herein. The biopolymers B' and B" may be the same or different. In addition, B' and B" may represent distinct biopolymer moieties and/or represent a single biopolymer moiety which comprises a crosslink between two sites thereof.

Similarly, each of L' and L" is a linking moiety corresponding to a linking moiety represented by the variable L herein, and each of L' and L" may be defined as is the variable L of Formula I herein. The linking moieties L' and L" may be the same or different.

Similarly, each of A' and A" is a dihydroxyphenyl moiety corresponding to a dihydroxyphenyl moiety represented by the variable A of Formula I herein. Thus, each of A' and A" may have a structure corresponding to a structure defined in Formula II herein, with the exception that A' and A" are crosslinked by a bond in the place of one of the variables $R_1$-$R_5$ of Formula II.

Thus, for example, according to some embodiments, each of the crosslinked dihydroxyphenyl rings comprises a hydroxy group at a para position, that is, $R'_3$ and $R''_3$ are each hydroxy.

According to some embodiments, each of the crosslinked dihydroxyphenyl rings comprises a hydroxy group at a meta position, that is, at least one of $R'_2$ and $R'_4$ is hydroxy, and at least one of $R''_2$ and $R''_4$ is hydroxy.

Optionally, the crosslinked dihydroxyphenyl moieties do not comprise any substituent other than hydroxy groups, such that each of $R'_1$-$R'_5$ and $R''_1$-$R''_5$ is independently selected from the group consisting of hydrogen and hydroxy.

In some embodiments, at least one of B' and B" comprises at least one resilin amino acid sequence (e.g., as described herein). Optionally, each of B' and B" comprises a resilin amino acid sequence (e.g., the same sequence, or different sequences).

In alternative embodiments, neither B' nor B" is a resilin sequence (e.g., a resilin sequence described herein).

Optionally, a linking moiety and a dihydroxyphenyl moiety (i.e., either A'-L' or A"-L") form a part of a DOPA residue (e.g., L-DOPA), as described herein, the dihydroxyphenyl moiety of the DOPA residue being crosslinked with another dihydroxyphenyl moiety.

Optionally, A'-L' or A"-L" each form a part of a DOPA residue, the DOPA residues being crosslinked with one another.

Alternatively, at least one of A'-L' and A"-L" does not form a part of a DOPA residue. Optionally, neither A'-L' nor A"-L" form a part of a DOPA residue.

In some embodiments, at least one of L' and L" is attached to a biopolymer (B' or B", respectively) via a covalent bond formed between a reactive group in the linking moiety and a functional group on the biopolymer (e.g., as described herein). Optionally, both L' and L" are attached to the respective biopolymer via such a covalent bond.

It is to be understood that the crosslinked polymer having the general formula III may optionally comprise a plurality of pairs of crosslinked dihydroxyphenyl moieties, each having a structure -A'-A" as defined herein, and each being linked to the biopolymer via linking moieties L' and L" as defined herein. The crosslinked pairs of dihydroxyphenyl moieties in the crosslinked polymer (i.e., -A'-A"-) may be the same or different, and the linking moieties (i.e., L' and/or L") attached to the various pairs of crosslinked moieties may be the same or different.

It is to be further understood that the crosslinked polymer having the general formula III may optionally comprise biopolymers in addition to B' and B", each of the additional biopolymers being crosslinked to B' and/or B", optionally via crosslinks having a structure -L'-A'-A"-L"-, as defined herein.

In some embodiments, the polymer comprises from 3 to 15 pairs of dihydroxyphenyl moieties (on average) attached to each biopolymer moiety therein, and optionally from 4 to 10 dihydroxyphenyl moieties attached to each biopolymer moiety.

The density of dihydroxyphenyl moieties on the crosslinked polymer is optionally such that the crosslinked polymer is characterized by a ratio of molecular weight to crosslinked dihydroxyphenyl moieties (each of A' and A" being counted as a crosslinked dihydroxyphenyl moiety) in a range of from 1 KDa per dihydroxyphenyl moiety to 18 KDa per crosslinked dihydroxyphenyl moiety, optionally from 1.5 KDa to 12 KDa, optionally from 2.5 KDa to 8 KDa, and optionally from 3 KDa to 6 KDa.

In embodiments wherein the crosslinked polymer is a crosslinked polypeptide (each of B' and B" is a polypeptide), wherein some amino acid residues in the polypeptide comprise a dihydroxyphenyl moiety (e.g., DOPA residues) the density of dihydroxyphenyl moieties in the crosslinked polymer is such that a percentage of amino acid residues of the crosslinked polypeptide which comprise the dihydroxyphenyl moiety is in a range of from 0.5% to 5%, optionally from 1% to 3%.

In embodiments wherein the crosslinked polymer is a crosslinked polypeptide comprising DOPA residues, the number of DOPA residues is optionally at least 20% the number of tyrosine residues in the crosslinked polypeptide, such that a ratio of a number of DOPA residues to a number of tyrosine residues in the crosslinked polypeptide is at least 1:5, optionally at least 1:3, optionally at least 1:1.5, and optionally at least 1:1.

In some embodiments, the crosslinked polymer exhibits an adhesiveness to a surface (e.g., a surface of an agent described herein), the adhesiveness being characterized by a resistance to shear stress of at least 0.001 MPa. In some embodiments, the crosslinked polymer exhibits an adhesiveness to a surface (e.g., a surface of an agent described herein), the adhesiveness being characterized by a resistance to shear stress of at least 0.01 MPa. In some embodiments, the crosslinked polymer exhibits an adhesiveness to a surface (e.g., a surface of an agent described herein), the adhesiveness being characterized by a resistance to shear stress of at least 0.1 MPa. In some embodiments, the crosslinked polymer exhibits an adhesiveness to a surface (e.g., a surface of an agent described herein), the adhesiveness being characterized by a resistance to shear stress of at least 0.5 MPa. In some embodiments, the crosslinked polymer exhibits an adhesiveness to a surface (e.g., a surface of an agent described herein), the adhesiveness being characterized by a resistance to shear stress of at least 1.5 MPa. In some embodiments, the crosslinked polymer exhibits an adhesiveness to a surface (e.g., a surface of an agent described herein), the adhesiveness being characterized by a resistance to shear stress of at least 3 MPa. In some embodiments, the crosslinked polymer exhibits an adhesiveness to a surface (e.g., a surface of an agent described herein), the adhesiveness being characterized by a resistance to shear stress of at least 10 MPa. In some embodiments, the crosslinked polymer exhibits an adhesiveness to a surface (e.g., a surface of an agent described herein), the adhesiveness being characterized by a resistance to shear stress of at least 20 MPa.

Resistance to shear stress may be determined by applying a polymer between two similar surfaces (e.g., surfaces consisting of the same material), as described herein.

In exemplary embodiments, the shear stress is in an in-plane shear mode, referred to in the art as Mode II. Various techniques for determining resistance to such shear stress are known in the art. Examples of suitable techniques include, without limitation, an end notch flexure test, a symmetrical crack lap shear test, and a dissymmetrical crack lap shear test, as these tests are performed in the art.

In some embodiments, the crosslinked polymer exhibits an adhesiveness to a surface (e.g., a surface of an agent described herein), the adhesiveness being characterized by resistance to stress of at least 1 KPa in a direction perpendicular to the surface. In some embodiments, the crosslinked polymer exhibits an adhesiveness to a surface (e.g., a surface of an agent described herein), the adhesiveness being characterized by resistance to stress of at least 3 KPa in a direction perpendicular to the surface. In some embodiments, the crosslinked polymer exhibits an adhesiveness to a surface (e.g., a surface of an agent described herein), the adhesiveness being characterized by resistance to stress of at least 10 KPa in a direction perpendicular to the surface. In some embodiments, the crosslinked polymer exhibits an adhesiveness to a surface (e.g., a surface of an agent described herein), the adhesiveness being characterized by resistance to stress of at least 14 KPa in a direction perpendicular to the surface. In some embodiments, the crosslinked polymer exhibits an adhesiveness to a surface (e.g., a surface of an agent described herein), the adhesiveness being characterized by resistance to stress of at least 20 KPa in a direction perpendicular to the surface. In some embodiments, the crosslinked polymer exhibits an adhesiveness to a surface (e.g., a surface of an agent described herein), the adhesiveness being characterized by resistance to stress of at least 40 KPa in a direction perpendicular to the surface. In some embodiments, the crosslinked polymer exhibits an adhesiveness to a surface (e.g., a surface of an agent described herein), the adhesiveness being characterized by resistance to stress of at least 80 KPa in a direction perpendicular to the surface.

Resistance to stress perpendicular to a surface may be determined by applying a polymer between two surfaces, and pulling the surfaces apart, as described herein.

Various techniques for determining resistance to such stress are known in the art, e.g., techniques for measuring opening, also referred to in the art as Mode I. Examples of suitable techniques include, without limitation, a double cantilever beam tests (DCB), and a wedge test, as these tests are performed in the art.

In some embodiments, the surface(s) comprises collagen (e.g., two surfaces comprising collagen). In some embodiments, the surface(s) consists essentially of collagen. In exemplary embodiments, the collagen is substantially moist, for example, swollen with water. In some embodiments, the collagen is substantially dry. It is to be appreciated that adhesiveness with respect to a moist surface (e.g., as exemplified herein) may be lower than adhesiveness to a dry surface, as moisture is not particularly conductive to strong adhesion.

In some embodiments, the surface(s) comprises cartilage. In some embodiments, the surface(s) consists essentially of cartilage (e.g., knee cartilage, as described herein).

In exemplary embodiments (e.g., for testing resistance to stress perpendicular to a surface), one surface consists essentially of cartilage and a second surface consists essentially of collagen.

In some embodiments, the cross-linked polymer is characterized as being elastic under a compression strain of 50% (e.g., s determined according to a procedure described herein). In some embodiments, the cross-linked polymer is characterized as being elastic under a compression strain of 60%. In some embodiments, the cross-linked polymer is characterized as being elastic under a compression strain of 65%. In some embodiments, the cross-linked polymer is characterized as being elastic under a compression strain of 70%. In some embodiments, the cross-linked polymer is characterized as being elastic under a compression strain of 75%. In some embodiments, the cross-linked polymer is characterized as being elastic under a compression strain of 80%.

In some embodiments, the cross-linked polymer is characterized as being elastic under a compression stress of 50 KPa. In some embodiments, the cross-linked polymer is characterized as being elastic under a compression stress of 100 KPa. In some embodiments, the cross-linked polymer is characterized as being elastic under a compression stress of 150 KPa. In some embodiments, the cross-linked polymer is characterized as being elastic under a compression stress of 200 KPa. In some embodiments, the cross-linked polymer is characterized as being elastic under a compression stress of 250 KPa. In some embodiments, the cross-linked polymer is characterized as being elastic under a compression stress of 300 KPa. In some embodiments, the cross-linked polymer is characterized as being elastic under a compression stress of 350 KPa. In some embodiments, the cross-linked polymer is characterized as being elastic under a compression stress of 400 KPa. In some embodiments, the cross-linked polymer is characterized as being elastic under a compression stress of 500 KPa. In some embodiments, the cross-linked polymer is characterized as being elastic under a compression stress of 750 KPa.

The elasticity under a compression is optionally characterized as a lack of plastic deformation (e.g., as determined via a stress-strain curve).

Optionally, the adhesiveness is formed by crosslinking a polymer in contact with the surface (e.g., by a process described herein), so as to generate the crosslinked polymer adhered to the surface. In such embodiments, very strong adhesiveness to the surface may be obtained, although the crosslinked polymer may not necessarily exhibit any significant adhesiveness to a surface other than that which was in contact with the polymer during crosslinking.

Alternatively or additionally, the crosslinked polymer exhibits adhesiveness to surfaces which were not previously in contact with the crosslinked polymer (i.e., the crosslinked polymer is sticky).

In such embodiments, the crosslinked polymer optionally comprises dihydroxyphenyl moieties (e.g., as in Formula I herein) which may optionally provide stickiness, in addition to crosslinked dihydroxyphenyl moieties (e.g., as in Formula III herein) which may optionally provide enhanced physical strength and/or enhanced adhesiveness to a surface that which was in contact with the polymer during crosslinking. That is, a polymer may have both the general formula I and the general formula III described herein. As described herein, such polymers may be obtained by using a Fenton reaction.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "treat" and "treating", in the context of a medical condition, include abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Resilin Production, Gene Design, Plasmid Construction, Expression and Purification:

Recombinant resilin was produced in *E. coli*, extracted and purified as described in U.S. Patent Application No. 2010/0317588.

pET29-6H-exon1 vector was transformed into BL21 (DE3) Star (Invitrogen). Authenticity of the clone was confirmed by DNA sequencing. Firstly BL21 (pET29-6H-exon1) Glycerol stock (10 μl) were transferred into M9 minimal media (5 ml, with addition of $MgSO_4$, Glucose and A-Z casamino acids) and kanamicin (50 μg/ml final concentration). The start cultures were incubated over night in a rotary shaker (250 rpm, 37° C.) and were used to inoculate 2 liter flasks containing Terrific Broth (200 ml) and kanamicin (50 μg/ml final concentrations). IPTG (0.5 mM final concentration) was added at $OD_{600\,nm}$ values of ~2 (~4 hours post inoculums). Following ~4 hour post induction, bacteria were harvested by centrifugation (85,000 g, 10 min, 4° C.) and the recovered cell pellets were stored (-80° C.) till use. At all time, shaking flasks were agitated at 250 rpm in a 37° C. incubator.

Bacteria cell pellets were thawed and re-suspended in the lysis buffer containing Na-phosphate (20 mM), NaCl (0.5 M), imidazole (25 mM) and complete protease inhibitor (Roche) followed by 20 min sonication in ice bath. The soluble fraction was separated by centrifugation (10,000 g, 45 min and 10° C.). Cleared bacteria lysates were filtered via 0.45 μm syringe membrane followed by affinity chromatography (AC) on HisPrep FF 16/10 Ni-NTA pre-equilibrated 20 ml column, mounted to AKTAprime plus FPLC (GE, Sweden). 6H-exon 1 was purified using two buffer systems, which were buffer "A" (binding) containing Na-phosphate (20 mM), NaCl (0.5 M) and imidazole (25 mM), and buffer "B" (elution) containing Na-phosphate (20 mM), NaCl (0.5 M) and imidazole (500 mM). Both buffers were adjusted to pH 7.4. (1) 2 column volumes (CV) of buffer "A" at 5 ml/min, (2) 75 ml injection of the lysate at 5 ml/min, (3) 5 CV wash with buffer "A", (4) 5 CV step of 10% buffer "B", (5) 7 CV step of 100% buffer "B", (6) equilibration with 5 CV of binding buffer at 1 ml/min. Eluted proteins were detected at 280 nm. 1.5 ml of eluted fractions were collected and analyzed by 12.5% SDS-PAGE. Subsequently, AC purified 6H-exon 1 containing fractions were pooled and diluted with buffer "A" (final concentration of 2 mg/ml).

SDS-PAGE analysis of the crude bacterial lysates showed an intense recombinant 6H-exon 1 band (~35 kDa) after post IPTG induction for 4 h, which correspond to the Ni-NTA purified product estimated at >90% purity.

Colorimetric Assay of Dihydroxyphenyl Moieties

The degree of dihydroxyphenyl moieties in derivatized resilin was determined quantitatively via nitration assay, according to procedures described in Waite & Benedict [*Methods Enzymol* 1984, 107:397-413]. Lyophilized derivatized resilin was dissolved in water at a concentration of 1.5 mg/ml, and purity and concentration of the solution were confirmed via SDS-PAGE and measurement of optical density (OD) at a wavelength of 280 nm. Resilin solutions (5-20 µl) were transferred to 0.5 N HCl, so as to obtain a final volume of 300 µl HCl solution with resilin. 300 µl of a solution comprising sodium nitrite (1.45 M $NaNO_2$) and sodium molybdate (0.41 M) was then added. 400 µl of 1 M NaOH was then added, and the optical density of the obtained 1 ml solutions was measured at a wavelength of 500 nm. Dopamine served as a positive control, and for preparing standard curves, and water served as a negative control and blank solution.

The degree of resilin derivatization was calculated based on the presence of 18 carboxylate-containing charged amino acids in recombinant resilin (30 KDa), such that 1.5 mg/ml of resilin results in a concentration of 900 µM carboxylate groups. Thus, for example, a presence of 450 µM dihydroxyphenyl moieties indicates a derivatization of 50%.

Fluorescence Assay of Dihydroxyphenyl Moieties

Dopamine was dissolved in water and analyzed for maxima in the emission and excitation spectra, using a Cary Eclipse Fluorometer. Based on these results, solutions comprising 0-800 nM dopamine were then measured for fluorescence in order to obtain a standard curve, using an excitation wavelength of 280 nm and an emission wavelength of 320 nm. Catechol concentration in conjugated resilin was determined at the same excitation and emission wavelengths, and at the same pH and solution conditions.

The fluorescence assays confirmed the results of colorimetric assays.

Fenton Cross-Linking and Analysis

Exon 1 resilin was polymerized via a chelate modified photo-Fenton reaction. All cross-linked polymers in this method were originated from 200 mg/ml resilin solutions. In addition, all polymerization trials were conducted at a citrate:Fe:$H_2O_2$ molar ratio of approximately 5:1:20/10, respectively at pH 5. A concentrated resilin solution containing different concentrations (3-140 mM) of $FeSO_4$ was vigorously mixed with $H_2O_2$, following 10 to 15 second vortex. The resulting mixtures were transferred to 50 µl Teflon molds followed by illumination via UV light-emitting diodes (LEDs) (370 nm, 10 mW/cm$^2$, 10 to 15 minutes). The polymers were detached from the Teflon molds and qualitatively evaluated for curing time, homogeneity and elasticity. A Nikon 80i microscope with a 2A filter cube (Excitation wavelength: 330-380 nm, Emission wavelength >420 nm) was used for polymerized resilin photomicrography. The polymers were washed in the citrate buffer prior to photomicrography under white or ultraviolet light. For comparison, non-crosslinked samples were prepared by illuminating resilin in citrate buffer under the same conditions, except without $FeSO_4$ and $H_2O_2$.

Amino Acid Analysis of Polymerized Exon 1 Resilins

Five mg polymerized and non-polymerized resilin samples were hydrolyzed in 6 N HCl containing 0.1% phenol (145° C., 4 hr), following filtration though 0.22 µm syringe membrane. Hydrolysis products were analyzed in an Agilent 1200 HPLC system with Diode Array and fluorescence detectors (Santa Clara, Calif., USA). UV absorbance and fluorescence were measured at 280 nm, and at typical excitation/emission spectra for di-tyrosine ($\lambda_{Ex}$ 305 nm: $\lambda_{Em}$ 400 nm) and DOPA ($\lambda_{Ex}$ 280 nm: $\lambda_{Em}$ 320 nm) detection. The chromatography system was used with a LiChrospher 100 RP-18 column (5 µm). Hydrolysis products were eluted using increasing acetonitrile (containing 0.1% TFA) gradient. Additional analysis of the hydrolysis products was carried out in a Thermo Ltq-Orbitrap MS and an Accela High Speed HPLC (LC-MS) with an Agilent Zorbax Eclipse XDB-C18 column (2.1×100 mm, particle size 1.8 µm).

Di-Tyrosine Standard

A 20 µg/ml HRP solution was added to 5 mM L-tyrosine in borate buffer (50 mM, pH 9), following the immediate addition of 3 mM $H_2O_2$. After incubation for 30 minutes at 37° C., the reaction mixture was centrifuged through a Centricon™ tube (molecular weight cut-off of 10 kDa and 3 kDa) for HRP removal. The filtrate was stored (−18° C.) until use. Di-tyrosine was verified in the filtrate using LC-MS. The di-tyrosine/tyrosine mixture was used as a standard for di-tyrosine and tyrosine retention times and UV spectra.

Biomaterial Properties

Structural Assessments—

Resilin samples were lyophilized and the structural characteristics were observed using Fourier transform infrared spectroscopy (FTIR) as we have previously reported [25, 26]. The fractions of secondary structural components including random coil, alpha-helices, beta-strands and turns were evaluated using Fourier self-deconvolution (FSD) of the infrared absorbance spectra. FSD of the infrared spectra covering the amide I region (1595-1705 cm$^{-1}$) was performed by Opus 5.0 software. The second derivative was first applied to the original spectra in the amide I region with a nine-point Savitsky-Golay smoothing filter. Deconvolution was performed using Lorentzian line shape with a half-bandwidth of 25 cm$^{-1}$ and a noise reduction factor of 0.3 [25, 26]. Circular Dichroism (CD) spectra were also studied for the secondary structure of resilin samples as previously described [27]. All spectra were recorded at room temperature (25° C.) using a 1 mm path-length quartz cell. Resilin samples were measured in 1×PBS with concentrations in the range of 1.0-3.0 mg/ml. CD data were analyzed using a DICHROWEB program [28, 29].

Mechanical Assessments—

The elastic properties of uncross-linked and cross-linked proteins were performed using Atomic Force Microscopy (AFM) as previously described [12, 16, 30]. A force-distance curve was obtained for evaluation of material properties. Resilin samples were dried on the surface of mica. Measurements on uncross-linked and cross-linked were conducted in force mode with 20 independent trials and mica was used as a control to calibrate the instrument. Resilience was calculated as the ratio of the area under the penetration and retraction curves in the force-distance curves [12, 16, 30].

Example 1

Resilin-Dopamine Conjugate

The protein resilin was conjugated to dopamine, a dihydroxyphenyl-containing compound. In particular, the amine group of dopamine was conjugated (via formation of an amide bond) to carboxylic acid groups of negatively-charged amino acid residues of resilin. As the conjugate comprises a dihydroxyphenyl-containing moiety which is an analog of the side chain of DOPA, such conjugation is referred to herein as "dopylation".

Preparation of Adhesive:

DMSO or DMSO with water was bubbled with $N_2$ gas for 15 minutes to remove oxygen. Lyophilized resilin was then added at a final concentration of 2 mg/ml. 4 mM of BOP ((benzotriazol-1-yloxy)tris(dimethylamino)phosphonium hexafluorophosphate), 4 mM of HOBt (1-hydroxybenzotriazole), 13.5 mM of dopamine hydrochloride, and 10.8 mM of triethylamine were then added. The reaction mixture was covered with tin foil and kept under $N_2$ for 2 hours at room temperature. Subsequently, the dopylated resilin was precipitated overnight with cold acetone, and centrifuged at 10000 g for 15 minutes at 4° C., to yield dopylated resilin as a white pellet. The obtained pellet was vacuum-dried and stored at a temperature of −20° C. until further processing. The pellet was then dissolved in HCl (10 mM), extensively dialyzed against acidic water (pH 3.5-4), and then finally freeze-dried for long-term storage.

Lyophilized dopylated resilin was dissolved in water, and the degree of dopamine conjugation was determined via a colorimetric nitration assay, as described hereinabove. The assay showed that 25% of the negatively charged amino acids of native resilin were conjugated to dopamine, and that each resilin free chain (Exon 1 only) was conjugated to approximately 5 dopamine molecules.

Another sample of dopylated resilin was prepared as described hereinabove, except that HBTU (O-benzotriazole-N,N,N',N'-tetramethyluronium hexafluorophosphate) was used instead of BOP. The molar ratio of resilin free carboxylate groups to reagents was 1:4:4:10:8 (free carboxylate groups: HBTU:HOBt:dopamine:triethylamine). The degree of dopamine conjugation was determined as described hereinabove, and found to be approximately 85% (corresponding to approximately 15 conjugated dopamine molecules per resilin molecule), which was considerably higher than the efficiency achieved with the same molar ratio of BOP.

In another sample, resilin was dopylated using a lower ratio of condensation reagents (HBTU and HOBt) to carboxylate groups. The molar ratios were 2:2:2:10:8 (free carboxylate groups: HBTU:HOBt:dopamine:triethylamine). The degree of dopamine conjugation was determined as described hereinabove, and found to be approximately 50% (corresponding to approximately 9 conjugated dopamine molecules per resilin molecule).

These results indicate that the degree of dopylation can be modulated by selecting appropriate condensation reagents and molar ratios of condensation reagents to resilin carboxylate groups.

Example 2

Activation and Curing of Dopamine-Resilin Conjugate

Samples of lyophilized dopylated resilin, prepared as described in Example 1, were dissolved in water or isopropanol:water (1:9) at a final concentration of approximately 200 mg/ml (up to 300 mg/ml). 10-30 mM of sodium periodate or periodic acid was added to activate the dopylated resilin, and resulted in an immediate change from clear and transparent solutions to yellow-orange viscous solutions.

Activated dopylated resilin samples were cast into a 3-D mold and cured at room temperature.

The cured dopylated resilins were detached from the molds and their elasticity was evaluated. The obtained resilin displayed high flexibility and elasticity, as in the case of resilin crosslinked by conventional methods, such as described in U.S. Patent Application No. 2010/0317588, Qin et al. [*Biomacromolecules* 2009, 10:3227-3234], and Elvin et al. [*Nature* 2005, 437:999-1002].

In order to quantitatively evaluate the elastic modulus and flexibility of cured dopylated resilins, samples were prepared by dissolving 5 mg of dopylated resilin in ultra-pure water to a concentration of 150 mg/ml, and then activated with 15 mM or 30 mM periodic acid. After vigorous mixing for 30 seconds the viscous solutions were cast in molds with a 4.5 mm diameter. Following 5 minutes of curing, the obtained crosslinked resilin was subjected to compression at a rate of 2 mm per minute. Cured resilin samples were tested either dry or following swelling upon immersion in double distilled water.

As shown in FIG. 6, the cured dopylated resilin, when either dry or swelled, was highly flexible and elastic, being capable of withstanding compression strain of about 60% to about 75%, and compression stress of about 150-350 KPa.

These results indicated that dopylated resilin can be readily crosslinked to form a resilient and highly elastic material.

Example 3

Activated Dopamine-Resilin Conjugate as Adhesive

Dopylated resilin was activated as described in Example 2, and cast between two materials, followed by curing, in order to glue the two materials together.

In order to quantitatively evaluate the ability of the glued membranes to withstand extension forces, dopylated resilin was dissolved in ultra-pure water to a concentration of 200 mg/ml, and then activated with periodic acid, the final concentrations being 30 mM periodic acid and 150 mg/ml dopylated resilin. After vigorous mixing for 30 seconds the viscous solutions were applied onto 0.5×4 cm strips of recombinant human collagen membranes. Following 5 minutes of curing, the obtained glued membranes were subjected to extension in a tensile tester at a rate of 2 mm per minute, until detachment of the membranes, as depicted in FIG. 7.

As shown in FIG. 8, collagen membranes glued together with the cured dopylated resilin withstood extension stress in the form of shear (along the plane of the membranes) of about 1.5 MPa to about 3.5 MPa, and extension strain of from about 7% to about 17%.

Similarly, the activated dopylated resilin was used to glue a collagen membrane to a porcine artery, in order to evaluate adhesiveness to biological tissue.

As shown in FIGS. 9A and 9B, a collagen membrane glued to a porcine artery with the cured dopylated resilin withstood extension forces.

In addition, activated dopylated resilin was applied to collagen sponges, and used to glue the collagen sponges to defects in a sheep knee, in order to quantitatively evaluate adhesiveness to biological tissue in a model of a cartilage defect.

Dopylated resilin was dissolved in ultra-pure water to a concentration of 130 mg/ml, and the solution was then applied onto 6 mm diameter recombinant human collagen sponges, which were then frozen and lyophilized, so as to result in dopylated resilin crown coated collagen sponges. 6 mm diameter defects were created on a sheep knee.

As shown in FIGS. 10A-10C, the dopylated resilin-coated collagen sponges were then activated by being dipped in 15 μl of 25 mM sodium periodate (FIGS. 10A and 10B), and then placed in a defect (FIG. 10C).

As shown in FIG. 11, after one to two minutes, the collagen sponges adhered to the defects sufficiently strongly such that they did not detach when pulled with tweezers.

The adhesion force was further tested quantitatively using a tensile tester. In order to facilitate use of the tensile tester, a piece of plastic slide was attached to the collagen sponge using super glue, and the plastic was then held by the gripper of the tensile tester. The test was performed using a rate of 2 mm per minute until detachment of the sponge from the defect.

As shown in FIG. 12, collagen sponges glued to a sheep knee defect with the cured dopylated resilin withstood extension strain (perpendicular to the surface of adhesion) of from about 150% to about 200%, and extension stress of about 14 KPa.

These results indicate that derivatives of biopolymers such as resilin can be crosslinked in a biocompatible, light-independent and enzyme-free manner, and which can serve as highly elastic and a highly adhesive glue for tissue engineering applications, including in vivo/situ methods.

Example 4

Mechanism of Activation and Curing

In order to study the mechanism of activation and curing, dopylated resilin, prepared as described in Example 1, was dissolved at low concentrations (1-10 mg/ml), and then incubated in the presence of sodium periodate for 6 hours. The UV-visible light absorption spectrum of reaction mixture was measured at various times during the incubation with sodium periodate, and compared with the absorption spectra of known products of dopamine oxidation.

As shown in FIG. 13A, addition of sodium periodate to dopylated resilin resulted in initial absorption characterized by a broad peak with a maximum at approximately 395 nm, followed by a gradual increase of absorption at wavelengths of up to about 310-330 nm, with concomitant decrease of absorption at 395 nm.

These results indicate that quinone moieties, which absorb strongly at approximately 395 nm, are initially formed by periodate-induced oxidation of dihydroxyphenyl moieties in dopylated resilin, and that the quinone moieties then react to form crosslinked dihydroxyphenyl moieties, which absorb strongly at approximately 280 nm, as well as additional oxidation products, such as derivatives of $\alpha,\beta$-dehydroDOPA (e.g., $\alpha,\beta$-dehydrodopamine moieties), which absorb strongly at approximately 320 nm.

Thus, as depicted in FIG. 13B, crosslinking of dopylated resilin may be effected by formation of dopamine quinone moieties, reaction of dopamine quinone moieties (e.g., with a dopamine moiety) to form radicals, and reaction of the radicals to form a crosslinked dopamine moiety.

In addition, the abovementioned $\alpha,\beta$-dehydroDOPA derivatives may also react (e.g., with thiol and/or amine groups) so as to result in polymerization and crosslinking.

Example 5

Adhesive Resilin Comprising DOPA Residues

Dihydroxyphenyl moieties were introduced into resilin by enzymatically converting tyrosine residues into DOPA residues, instead of by conjugation.

Lyophilized resilin (1.5 mg/ml) was incubated with 30 units/ml of mushroom tyrosinase for 60 minutes at a temperature of 20° C., in the presence of sodium phosphate (100 mM, pH 6.5) and sodium ascorbate (30 mM). The tyrosinase was inactivated by either heat treatment or acid treatment. The resilin was analyzed at various time points during incubation in order to determine the degree of tyrosine conversion to DOPA, using a colorimetric nitration assay as described hereinabove.

As shown in FIG. 14, approximately 40% of tyrosine residues were converted to DOPA residues, such that each resilin free chain contained approximately 7 DOPA residues. As further shown therein, this level of DOPA residues was achieved following approximately 30 minutes of incubation with mushroom tyrosinase.

The DOPA-containing resilin adhesive can be activated and cured, and used as an adhesive, using procedures such as described in Examples 2 and 3.

Example 6

Adhesive Fenton-Crosslinked Resilin

Exon 1 resilin was prepared as described hereinabove and was crosslinked using a photoinduced Fenton reaction, using $FeSO_4$ and $H_2O_2$.

The resilin was exposed to different concentrations and ratios of $FeSO_4$ and $H_2O_2$ in order to determine optimal conditions for exon 1 resilin crosslinking, while maintaining a constant protein concentration, as described in the Materials and Methods section hereinabove. The resilin was then cured by UV illumination using 3 mW UV LEDs, as shown in FIG. 15. Resilin crosslinking was obtained under all conditions evaluated. When high iron concentrations were applied (resilin:iron molar ratios in a range of 1:1-0.4), immediate crosslinking was observed and inhomogeneous polymers formed prior to UV illumination. These reactions were hard to control, although the polymers visually showed good strength and elasticity when pressed by tweezers. In order to obtain more control over crosslinking, lower iron concentrations were used, with a resilin:iron molar ratio in a range of 1:0.2-0.03. These reactions resulted in a more controllable crosslinking, wherein crosslinking could be controllably induced by UV illumination, and the obtained crosslinked polymers were elastic.

In order to improve control over the crosslinking reaction, the photo-Fenton reaction was modified by the use of citrate as a chelator, as described in the Materials and Methods section hereinabove. Lyophilized resilin was dissolved at a final concentration of 200 mg/ml in a solution of sodium citrate (50 mM, pH 5.5) with 7 mM iron-(II) sulfate and 20 mM hydrogen peroxide. A viscous resilin solution was obtained, which was mold cast and cured by irradiation for 10 minutes with UV light (370 nm, 10 $mW/cm^2$), using 3 mW UV LEDs.

As shown in FIGS. 16 and 17, crosslinked polymers obtained using 30 mM (FIG. 16) and 3 mM $FeSO_4$ (FIG. 17) were brown-yellow in color and exhibited high elasticity and rubber-like properties when compression forces (FIG. 16) and extension forces (FIG. 17) were applied. As further shown therein, the polymer color was dependent upon iron content; relatively high iron content resulted in brownish polymers (FIG. 16) while relatively low iron content resulted in yellowish polymers (FIG. 17). As further shown in FIG. 17, the crosslinked polymers displayed adhesive features when placed on surfaces such as stainless steel, plastics and paper.

The contents of the photoinduced Fenton-crosslinked resilin was compared to that of resilin crosslinked using Ru-APS, as described in the art [16]. The crosslinked resilins were acid-hydrolyzed and subjected to C-18 reverse phase separation, and then analyzed by LCMS (liquid chromatography-mass spectrometry) and HPLC (high precision liquid chromatography).

As shown in FIG. 18, HPLC analysis using C-18 reverse phase separation of acid hydrolyzed resilin polymers revealed the formation of DOPA during the photoinduced Fenton crosslinking. A further shown therein, the formation of DOPA was observed only in the Fenton crosslinking system and did not occur in Ru-APS crosslinking.

LCMS analysis confirmed these results (data not shown).

These results suggest that the formation of DOPA is a reason for the adhesiveness of polymers prepared with the photoinduced Fenton system, which contrasts with the lack of adhesiveness of polymers resulting from Ru-APS crosslinking, as DOPA has been reported as an adhesive component in mussel proteins [22].

The crosslinked resilin was further analyzed by photomicrography. A Nikon 80i microscope with a 2A filter cube (excitation wavelength: 330-380 nm, emission wavelength >420 nm) was used for polymerized resilin photomicrography. The polymers were washed in the citrate buffer, and then viewed by photomicrography under white or ultraviolet light.

As shown in FIG. 19, fluorescence microscopy of the crosslinked resilin revealed vivid blue fluorescence at excitation/emission wavelengths of di-tyrosine fluorescence. These results indicate that in addition to formation of DOPA, crosslinking of resilin occurred by formation of crosslinks comprising di-tyrosine (as occur in natural resilin [Neff et al., *Arthropod Struct Dev* 2000, 29: 75-83]) or a derivative thereof.

As shown in FIG. 20, HPLC analysis using C-18 reverse phase separation of acid hydrolyzed resilin polymers revealed the formation of fluorescent di-tyrosine during the photoinduced Fenton crosslinking.

As further shown therein, various peaks were observed representing additional compounds with emission-excitation properties similar to those of di-tyrosine. These results suggest that crosslinks other than di-tyrosine are present, for example, crosslinked DOPA and/or other crosslinked tyrosine derivatives.

The content of di-tyrosine formed in the photo-Fenton reaction was less than 5% of the available tyrosines, significantly lower compared to the Ru-APS resilin polymerization method previously reported [16]. These results are consistent with the evidence presented herein that some of the available tyrosines react to form DOPA residues and other tyrosine derivatives.

Solid hydrogels could be formed even from 85 mg/ml resilin solutions (data not shown), which was not the case when recombinant resilin was polymerized via the Ru-APS system [16].

This result indicates that the photo-Fenton reaction is more efficient at cross-linking than the Ru-APS system, despite the Ru-APS system being more efficient at generating di-tyrosine. This is consistent with the evidence presented herein that cross-linking by the photo-Fenton reaction is mediated by mechanisms other than di-tyrosine formation.

AFM was used (as described herein) to determine the molecular level elastic modulus and elasticity of non-crosslinked resilin and crosslinked resilin prepared by the photo-Fenton system. Based on force-distance curves, the resilience of non-crosslinked resilin was 91±3% and 94.5±3% for the crosslinked resilin. In addition, the elastic modulus of both crosslinked and non-crosslinked resilin was calculated at 9.8±2% and 10.2±2% MPa, respectively. The elastic modulus at the macroscale of water saturated 3D cylinders prepared from resilin and polymerized by the photo-Fenton system was 22 kPa, in line with the reports of Elvin et al, 2005.

These results indicate that photo-Fenton reactions did not alter the elastic properties of the protein and successfully mimicked the properties of resilin. The resulting crosslinked resilin maintained its rubbery nature compared to previously reported cross-linking methods [12, 16].

Thus, the results presented herein demonstrate that resilin may be crosslinked in a biocompatible manner to generate useful biomaterials.

Example 7

Periodate-Induced Oxidation of Resilin

In order to further evaluate the effects of dopylation on resilin oxidation, non-dopylated resilin was oxidized with periodate, and the properties of the product were compared to that of periodate-treated dopylated resilin as described hereinabove.

Lyophilized resilin, without any prior derivatization, was dissolved in phosphate buffer saline (PBS) and sodium periodate was added. The final concentrations were 180 mg/ml resilin and 65 mM sodium periodate. After incubation for 60 minutes, a solid hydrogel was formed, which was transparent, orange and high elastic, as shown in FIG. 21. The hydrogel was easily detachable from the surface it was formed on, and did not exhibit the adhesive properties observed with dopylated resilin.

These results indicate that dopylation greatly reduces the time required for curing, from ~60 minutes with non-dopylated resilin, to within ~1 minute or even within seconds with dopylated resilin, and that dopylation is needed to provide significant adhesiveness.

The adhesiveness and considerable reduction in curing time suggest that curing of dopylated resilin can be considerably more useful than curing of native resilin in many medical applications.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] Vogel S. Living in a physical world III. Getting up to speed. J Biosci 2005; 30: 303-312.

[2] Alexander R M, Bennet-Clark H C. Storage of elastic strain energy in muscle and other tissues. Nature 1977; 265: 114-117.

[3] Gronenberg. Fast actions in small animals: springs and click mechanisms. J Comp Physiol [A] 1996; 178: 727-734.
[4] Weis-Fogh T. A Rubber-Like Protein in Insect Cuticle. J Exp Biol 1960; 37: 887-907.
[5] Haas F, Gorb S, Blickhan R. The function of resilin in beetle wings. *Proc Biol Sci* 2000; 267: 1375-1381.
[6] Bennet-Clark H C, Lucey E C A. The Jump of the Flea: A Study of the Energentics and a Model of the Mechanism. J Exp Biol 1967; 47: 59-67.
[7] Burrows M, Shaw S R, Sutton G P. Resilin and chitinous cuticle form a composite structure for energy storage in jumping by froghopper insects. BMC Biol 2008; 6: 41.
[8] Young D, Bennet-Clark H C. The Role of the Tymbal in Cicada Sound Production. J Exp Biol 1995; 202: 2937-2949.
[9] Ardell D H, Andersen S O. Tentative identification of a resilin gene in *Drosophila melanogaster*. Insect Biochem Mol Biol 2001; 31: 965-970.
[10] Lombardi E C, Kaplan D L. Preliminary characterization of resilin isolated from the cockroach, *Periplaneta americana*. Mater Res Soc Symp Proc 1993; 292: 3-7.
[11] Rebers J E, Riddiford L M. Structure and expression of a Manduca sexta larval cuticle gene homologous to *Drosophila* cuticle genes. J Mol Biol 1988; 203: 411-423.
[12] Qin G, Lapidot S, Numata K, Hu X, Meirovitch S, Dekel M, et al. Expression, cross-linking and characterization of recombinant chitin binding resilin. Biomacromolecules 2009; 10: 3227-3234.
[13] Nairn K M, Lyons R E, Mulder R J, Mudie S T, Cookson D J, Lesieur E, et al. A synthetic resilin is largely unstructured. Biophys J 2008; 95: 3358-3365.
[14] Bochicchio B, Pepe A, Tamburro A M. Investigating by C D the molecular mechanism of elasticity of elastomeric proteins. Chirality 2008; 20: 985-994.
[15] Kim M, Elvin C, Brownlee A, Lyons R. High yield expression of recombinant pro-resilin: Lactose-induced fermentation in *E. coli* and facile purification. Protein Expr Purif 2007; 52: 230-236.
[16] Elvin C M, Can A G, Huson M G, Maxwell J M, Pearson R D, Vuocolo T, et al. Synthesis and properties of crosslinked recombinant pro-resilin. Nature 2005; 437, 999-1002.
[17] Dutta N K, Choudhury N R, Truong M Y, Kim M, Elvin C M. Physical approaches for fabrication of organized nanostructure of resilin-mimetic elastic protein rec1-resilin. Biomaterials 2009; 30, 4868-4876.
[18] Charati M B, Ifkovits J L, Burdick J A, Linhardt J G, Kiick K L. Hydrophilic elastomeric biomaterials based on resilin-like polypeptides. Soft Matter 2009; 5, 3412-3416.
[19] Velema J, Kaplan D. Biopolymer-based biomaterials as scaffolds for tissue engineering. Tissue Engineering I: Scaffold Systems for Tissue Engineering 2006; 102: 187-238.
[20] Chen J M, Xu J K, Wang A L, Zheng M H. Scaffolds for tendon and ligament repair: review of the efficacy of commercial products. Expet Rev Med Dev 2009; 6: 61-73.
[21] Bailey A. The chemistry of natural enzyme-induced cross-links of proteins. Amino Acids 1991; 1: 293-306.
[22] Calabro A, Richard A G, Aniq B D. U.S. Pat. No. 6,982,298, 2006. [23] Chomczynski P, Sacchi N. Single-step method of RNA isolation by acid guanidinium thiocyanate-phenol-chloroform extraction. Anal Biochem 1987; 162: 156-159.
[24] Malencik D A, Anderson S R. Dityrosine Formation in Calmodulin: Cross-Linking and Polymerization Catalyzed by Arthromyces Peroxidase. Biochemistry 1996; 35: 4375-4386.
[25] Hu X, Kaplan D, Cebe P. Determining beta-sheet crystallinity in fibrous proteins by thermal analysis and infrared spectroscopy. Macromolecules 2006; 39: 6161-6170.
[26] Hu X, Kaplan D, Cebe P. Dynamic protein-water relationships during beta-sheet formation. Macromolecules 2008; 41: 3939-3948.
[27] Greenfield N J. Using circular dichroism spectra to estimate protein secondary structure. Nature Protocols 2006; 1: 2876-2890.
[28] Whitmore L, Wallace B A. DICHROWEB, an online server for protein secondary structure analyses from circular dichroism spectroscopic data. Nucleic Acids Res 2004; 32:W668-673.
[29] Whitmore L, Wallace B A. Protein Secondary Structure Analyses from Circular Dichroism Spectroscopy: Methods and Reference Databases. Biopolymers 2008; 89: 392-400.
[30] Huson M G, Maxwell J M. The measurement of resilience with a scanning probe microscope. Polymer Testing 2006; 25: 2-11.
[31] Neff D, Frazier S, Quimby L, Wang R, Zill S Identification of resilin in the leg of cockroach, *Periplaneta americana*: confirmation by a simple method using pH dependence of UV fluorescence. Arthropod Struct Dev 2000; 29: 75-83.
[32] Alper J. Stretching the Limits. Science 2002; 297: 329-330.
[33] Tatham A S, Shewry P R. Comparative Structures and Properties of Elastic Proteins. Phil Trans Roy Soc B 2002; 357: 229-234.
[34] Yoda R J. Elastomers for biomedical applications. Biomater Sci Polym Ed 1998; 9: 561-626.
[35] Martino M, Perri T, Tamburro A M. Biopolymers and biomaterials based on elastomeric proteins. Macromol Biosci 2002; 2: 319-328.
[36] Lyons R L, Lesieur E, Kim M, Wong DCC, Huson M G, Nairn K M, et al. Design and facile production of recombinant resilin-like polypeptides: gene construction and a rapid protein purification method. Protein Eng Des Sel 2007; 20: 25-32.
[37] Aaron B B, Gosline J M. Elastin as a random-network elastomer: A mechanical and optical analysis of single elastin fibers. Biopolymers 1981; 20; 1247-1260.
[38] Tamburro A M, Guantieri V, Pandolfo L, Scopa A. Synthetic fragments and analogues of elastin. II. Conformational studies. Biopolymers 1990; 29: 855-870.
[39] Andersen S O. Covalent Cross-Links in a Structural Protein, Resilin. Acta Physiol Scand Suppl 1966; 263: 1-81.
[40] Andersen S O. Crosslinks in Resilin Identified as Dityrosine and Trityrosine. Biochim Biophys Acta 1964; 93: 213-215.
[41] Coles G S. Studies on resilin biosynthesis. J Insect Physiol 1966; 12: 679-691.
[42] Giulivi C, Davies K. Mechanism of the formation and proteolytic release of $H_2O_2$-induced dityrosine and tyrosine oxidation products in hemoglobin and red blood cells. J Biol Chem 2001; 276: 24129.
[43] Loplrgolo L, Lugao A, Catalani L. Direct U V photocrosslinking of poly(N-vinyl-2-pyrrolidone)(PVP) to produce hydrogels. Polymer 2003; 44: 6217-6222.

[44] Ferradini C, Jay-Gerin J. The effect of pH on water radiolysis: a still open question—a minireview. Res Chem Intermed 2000; 26: 549-565.
[45] Fechine G, Barros J, Catalani L. Poly(N-vinyl-2-pyrrolidone) hydrogel production by ultraviolet radiation: new methodologies to accelerate crosslinking. Polymer 2004; 45: 4705-4709.
[46] Lewis S, Lynch A, Bachas L, Hampson S, Ormsbee L, Bhattacharyya D. Chelate-Modified Fenton Reaction for the Degradation of Trichloroethylene in Aqueous and Two-Phase Systems. Environ Eng Sci 2009; 26: 849-859.
[47] Katsumata H, Kaneco S, Suzuki T, Ohta K, Yobiko Y. Photo-Fenton degradation of alachlor in the presence of citrate solution. J Photochem Photobiol A: Chem 2006; 180: 38-45.
[48] Martens P, Grant M, Nilasaroya A, Whitelock J, Poole-Warren L. Characterisation of Redox Initiators for Producing Poly(Vinyl Alcohol) Hydrogels. Macromol Symp 2008; 266: 59-62.
[49] Makuuchi K. Critical review of radiation processing of hydrogel and polysaccharide. Radiat Phys Chem 2010; 79: 267-271.
[50] Mawad D, Martens P, Odell R, Poole-Warren L. The effect of redox polymerisation on degradation and cell responses to poly(vinyl alcohol) hydrogels. Biomaterials 2007; 28: 947-955.
[51] Barros J, Fechine G, Alcantara M, Catalani L. Poly(N-vinyl-2-pyrrolidone) hydrogels produced by Fenton reaction. Polymer 2006; 47: 8414-8419.
[52] Xu D, Hong J, Sheng K, Dong L, Yao S. Preparation of polyethyleneimine nanogels via photo-Fenton reaction. Radiat Phys Chem 2007; 76: 1606-1611.
[53] Giulivi C, Traaseth N, Davies K. Tyrosine oxidation products: analysis and biological relevance. Amino Acids 2003; 25: 227-232.
[54] Fancy D, Kodadek T. Chemistry for the analysis of protein—protein interactions: Rapid and efficient crosslinking triggered by long wavelength light. Proc Natl Acad Sci USA 1999; 96: 6020.
[55] Elvin C, Vuocolo T, Brownlee A, Sando L, Huson M, Liyou N, et al. A highly elastic tissue sealant based on photopolymerised gelatin. Biomaterials 2010; 31: 8323-8331.
[56] Lefebvre F, Droullet F, Savin de Larclasuse A M, Aprahamian M, Midy D, Bordenave L, et al. Repair of experimental arteriotomy in rabbit aorta using new resorbable elastin-fibrin biomaterial. J Biomed Mater Res 1989; 23: 1423-1432.
[57] Capello J, Crissman J, Dorman M, Mikolajczak M, Textor G, Marquet M, et al. Genetic engineering of structural protein polymers. Biotechnol Prog 1990; 6: 198-202.

---

What is claimed is:

1. A polymer having the general formula I:

A-L-B            Formula I wherein:
B is a biopolymer which is a polypeptide comprising at least one resilin amino acid sequence;
L is a linking moiety; and
A is a dihydroxyphenyl moiety having the general formula II:

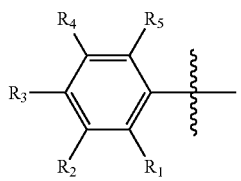

Formula II wherein each of $R_1$-$R_5$ is independently selected from the group consisting of hydrogen and hydroxyl, and at least two of $R_1$-$R_5$ are hydroxyl.

2. The polymer of claim 1, wherein at least one of $R_1$-$R_5$ is hydrogen.

3. The polymer of claim 1, wherein at least 90% of the total amount of dihydroxyphenyl moieties of the polymer are not crosslinked.

4. The polymer of claim 1, wherein said dihydroxyphenyl moiety and said linking moiety form a part of a DOPA residue.

5. The polymer of claim 1, wherein said dihydroxyphenyl moiety and said linking moiety do not form a part of a DOPA residue.

6. The polymer of claim 1, comprising a plurality of said dihydroxyphenyl moiety.

7. The polymer of claim 6, wherein a ratio of molecular weight of the polymer to dihydroxyphenyl moieties comprised by the polymer is in a range of from 1.5 KDa per dihydroxyphenyl moiety to 12 KDa per dihydroxyphenyl moiety.

8. The polymer of claim 6, being a polypeptide wherein a percentage of amino acid residues of said polypeptide which comprise said dihydroxyphenyl moiety is in a range of from 0.5% to 5%.

9. The polymer of claim 1, exhibiting an adhesiveness to a surface, said adhesiveness comprising resistance to stress of 1 KPa in a direction perpendicular to said surface.

10. A method of preparing the polymer of claim 5, wherein said linking moiety is attached to said biopolymer via a covalent bond formed between a reactive group in said linking moiety and a functional group on said biopolymer, the method comprising:
   a) providing a compound comprising said dihydroxyphenyl moiety and said reactive group; and
   b) contacting said compound with a biopolymer comprising at least one of said functional group, said biopolymer comprising at least one resilin amino acid sequence, to form said covalent bond,
   thereby preparing the polymer.

11. A method of preparing the polymer of claim 1, the method comprising:
   a) providing a biopolymer comprising at least one hydroxyphenyl moiety, said biopolymer comprising at least one resilin amino acid sequence; and
   b) oxidizing at least one of said at least one hydroxyphenyl moiety to form said dihydroxyphenyl moiety,
   thereby preparing the polymer.

12. The method of claim 11, wherein said oxidizing is effected by contacting said biopolymer with a tyrosine hydroxylase.

13. The method of claim 11, wherein at least 90% of the total amount of dihydroxyphenyl moieties of said polymer are not crosslinked.

14. The method of claim 11, wherein said oxidizing is effected by a Fenton reaction.

15. A method of generating a crosslinked adhesive, the method comprising contacting the polymer of claim 1 with an oxidizing agent, to thereby crosslink said dihydroxyphenyl moieties of said polymer.

16. A method of binding a first agent to a second agent, the method comprising contacting the first agent with said second agent in a presence of the polymer of claim 1 and an oxidizing agent.

17. The method of claim 15, wherein said contacting is effected in vivo.

18. A kit comprising:
a) an adhesive comprising the polymer of claim 1; and
b) an oxidizing agent.

19. A crosslinked polymer having the general formula III:

B'-L'-A'-A''-L''-B''     Formula III wherein:

B' and B'' are each independently a biopolymer which is a polypeptide comprising at least one resilin amino acid sequence;

L' and L'' are each a linking moiety; and

A'-A'' is a pair of crosslinked dihydroxyphenyl moieties, said pair having a formula selected from the group consisting of:

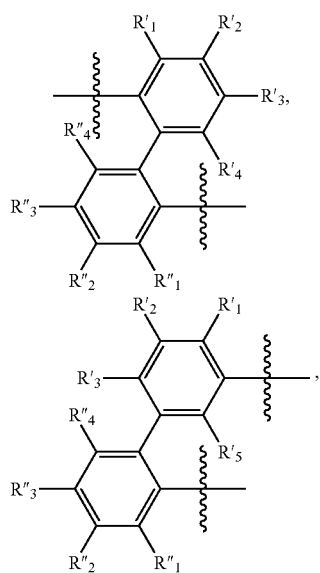

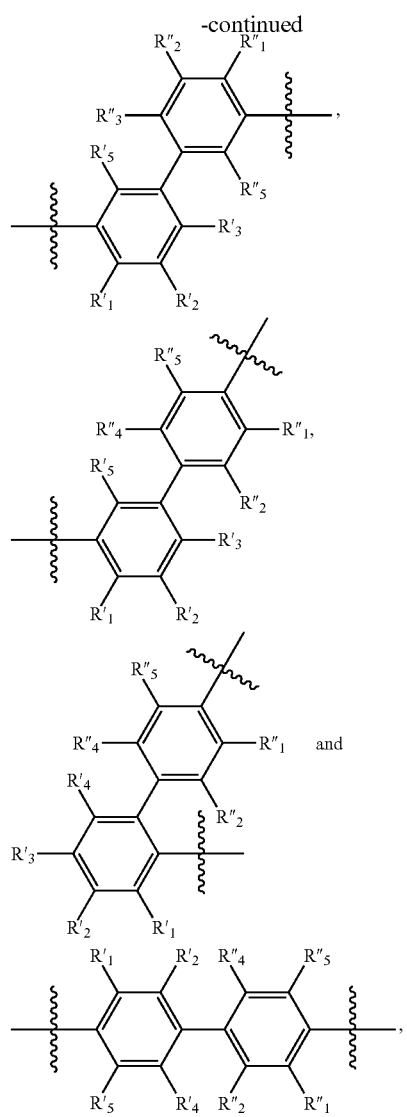

wherein each of $R'_1$-$R'_5$ and $R''_1$-$R''_5$ is independently selected from the group consisting of hydrogen and hydroxy, and at least two of $R'_1$-$R'_5$ and at least two of $R''_1$-$R''_5$ are hydroxy, with the proviso that said biopolymer is not blended with a polysaccharide.

20. The crosslinked polymer of claim 19, comprising a plurality of said pair of crosslinked dihydroxyphenyl moieties.

21. The crosslinked polymer of claim 19, exhibiting an adhesiveness to a surface, said adhesiveness comprising resistance to shear stress of 1.5 MPa.

22. The crosslinked polymer of claim 19, exhibiting an adhesiveness to a surface, said adhesiveness comprising resistance to stress of 10 KPa in a direction perpendicular to said surface.

SEQUENCE LISTING

```
<160> NUMBER OF SEQ ID NOS: 24

<210> SEQ ID NO 1
<211> LENGTH: 324
<212> TYPE: PRT
<213> ORGANISM: Artificial sequence
<220> FEATURE:
<223> OTHER INFORMATION: Drosophila melanogaster derived resilin exon 1

<400> SEQUENCE: 1

Met Gly Pro Glu Pro Val Asn Ser Tyr Leu Pro Pro Ser Asp Ser
1               5                   10                  15

Tyr Gly Ala Pro Gly Gln Ser Gly Pro Gly Gly Arg Pro Ser Asp Ser
                20                  25                  30

Tyr Gly Ala Pro Gly Gly Gly Asn Gly Gly Arg Pro Ser Asp Ser Tyr
            35                  40                  45

Gly Ala Pro Gly Gln Gly Gln Gly Gln Gly Gln Gly Gln Gly Gly Tyr
        50                  55                  60

Ala Gly Lys Pro Ser Asp Thr Tyr Gly Ala Pro Gly Gly Gly Asn Gly
65                  70                  75                  80

Asn Gly Gly Arg Pro Ser Ser Ser Tyr Gly Ala Pro Gly Gly Gly Asn
                85                  90                  95

Gly Gly Arg Pro Ser Asp Thr Tyr Gly Ala Pro Gly Gly Gly Asn Gly
            100                 105                 110

Gly Arg Pro Ser Asp Thr Tyr Gly Ala Pro Gly Gly Gly Asn Gly
        115                 120                 125

Asn Gly Gly Arg Pro Ser Ser Ser Tyr Gly Ala Pro Gly Gln Gly Gln
    130                 135                 140

Gly Asn Gly Asn Gly Gly Arg Ser Ser Ser Tyr Gly Ala Pro Gly
145                 150                 155                 160

Gly Gly Asn Gly Gly Arg Pro Ser Asp Thr Tyr Gly Ala Pro Gly Gly
                165                 170                 175

Gly Asn Gly Gly Arg Pro Ser Asp Thr Tyr Gly Ala Pro Gly Gly Gly
```

```
                180                 185                 190
Asn Asn Gly Gly Arg Pro Ser Ser Tyr Gly Ala Pro Gly Gly Gly
            195                 200                 205

Asn Gly Gly Arg Pro Ser Asp Thr Tyr Gly Ala Pro Gly Gly Asn
            210                 215                 220

Gly Asn Gly Ser Gly Gly Arg Pro Ser Ser Tyr Gly Ala Pro Gly
225                 230                 235                 240

Gln Gly Gln Gly Gly Phe Gly Gly Arg Pro Ser Asp Ser Tyr Gly Ala
            245                 250                 255

Pro Gly Gln Asn Gln Lys Pro Ser Asp Ser Tyr Gly Ala Pro Gly Ser
            260                 265                 270

Gly Asn Gly Asn Gly Gly Arg Pro Ser Ser Tyr Gly Ala Pro Gly
            275                 280                 285

Ser Gly Pro Gly Gly Arg Pro Ser Asp Ser Tyr Gly Pro Pro Ala Ser
            290                 295                 300

Gly Ser Gly Ala Gly Gly Ala Gly Gly Ser Gly Pro Gly Gly Ala Asp
305                 310                 315                 320

Tyr Asp Asn Asp

<210> SEQ ID NO 2
<211> LENGTH: 323
<212> TYPE: PRT
<213> ORGANISM: Artificial sequence
<220> FEATURE:
<223> OTHER INFORMATION: Drosophila melanogaster derived resilin exon 1

<400> SEQUENCE: 2

Gly Pro Glu Pro Pro Val Asn Ser Tyr Leu Pro Pro Ser Asp Ser Tyr
1               5                   10                  15

Gly Ala Pro Gly Gln Ser Gly Pro Gly Gly Arg Pro Ser Asp Ser Tyr
            20                  25                  30

Gly Ala Pro Gly Gly Gly Asn Gly Gly Arg Pro Ser Asp Ser Tyr Gly
            35                  40                  45

Ala Pro Gly Gln Gly Gln Gly Gln Gly Gln Gly Gly Tyr Ala
            50                  55                  60

Gly Lys Pro Ser Asp Thr Tyr Gly Ala Pro Gly Gly Asn Gly Asn
65                  70                  75                  80

Gly Gly Arg Pro Ser Ser Tyr Gly Ala Pro Gly Gly Asn Gly
            85                  90                  95

Gly Arg Pro Ser Asp Thr Tyr Gly Ala Pro Gly Gly Asn Gly Gly
            100                 105                 110

Arg Pro Ser Asp Thr Tyr Gly Ala Pro Gly Gly Gly Asn Gly Asn
            115                 120                 125

Gly Gly Arg Pro Ser Ser Tyr Gly Ala Pro Gly Gln Gly Gln Gly
            130                 135                 140

Asn Gly Asn Gly Gly Arg Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
            165                 170                 175

Asn Gly Gly Arg Pro Ser Asp Thr Tyr Gly Ala Pro Gly Gly Gly Asn
            180                 185                 190

Asn Gly Gly Arg Pro Ser Ser Tyr Gly Ala Pro Gly Gly Gly Asn
            195                 200                 205

Gly Gly Arg Pro Ser Asp Thr Tyr Gly Ala Pro Gly Gly Gly Asn Gly
            210                 215                 220
```

```
Asn Gly Ser Gly Gly Arg Pro Ser Ser Tyr Gly Ala Pro Gly Gln
225                 230                 235                 240

Gly Gln Gly Gly Phe Gly Arg Pro Ser Asp Ser Tyr Gly Ala Pro
                245                 250                 255

Gly Gln Asn Gln Lys Pro Ser Asp Ser Tyr Gly Ala Pro Gly Ser
            260                 265                 270

Asn Gly Asn Gly Arg Pro Ser Ser Tyr Gly Ala Pro Gly Ser
        275                 280                 285

Gly Pro Gly Gly Arg Pro Ser Asp Ser Tyr Gly Pro Pro Ala Ser Gly
    290                 295                 300

Ser Gly Ala Gly Gly Ala Gly Ser Gly Pro Gly Ala Asp Tyr
305                 310                 315                 320

Asp Asn Asp

<210> SEQ ID NO 3
<211> LENGTH: 62
<212> TYPE: PRT
<213> ORGANISM: Artificial sequence
<220> FEATURE:
<223> OTHER INFORMATION: Chitin binding sequence

<400> SEQUENCE: 3

Glu Pro Ala Lys Tyr Glu Phe Asn Tyr Gln Val Glu Asp Ala Pro Ser
1               5                   10                  15

Gly Leu Ser Phe Gly His Ser Glu Met Arg Asp Gly Asp Phe Thr Thr
            20                  25                  30

Gly Gln Tyr Asn Val Leu Leu Pro Asp Gly Arg Lys Gln Ile Val Glu
        35                  40                  45

Tyr Glu Ala Asp Gln Gln Gly Tyr Arg Pro Gln Ile Arg Tyr
    50                  55                  60

<210> SEQ ID NO 4
<211> LENGTH: 15
<212> TYPE: PRT
<213> ORGANISM: Artificial sequence
<220> FEATURE:
<223> OTHER INFORMATION: Resilin repeating unit

<400> SEQUENCE: 4

Gly Gly Arg Pro Ser Asp Ser Tyr Gly Ala Pro Gly Gly Gly Asn
1               5                   10                  15

<210> SEQ ID NO 5
<211> LENGTH: 9
<212> TYPE: PRT
<213> ORGANISM: Artificial sequence
<220> FEATURE:
<223> OTHER INFORMATION: Resilin repeating unit

<400> SEQUENCE: 5

Gly Arg Pro Ser Asp Ser Tyr Gly Ala
1               5

<210> SEQ ID NO 6
<211> LENGTH: 74
<212> TYPE: PRT
<213> ORGANISM: Artificial sequence
<220> FEATURE:
<223> OTHER INFORMATION: Chitin binding sequence

<400> SEQUENCE: 6
```

-continued

Pro Ala Lys Tyr Glu Phe Asn Tyr Gln Val Glu Asp Ala Pro Ser Gly
1               5                   10                  15

Leu Ser Phe Gly His Ser Glu Met Arg Asp Gly Asp Phe Thr Thr Gly
            20                  25                  30

Gln Tyr Asn Val Leu Leu Pro Asp Gly Arg Lys Gln Ile Val Glu Tyr
        35                  40                  45

Glu Ala Asp Gln Gln Gly Tyr Arg Pro Gln Ile Arg Tyr Glu Gly Asp
    50                  55                  60

Ala Asn Asp Gly Ser Gly Pro Ser Gly Pro
65                  70

<210> SEQ ID NO 7
<211> LENGTH: 900
<212> TYPE: DNA
<213> ORGANISM: Artificial sequence
<220> FEATURE:
<223> OTHER INFORMATION: Examples of polynucleotides which can be used
      to express resilin

<400> SEQUENCE: 7
agctatggag caccgggtca gagtggtccc ggcggcaggc cgtcggattc ctatggagct      60
cctggtggtg aaacggtgg acggccctca gacagctatg gcgctccagg ccagggtcaa     120
ggacagggac aaggacaagg tggatatgca ggcaagccct cagatacct tggagctcct      180
ggtggtggaa atggcaacgg aggtcgtcca tcgagcagct atggcgctcc tggcggtgga    240
aacggtggtc gtccttcgga tacctacggt gctcctggtg cggaaatgg tggacgccca     300
tcggacactt atggtgctcc tggtggtggt ggaaatggca acggcggacg accttcaagc    360
agctatggag ctcctggtca aggacaaggc aacggaaatg gcggtcgctc atcgagcagc    420
tatggtgctc ctggcggtgg aaacggcggt cgtccttcgg atacctacgg tgctcccggt    480
ggtggaaacg gtggtcgtcc ttcggatact tacgcgctc ctggtggcgg caataatggc    540
ggtcgtccct caagcagcta cggcgctcct ggtggtggaa acggtggtcg tccatctgac    600
acctatggcg ctcctggtgg cggtaacgga aacggcagcg gtggtcgtcc ttcaagcagc    660
tatggagctc ctggtcaggg ccaaggtgga tttggtggtc gtccatcgga ctcctatggt    720
gctcctggtc agaaccaaaa accatcagat tcatatggcg cccctggtag cggcaatggc    780
aacggcggac gtccttcgag cagctatgga gctccaggct caggacctgg tggccgaccc    840
tccgactcct acggacccc agcttctgga tcggagcag gtggcgctgg aggcagtgga    900

<210> SEQ ID NO 8
<211> LENGTH: 20
<212> TYPE: PRT
<213> ORGANISM: Artificial sequence
<220> FEATURE:
<223> OTHER INFORMATION: A sequence derived from resilin exon 1

<400> SEQUENCE: 8

Met Val Arg Pro Glu Pro Pro Val Asn Ser Tyr Leu Pro Pro Ser Asp
1               5                   10                  15

Ser Tyr Gly Ala
            20

<210> SEQ ID NO 9
<211> LENGTH: 20
<212> TYPE: PRT
<213> ORGANISM: Artificial sequence
<220> FEATURE:
<223> OTHER INFORMATION: A sequence derived from resilin exon 1

<400> SEQUENCE: 9

Met Gly Ile Val Glu Tyr Glu Ala Asp Gln Gln Gly Tyr Arg Pro Gln
1               5                   10                  15

Ile Arg Tyr Glu
            20

<210> SEQ ID NO 10
<211> LENGTH: 11
<212> TYPE: PRT
<213> ORGANISM: Artificial sequence
<220> FEATURE:
<223> OTHER INFORMATION: A repeat sequence of a synthetic proresilin
      (AN16) derived from Anopheles gambiae

<400> SEQUENCE: 10

Ala Gln Thr Pro Ser Ser Gln Tyr Gly Ala Pro
1               5                   10

<210> SEQ ID NO 11
<211> LENGTH: 1080
<212> TYPE: DNA
<213> ORGANISM: Artificial sequence
<220> FEATURE:
<223> OTHER INFORMATION: An exemplary DNA sequence of 6H-tagged resilin
      (exon 1)

<400> SEQUENCE: 11

```
atgtcgtact accatcacca tcaccatcac gattacgata tcccaacgac cgaaaacctg      60
tattttcagg gcgccatggg accggagcca ccagttaact cgtatctacc tccgtccgat     120
agctatggag caccgggtca gagtggtccc ggcggcaggc cgtcggattc ctatggagct     180
cctggtggtg aaacggtgg acggccctca gacagctatg cgctccagg ccagggtcaa      240
ggacagggac aaggacaagg tggatatgca ggcaagccct cagataccta tggagctcct     300
ggtggtggaa atggcaacgg aggtcgtcca tcgagcagct atggcgctcc tggcggtgga     360
aacggtggtc gtccttcgga tacctacggt gctcctggtg gcggaaatgg tggacgccca     420
tcggacactt atggtgctcc tggtggtggt ggaaatggca acggcggacg accttcaagc     480
agctatggag ctcctggtca aggacaaggc aacggaaatg gcggtcgctc atcgagcagc     540
tatggtgctc ctggcggtgg aaacggcggt cgtccttcgg atacctacgg tgctcccggt     600
ggtggaaacg gtggtcgtcc ttcggatact tacgcgctc ctggtggcgg caataatggc      660
ggtcgtccct caagcagcta cggcgctcct ggtggtggaa acggtggtcg tccatctgac     720
acctatggcg ctcctggtgg cggtaacgga aacggcagcg gtggtcgtcc ttcaagcagc     780
tatggagctc ctggtcaggg ccaaggtgga tttggtggtc gtccatcgga ctcctatggt     840
gctcctggtc agaaccaaaa accatcagat tcatatggcg cccctggtag cggcaatggc     900
aacggcggac gtccttcgag cagctatgga gctccaggct caggacctgg tggccgaccc     960
tccgactcct acggaccccc agcttctgga tcggagcag gtggcgctgg aggcagtgga    1020
cccggcggcg ctgactacga taacgatgag ggatccaatc actagtgaat tcgcggccgc    1080
```

<210> SEQ ID NO 12
<211> LENGTH: 354
<212> TYPE: PRT
<213> ORGANISM: Artificial sequence
<220> FEATURE:
<223> OTHER INFORMATION: An exemplary [protein sequence of 6H-tagged
      resilin (exon 1)

```
<400> SEQUENCE: 12

Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
            35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Tyr Ala Gly Lys Pro Ser Asp Thr
                85                  90                  95

Tyr Gly Ala Pro Gly Gly Gly Asn Gly Asn Gly Arg Pro Ser Ser
                100                 105                 110

Ser Tyr Gly Ala Pro Gly Gly Gly Asn Gly Gly Arg Pro Ser Asp Thr
            115                 120                 125

Tyr Gly Ala Pro Gly Gly Gly Asn Gly Gly Arg Pro Ser Asp Thr Tyr
    130                 135                 140

Gly Ala Pro Gly Gly Gly Asn Gly Asn Gly Arg Pro Ser Ser
145                 150                 155                 160

Ser Tyr Gly Ala Pro Gly Gln Gly Gln Gly Asn Gly Asn Gly Arg
                165                 170                 175

Ser Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Gly Arg Pro Ser
    195                 200                 205

Asp Thr Tyr Gly Ala Pro Gly Gly Gly Asn Asn Gly Gly Arg Pro Ser
        210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
            245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
            275                 280                 285

Ser Asp Ser Tyr Gly Ala Pro Gly Ser Gly Asn Gly Asn Gly Arg
290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
            325                 330                 335

Gly Gly Ser Gly Pro Gly Gly Ala Asp Tyr Asp Asn Asp Glu Gly Ser
            340                 345                 350

Asn His

<210> SEQ ID NO 13
<211> LENGTH: 1311
<212> TYPE: DNA
<213> ORGANISM: Artificial sequence
<220> FEATURE:
<223> OTHER INFORMATION: An exemplary DNA sequence of 6H-tagged
      resilin (exons 1 and 2)
```

-continued

<400> SEQUENCE: 13

```
catatgtcgt actaccatca ccatcaccat cacgattacg atatcccaac gaccgaaaac    60
ctgtattttc agggcgccat gggaccggag ccaccagtta actcgtatct acctccgtcc   120
gatagctatg gagcaccggg tcagagtggt cccggcggca ggccgtcgga ttcctatgga   180
gctcctggtg gtggaaacgg tggacggccc tcagacagct atggcgctcc aggccagggt   240
caaggacagg gacaaggaca aggtggatat gcaggcaagc cctcagatac ctatggagct   300
cctggtggtg gaaatggcaa cggaggtcgt ccatcgagca gctatggcgc tcctggcggt   360
ggaaacggtg gtcgtccttc ggatacctac ggtgctcctg gtggcggaaa tggtggacgc   420
ccatcggaca cttatggtgc tcctggtggt ggtggaaatg gcaacggcgg acgaccttca   480
agcagctatg gagctcctgg tcaaggacaa ggcaacggaa atggcggtcg ctcatcgagc   540
agctatggtg ctcctggcgg tggaaacggc ggtcgtcctt cggatacctc cggtgctccc   600
ggtggtggaa acggtggtcg tccttcggat acttacggcg ctcctggtgg cggcaataat   660
ggcggtcgtc cctcaagcag ctacggcgct cctggtggtg gaaacggtgg tcgtccatct   720
gacacctatg gcgctcctgg tggcggtaac ggaaacggca gcggtggtcg tccttcaagc   780
agctatggag ctcctggtca gggccaaggt ggatttggtg gtcgtccatc ggactcctat   840
ggtgctcctg gtcagaacca aaaaccatca gattcatatg gcgcccctgg tagcggcaat   900
ggcaacggcg gacgtccttc gagcagctat ggagctccag gctcaggacc tggtggccga   960
ccctccgact cctacggacc cccagcttct ggatcgggag caggtggcgc tggaggcagt  1020
ggacccggcg gcgctgacta cgataacgat gagcccgcca agtacgaatt taattaccag  1080
gttgaggacg cgcccagcgg actctcgttc gggcattcag agatgcgcga cggtgacttc  1140
accaccggcc agtacaatgt cctgttgccc gacggaagga agcaaattgt ggagtatgaa  1200
gccgaccagc agggctaccg gccacagatc cgctacgaag gcgatgccaa cgatggcagt  1260
ggtcccagcg gtccttaagg atccgagctc cgtcgacaag cttgcggccg c           1311
```

<210> SEQ ID NO 14
<211> LENGTH: 424
<212> TYPE: PRT
<213> ORGANISM: Artificial sequence
<220> FEATURE:
<223> OTHER INFORMATION: An exemplary protein sequence of 6H-tagged resilin (exons 1 and 2)

<400> SEQUENCE: 14

Met Ser Tyr Tyr His His His His His His Asp Tyr Asp Ile Pro Thr
1               5                   10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Gly Tyr Ala Gly Lys Pro Ser Asp Thr
                85                  90                  95

Tyr Gly Ala Pro Gly Gly Gly Asn Gly Asn Gly Gly Arg Pro Ser Ser
            100                 105                 110

Ser Tyr Gly Ala Pro Gly Gly Gly Asn Gly Gly Arg Pro Ser Asp Thr

-continued

```
                115                 120                 125
Tyr Gly Ala Pro Gly Gly Gly Asn Gly Gly Arg Pro Ser Asp Thr Tyr
        130                 135                 140
Gly Ala Pro Gly Gly Gly Asn Gly Asn Gly Gly Arg Pro Ser Ser
145                 150                 155                 160
Ser Tyr Gly Ala Pro Gly Gln Gly Gln Gly Asn Gly Asn Gly Gly Arg
            165                 170                 175
Ser Ser Ser Ser Tyr Gly Ala Pro Gly Gly Asn Gly Gly Arg Pro
        180                 185                 190
Ser Asp Thr Tyr Gly Ala Pro Gly Gly Asn Gly Gly Arg Pro Ser
        195                 200                 205
Asp Thr Tyr Gly Ala Pro Gly Gly Gly Asn Asn Gly Gly Arg Pro Ser
    210                 215                 220
Ser Ser Tyr Gly Ala Pro Gly Gly Gly Asn Gly Gly Arg Pro Ser Asp
225                 230                 235                 240
Thr Tyr Gly Ala Pro Gly Gly Gly Asn Gly Asn Gly Ser Gly Arg
                245                 250                 255
Pro Ser Ser Ser Tyr Gly Ala Pro Gly Gln Gly Gln Gly Gly Phe Gly
            260                 265                 270
Gly Arg Pro Ser Asp Ser Tyr Gly Ala Pro Gly Gln Asn Gln Lys Pro
        275                 280                 285
Ser Asp Ser Tyr Gly Ala Pro Gly Ser Gly Asn Gly Asn Gly Gly Arg
    290                 295                 300
Pro Ser Ser Ser Tyr Gly Ala Pro Gly Ser Gly Pro Gly Gly Arg Pro
305                 310                 315                 320
Ser Asp Ser Tyr Gly Pro Pro Ala Ser Gly Ser Gly Ala Gly Ala
                325                 330                 335
Gly Gly Ser Gly Pro Gly Gly Ala Asp Tyr Asp Asn Asp Glu Pro Ala
            340                 345                 350
Lys Tyr Glu Phe Asn Tyr Gln Val Glu Asp Ala Pro Ser Gly Leu Ser
        355                 360                 365
Phe Gly His Ser Glu Met Arg Asp Gly Asp Phe Thr Thr Gly Gln Tyr
    370                 375                 380
Asn Val Leu Leu Pro Asp Gly Arg Lys Gln Ile Val Glu Tyr Glu Ala
385                 390                 395                 400
Asp Gln Gln Gly Tyr Arg Pro Gln Ile Arg Tyr Glu Gly Asp Ala Asn
                405                 410                 415
Asp Gly Ser Gly Pro Ser Gly Pro
            420
```

<210> SEQ ID NO 15
<211> LENGTH: 1580
<212> TYPE: DNA
<213> ORGANISM: Artificial sequence
<220> FEATURE:
<223> OTHER INFORMATION: An exemplary DNA sequence of 6H-tagged resilin
     (exon 1) fused to a cellulose-binding domain (CBD)

<400> SEQUENCE: 15

```
catatgtcgt actaccatca ccatcaccat cacgattacg atatcccaac gaccgaaaac    60 ctgtatttc agggcgccat gggaccggag ccaccagtta actcgtatct acctccgtcc   120
gatagctatg gagcaccggg tcagagtggt cccggcggca ggccgtcgga ttcctatgga   180
gctcctggtg gtggaaacgg tggacggccc tcagacagct atggcgctcc aggccagggt   240
caaggacagg gacaaggaca aggtggatat gcaggcaagc cctcagatac ctatggagct   300
```

```
cctggtggtg gaaatggcaa cggaggtcgt ccatcgagca gctatggcgc tcctggcggt    360
ggaaacggtg gtcgtccttc ggatacctac ggtgctcctg gtggcggaaa tggtggacgc    420
ccatcggaca cttatggtgc tcctggtggt ggtggaaatg gcaacggcgg acgaccttca    480
agcagctatg gagctcctgg tcaaggacaa ggcaacggaa atggcggtcg ctcatcgagc    540
agctatggtg ctcctggcgg tggaaacggc ggtcgtcctt cggatacctt cggtgctccc    600
ggtggtggaa acggtggtcg tccttcggat acttacggcg ctcctggtgg cggcaataat    660
ggcggtcgtc cctcaagcag ctacggcgct cctggtggtg aaacggtgg tcgtccatct    720 gacacctatg cgctcctggt ggcggtaac ggaaacggca gcgtggtcg tccttcaagc    780 agctatggag ctcctggtca gggccaaggt ggatttggtg tcgtccatc ggactcctat    840 ggtgctcctg gtcagaacca aaaccatca gattcatatg cgccctgg tagcggcaat    900 ggcaacggcg gacgtccttc gagcagctat ggagctccag gctcaggacc tggtggccga    960
ccctccgact cctacggacc cccagcttct ggatcgggag caggtggcgc tggaggcagt   1020
ggacccggcg gcgctgacta cgataacgat gaggggatcc ccgaccccgg catggcagcg   1080
acatcatcaa tgtcagttga atttacaac tctaacaaat cagcacaaac aaactcaatt   1140
acaccaataa tcaaaattac taacacatct gacagtgatt taaatttaaa tgacgtaaaa   1200
gttagatatt attacacaag tgatggtaca caaggacaaa ctttctggtg tgaccatgct   1260
ggtgcattat taggaaatag ctatgttgat aacactagca aagtgacagc aaacttcgtt   1320
aaagaaacag caagcccaac atcaacctat gatacatatg ttgaattgg atttgcaagc   1380 ggacgagcta ctcttaaaaa aggacaattt ataactattc aaggaagaat aacaaaatca   1440
gactggtcaa actacactca acaaatgac tattcatttg atgcaagtag ttcaacacca   1500
gttgtaaatc caaaagttac aggatatata ggtgagcta aagtacttgg tacagcacca   1560
taggatcgat ccagatgtac                                              1580
```

<210> SEQ ID NO 16
<211> LENGTH: 519
<212> TYPE: PRT
<213> ORGANISM: Artificial sequence
<220> FEATURE:
<223> OTHER INFORMATION: An exemplary protein sequence of 6H-tagged
resilin (exon 1) fused to a cellulose-binding domain (CBD)

<400> SEQUENCE: 16

```
Met Ser Tyr Tyr His His His His His His Asp Tyr Asp Ile Pro Thr
1               5                  10                  15

Thr Glu Asn Leu Tyr Phe Gln Gly Ala Met Gly Pro Glu Pro Pro Val
            20                  25                  30

Asn Ser Tyr Leu Pro Pro Ser Asp Ser Tyr Gly Ala Pro Gly Gln Ser
        35                  40                  45

Gly Pro Gly Gly Arg Pro Ser Asp Ser Tyr Gly Ala Pro Gly Gly Gly
    50                  55                  60

Asn Gly Gly Arg Pro Ser Asp Ser Tyr Gly Ala Pro Gly Gln Gly Gln
65                  70                  75                  80

Gly Gln Gly Gln Gly Gln Gly Gly Tyr Ala Gly Lys Pro Ser Asp Thr
                85                  90                  95

Tyr Gly Ala Pro Gly Gly Gly Asn Gly Asn Gly Gly Arg Pro Ser Ser
            100                 105                 110

Ser Tyr Gly Ala Pro Gly Gly Gly Asn Gly Gly Arg Pro Ser Asp Thr
        115                 120                 125
```

```
Tyr Gly Ala Pro Gly Gly Gly Asn Gly Gly Arg Pro Ser Asp Thr Tyr
            130                 135                 140

Gly Ala Pro Gly Gly Gly Asn Gly Asn Gly Gly Arg Pro Ser Ser
145                 150                 155                 160

Ser Tyr Gly Ala Pro Gly Gln Gly Gln Gly Asn Gly Asn Gly Gly Arg
                165                 170                 175

Ser Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Gly Arg Pro Ser
        195                 200                 205

Asp Thr Tyr Gly Ala Pro Gly Gly Gly Asn Asn Gly Gly Arg Pro Ser
    210                 215                 220

Ser Ser Tyr Gly Ala Pro Gly Gly Gly Asn Gly Gly Arg Pro Ser Asp
225                 230                 235                 240

Thr Tyr Gly Ala Pro Gly Gly Gly Asn Gly Asn Gly Ser Gly Gly Arg
                245                 250                 255

Pro Ser Ser Ser Tyr Gly Ala Pro Gly Gln Gly Gln Gly Gly Phe Gly
            260                 265                 270

Gly Arg Pro Ser Asp Ser Tyr Gly Ala Pro Gly Gln Asn Gln Lys Pro
            275                 280                 285

Ser Asp Ser Tyr Gly Ala Pro Gly Ser Gly Asn Gly Asn Gly Gly Arg
        290                 295                 300

Pro Ser Ser Ser Tyr Gly Ala Pro Gly Ser Gly Pro Gly Gly Arg Pro
305                 310                 315                 320

Ser Asp Ser Tyr Gly Pro Pro Ala Ser Gly Ser Gly Ala Gly Gly Ala
            325                 330                 335

Gly Gly Ser Gly Pro Gly Gly Ala Asp Tyr Asp Asn Asp Glu Gly Ile
        340                 345                 350

Pro Asp Pro Gly Met Ala Ala Thr Ser Ser Met Ser Val Glu Phe Tyr
    355                 360                 365

Asn Ser Asn Lys Ser Ala Gln Thr Asn Ser Ile Thr Pro Ile Ile Lys
370                 375                 380

Ile Thr Asn Thr Ser Asp Ser Asp Leu Asn Leu Asn Asp Val Lys Val
385                 390                 395                 400

Arg Tyr Tyr Tyr Thr Ser Asp Gly Thr Gln Gly Gln Thr Phe Trp Cys
                405                 410                 415

Asp His Ala Gly Ala Leu Leu Gly Asn Ser Tyr Val Asp Asn Thr Ser
            420                 425                 430

Lys Val Thr Ala Asn Phe Val Lys Glu Thr Ala Ser Pro Thr Ser Thr
        435                 440                 445

Tyr Asp Thr Tyr Val Glu Phe Gly Phe Ala Ser Gly Arg Ala Thr Leu
    450                 455                 460

Lys Lys Gly Gln Phe Ile Thr Ile Gln Gly Arg Ile Thr Lys Ser Asp
465                 470                 475                 480

Trp Ser Asn Tyr Thr Gln Thr Asn Asp Tyr Ser Phe Asp Ala Ser Ser
                485                 490                 495

Ser Thr Pro Val Val Asn Pro Lys Val Thr Gly Tyr Ile Gly Gly Ala
            500                 505                 510

Lys Val Leu Gly Thr Ala Pro
            515

<210> SEQ ID NO 17
<211> LENGTH: 1620
```

<212> TYPE: DNA
<213> ORGANISM: Artificial sequence
<220> FEATURE:
<223> OTHER INFORMATION: An exemplary DNA sequence of 6H-tagged resilin
(exon 1) fused to a cellulose-binding domain (CBD)

<400> SEQUENCE: 17

| | |
|---|---|
| catatgtcgt actaccatca ccatcaccat cacgattacg atatcccaac gaccgaaaac | 60 |
| ctgtattttc agggcgccat ggcagcgaca tcatcaatgt cagttgaatt ttacaactct | 120 |
| aacaaagcag cacaaacaaa ctcaattaca ccaataatca aaattactaa cacagctgac | 180 |
| agtgatttaa atttaaatga cgtaaaagtt agatattatt acacaagtga tggtacacaa | 240 |
| ggacaaactt tctggggtga tcatgctggt gcattattag gaaatagcta tgttgataac | 300 |
| actggcaaag tgacagcaaa cttcgttaaa gaaacagcaa gcccaacatc aacctatgat | 360 |
| acatatgttg aatttggatt tgcaagcgga gcagctactc ttaaaaaagg acaatttata | 420 |
| actattcaag aagaataac aaaatcagac tggtcaaact acgctcagac aaatgactat | 480 |
| tcatttgatg caagtagttc aacaccagtt gtaaatccaa aagttacagg atatataggt | 540 |
| ggagctaaag tacttggtac agcaccaggt ccagatgtac catcttcaat aattaatcct | 600 |
| acttctgcaa catttgatcc ggagccacca gttaactcgt atctacctcc gtccgatagc | 660 |
| tatggagcac cgggtcagag tggtcccggc ggcaggccgt cggattccta tggagctcct | 720 |
| ggtggtggaa acggtggacg gccctcagac agctatggcg ctccaggcca gggtcaagga | 780 |
| cagggacaag gacaaggtgg atatgcaggc aagccctcag ataccatgg agctcctggt | 840 |
| ggtggaaatg gcaacggagg tcgtccatcg agcagctatg gcgctcctgg cggtggaaac | 900 |
| ggtggtcgtc cttcggatac ctacggtgct cctggtggcg gaaatggtgg acgcccatcg | 960 |
| gacacttatg gtgctcctgg tggtggtgga aatggcaacg gcggacgacc ttcaagcagc | 1020 |
| tatggagctc ctggtcaagg acaaggcaac ggaaatggcg gtcgctcatc gagcagctat | 1080 |
| ggtgctcctg gcggtggaaa cggcggtcgt ccttcggata cctacggtgc tcccggtggt | 1140 |
| ggaaacggtg gtcgtccttc ggatacttac ggcgctcctg gtggcggcaa taatggcggt | 1200 |
| cgtccctcaa gcagctacgg cgctcctggt ggtggaaacg gtggtcgtcc atctgacacc | 1260 |
| tatggcgctc tggtggcgg taacggaaac ggcagcggtg gtcgtccttc aagcagctat | 1320 |
| ggagctcctg gtcagggcca aggtggattt ggtggtcgtc catcggactc ctatggtgct | 1380 |
| cctggtcaga accaaaaacc atcagattca tatggcgccc ctggtagcgg caatggcaac | 1440 |
| ggcggacgtc cttcgagcag ctatggagct ccaggctcag gacctggtgg ccgaccctcc | 1500 |
| gactcctacg gacccccagc ttctggatcg ggagcaggtg gcgctggagg cagtggaccc | 1560 |
| ggcggcgctg actacgataa cgatgagtaa ggatccgagc tccgtcgaca agcttgcggc | 1620 |

<210> SEQ ID NO 18
<211> LENGTH: 528
<212> TYPE: PRT
<213> ORGANISM: Artificial sequence
<220> FEATURE:
<223> OTHER INFORMATION: An exemplary protein sequence of 6H-tagged
resilin (exon 1) fused to a cellulose-binding domain (CBD)

<400> SEQUENCE: 18

Met Ser Tyr Tyr His His His His His His Asp Tyr Asp Ile Pro Thr
1               5                   10                  15

Thr Glu Asn Leu Tyr Phe Gln Gly Ala Met Ala Ala Thr Ser Ser Met
            20                  25                  30

-continued

```
Ser Val Glu Phe Tyr Asn Ser Asn Lys Ala Ala Gln Thr Asn Ser Ile
             35                  40                  45

Thr Pro Ile Ile Lys Ile Thr Asn Thr Ala Asp Ser Asp Leu Asn Leu
 50                  55                  60

Asn Asp Val Lys Val Arg Tyr Tyr Thr Ser Asp Gly Thr Gln Gly
 65                  70                  75                  80

Gln Thr Phe Trp Gly Asp His Ala Gly Ala Leu Leu Gly Asn Ser Tyr
                 85                  90                  95

Val Asp Asn Thr Gly Lys Val Thr Ala Asn Phe Val Lys Glu Thr Ala
            100                 105                 110

Ser Pro Thr Ser Thr Tyr Asp Thr Tyr Val Glu Phe Gly Phe Ala Ser
            115                 120                 125

Gly Ala Ala Thr Leu Lys Lys Gly Gln Phe Ile Thr Ile Gln Gly Arg
            130                 135                 140

Ile Thr Lys Ser Asp Trp Ser Asn Tyr Ala Gln Thr Asn Asp Tyr Ser
145                 150                 155                 160

Phe Asp Ala Ser Ser Ser Thr Pro Val Val Asn Pro Lys Val Thr Gly
                165                 170                 175

Tyr Ile Gly Gly Ala Lys Val Leu Gly Thr Ala Pro Gly Pro Asp Val
            180                 185                 190

Pro Ser Ser Ile Ile Asn Pro Thr Ser Ala Thr Phe Asp Pro Glu Pro
            195                 200                 205

Pro Val Asn Ser Tyr Leu Pro Pro Ser Asp Ser Tyr Gly Ala Pro Gly
            210                 215                 220

Gln Ser Gly Pro Gly Gly Arg Pro Ser Asp Ser Tyr Gly Ala Pro Gly
225                 230                 235                 240

Gly Gly Asn Gly Gly Arg Pro Ser Asp Ser Tyr Gly Ala Pro Gly Gln
                245                 250                 255

Gly Gln Gly Gln Gly Gln Gly Gln Gly Gly Tyr Ala Gly Lys Pro Ser
            260                 265                 270

Asp Thr Tyr Gly Ala Pro Gly Gly Gly Asn Gly Asn Gly Gly Arg Pro
            275                 280                 285

Ser Ser Ser Tyr Gly Ala Pro Gly Gly Gly Asn Gly Gly Arg Pro Ser
            290                 295                 300

Asp Thr Tyr Gly Ala Pro Gly Gly Gly Asn Gly Gly Arg Pro Ser Asp
305                 310                 315                 320

Thr Tyr Gly Ala Pro Gly Gly Gly Gly Asn Gly Asn Gly Gly Arg Pro
                325                 330                 335

Ser Ser Ser Tyr Gly Ala Pro Gly Gln Gly Gln Gly Asn Gly Asn Gly
            340                 345                 350

Gly Arg Ser Ser Ser Ser Tyr Gly Ala Pro Gly Gly Gly Asn Gly Gly
            355                 360                 365

Arg Pro Ser Asp Thr Tyr Gly Ala Pro Gly Gly Gly Asn Gly Gly Arg
370                 375                 380

Pro Ser Asp Thr Tyr Gly Ala Pro Gly Gly Gly Asn Asn Gly Gly Arg
385                 390                 395                 400

Pro Ser Ser Ser Tyr Gly Ala Pro Gly Gly Gly Asn Gly Gly Arg Pro
                405                 410                 415

Ser Asp Thr Tyr Gly Ala Pro Gly Gly Gly Asn Gly Asn Gly Ser Gly
            420                 425                 430

Gly Arg Pro Ser Ser Ser Tyr Gly Ala Pro Gly Gln Gly Gln Gly Gly
            435                 440                 445

Phe Gly Gly Arg Pro Ser Asp Ser Tyr Gly Ala Pro Gly Gln Asn Gln
```

```
                    450                 455                 460
Lys Pro Ser Asp Ser Tyr Gly Ala Pro Gly Ser Gly Asn Gly Asn Gly
465                 470                 475                 480

Gly Arg Pro Ser Ser Tyr Gly Ala Pro Gly Ser Gly Pro Gly Gly
                485                 490                 495

Arg Pro Ser Asp Ser Tyr Gly Pro Pro Ala Ser Gly Ser Gly Ala Gly
                500                 505                 510

Gly Ala Gly Gly Ser Gly Pro Gly Gly Ala Asp Tyr Asp Asn Asp Glu
        515                 520                 525

<210> SEQ ID NO 19
<211> LENGTH: 324
<212> TYPE: PRT
<213> ORGANISM: Artificial sequence
<220> FEATURE:
<223> OTHER INFORMATION: Resilin exon 1

<400> SEQUENCE: 19

Gly Pro Glu Pro Pro Val Asn Ser Tyr Leu Pro Pro Ser Asp Ser Tyr
1               5                   10                  15

Gly Ala Pro Gly Gln Ser Gly Pro Gly Gly Arg Pro Ser Asp Ser Tyr
                20                  25                  30

Gly Ala Pro Gly Gly Gly Asn Gly Gly Arg Pro Ser Asp Ser Tyr Gly
            35                  40                  45

Ala Pro Gly Gln Gly Gln Gly Gln Gly Gln Gly Gly Gly Tyr Ala
        50                  55                  60

Gly Lys Pro Ser Asp Thr Tyr Gly Ala Pro Gly Gly Asn Gly Asn
65              70                  75                  80

Gly Gly Arg Pro Ser Ser Ser Tyr Gly Ala Pro Gly Gly Asn Gly
                85                  90                  95

Gly Arg Pro Ser Asp Thr Tyr Gly Ala Pro Gly Gly Asn Gly Gly
            100                 105                 110

Arg Pro Ser Asp Thr Tyr Gly Ala Pro Gly Gly Gly Asn Gly Asn
        115                 120                 125

Gly Gly Arg Pro Ser Ser Tyr Gly Ala Pro Gly Gln Gly Gln Gly
    130                 135                 140

Asn Gly Asn Gly Gly Arg Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
                165                 170                 175

Asn Gly Gly Arg Pro Ser Asp Thr Tyr Gly Ala Pro Gly Gly Gly Asn
            180                 185                 190

Asn Gly Gly Arg Pro Ser Ser Ser Tyr Gly Ala Pro Gly Gly Gly Asn
        195                 200                 205

Gly Gly Arg Pro Ser Asp Thr Tyr Gly Ala Pro Gly Gly Asn Gly
    210                 215                 220

Asn Gly Ser Gly Gly Arg Pro Ser Ser Tyr Gly Ala Pro Gly Gln
225                 230                 235                 240

Gly Gln Gly Gly Phe Gly Gly Arg Pro Ser Asp Ser Tyr Gly Ala Pro
                245                 250                 255

Gly Gln Asn Gln Lys Pro Ser Asp Ser Tyr Gly Ala Pro Gly Ser Gly
            260                 265                 270

Asn Gly Asn Gly Gly Arg Pro Ser Ser Ser Tyr Gly Ala Pro Gly Ser
        275                 280                 285

Gly Pro Gly Gly Arg Pro Ser Asp Ser Tyr Gly Pro Pro Ala Ser Gly
```

```
                    290                 295                 300
Ser Gly Ala Gly Gly Ala Gly Gly Ser Gly Pro Gly Gly Ala Asp Tyr
305                 310                 315                 320

Asp Asn Asp Glu
```

<210> SEQ ID NO 20
<211> LENGTH: 521
<212> TYPE: DNA
<213> ORGANISM: Artificial sequence
<220> FEATURE:
<223> OTHER INFORMATION: Cellulose binding domain DNA sequence

<400> SEQUENCE: 20

```
actcaattac accaataatc aaaattacta acacagctga cagtgattta aatttaaatg      60
acgtaaaagt tagatattat tacacaagtg atggtacaca aggacaaact ttctggggtg     120
atcatgctgg tgcattatta ggaaatagct atgttgataa cactggcaaa gtgacagcaa     180
acttcgttaa agaaacagca agcccaacat caacctatga tacatatgtt gaatttggat     240
ttgcaagcgg agcagctact cttaaaaaag acaatttat aactattcaa ggaagaataa     300
caaaatcaga ctggtcaaac tacgctcaga caatgactaa ttcatttgat gcaagtagtt     360
caacaccagt tgtaaatcca aaagttacag gatatatagg tggagctaaa gtacttggta     420
cagcaccagg tccagatgta ccatcttcaa taattaatcc tacttctgca catttgatc      480 cggagccacc agttaactcg tatctacctc cgtccgatag c                         521
```

<210> SEQ ID NO 21
<211> LENGTH: 180
<212> TYPE: PRT
<213> ORGANISM: Artificial sequence
<220> FEATURE:
<223> OTHER INFORMATION: Cellulose binding domain protein sequence

<400> SEQUENCE: 21

```
Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
                20                  25                  30

Ala Asp Ser Asp Leu Asn Leu Asn Asp Val Lys Val Arg Tyr Tyr Tyr
            35                  40                  45

Thr Ser Asp Gly Thr Gln Gly Gln Thr Phe Trp Gly Asp His Ala Gly
        50                  55                  60

Ala Leu Leu Gly Asn Ser Tyr Val Asp Asn Thr Gly Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
                100                 105                 110

Phe Ile Thr Ile Gln Gly Arg Ile Thr Lys Ser Asp Trp Ser Asn Tyr
            115                 120                 125

Ala Gln Thr Asn Asp Tyr Ser Phe Asp Ala Ser Ser Ser Thr Pro Val
        130                 135                 140

Val Asn Pro Lys Val Thr Gly Tyr Ile Gly Gly Ala Lys Val Leu Gly
145                 150                 155                 160

Thr Ala Pro Gly Pro Asp Val Pro Ser Ser Ile Ile Asn Pro Thr Ser
                165                 170                 175

Ala Thr Phe Asp
```

<210> SEQ ID NO 22
<211> LENGTH: 488
<212> TYPE: DNA
<213> ORGANISM: Artificial sequence
<220> FEATURE:
<223> OTHER INFORMATION: Cellulose binding domain DNA sequence

<400> SEQUENCE: 22

```
actcaattac accaataatc aaaattacta acacagctga cagtgattta aatttaaatg      60
acgtaaaagt tagatattat tacacaagtg atggtacaca aggacaaact ttctggggtg     120
atcatgctgg tgcattatta ggaaatagct atgttgataa cactggcaaa gtgacagcaa     180
acttcgttaa agaaacagca agcccaacat caacctatga tacatatgtt gaatttggat     240
ttgcaagcgg agcagctact cttaaaaaag gacaatttat aactattcaa ggaagaataa     300
caaaatcaga ctggtcaaac tacgctcaga caaatgacta ttcatttgat gcaagtagtt     360
caacaccagt tgtaaatcca aaagttacag gatatatagg tggagctaaa gtacttggta     420
cagcaccagg tccagatgta ccatcttcaa taattaatcc tacttctgca acatttgatc     480
cggagcca                                                             488
```

<210> SEQ ID NO 23
<211> LENGTH: 163
<212> TYPE: PRT
<213> ORGANISM: Artificial sequence
<220> FEATURE:
<223> OTHER INFORMATION: Cellulose binding domain protein sequence

<400> SEQUENCE: 23

```
Met Ala Ala Thr Ser Ser Met Ser Val Glu Phe Tyr Asn Ser Asn Lys
1               5                   10                  15

Ala Ala Gln Thr Asn Ser Ile Thr Pro Ile Ile Lys Ile Thr Asn Thr
            20                  25                  30

Ala Asp Ser Asp Leu Asn Leu Asn Asp Val Lys Val Arg Tyr Tyr Tyr
        35                  40                  45

Thr Ser Asp Gly Thr Gln Gly Gln Thr Phe Trp Gly Asp His Ala Gly
    50                  55                  60

Ala Leu Leu Gly Asn Ser Tyr Val Asp Asn Thr Gly Lys Val Thr Ala
65                  70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Ala Gln Thr Asn Asp Tyr Ser Phe Asp Ala Ser Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro
```

<210> SEQ ID NO 24
<211> LENGTH: 605
<212> TYPE: PRT
<213> ORGANISM: Drosophila melanogaster

<400> SEQUENCE: 24

-continued

```
Met Val Arg Pro Glu Pro Val Asn Ser Tyr Leu Pro Pro Ser Asp
1               5                   10                  15

Ser Tyr Gly Ala Pro Gly Gln Ser Gly Pro Gly Gly Arg Pro Ser Asp
            20                  25                  30

Ser Tyr Gly Ala Pro Gly Gly Asn Gly Gly Arg Pro Ser Asp Ser
            35                  40                  45

Tyr Gly Ala Pro Gly Gln Gly Gln Gln Gly Gln Gly Gln Gly Gly
        50                  55                  60

Tyr Ala Gly Lys Pro Ser Asp Thr Tyr Gly Ala Pro Gly Gly Gly Asn
65                  70                  75                  80

Gly Asn Gly Gly Arg Pro Ser Ser Tyr Gly Ala Pro Gly Gly Gly
                85                  90                  95

Asn Gly Gly Arg Pro Ser Asp Thr Tyr Gly Ala Pro Gly Gly Gly Asn
                100                 105                 110

Gly Gly Arg Pro Ser Asp Thr Tyr Gly Ala Pro Gly Gly Gly Asn
            115                 120                 125

Gly Asn Gly Gly Arg Pro Ser Ser Tyr Gly Ala Pro Gly Gln Gly
        130                 135                 140

Gln Gly Asn Gly Asn Gly Gly Arg Ser Ser Ser Tyr Gly Ala Pro
145                 150                 155                 160

Gly Gly Gly Asn Gly Gly Arg Pro Ser Asp Thr Tyr Gly Ala Pro Gly
                165                 170                 175

Gly Gly Asn Gly Gly Arg Pro Ser Asp Thr Tyr Gly Ala Pro Gly Gly
                180                 185                 190

Gly Asn Asn Gly Gly Arg Pro Ser Ser Tyr Gly Ala Pro Gly Gly
            195                 200                 205

Gly Asn Gly Gly Arg Pro Ser Asp Thr Tyr Gly Ala Pro Gly Gly Gly
    210                 215                 220

Asn Gly Asn Gly Ser Gly Gly Arg Pro Ser Ser Tyr Gly Ala Pro
225                 230                 235                 240

Gly Gln Gly Gln Gly Gly Phe Gly Gly Arg Pro Ser Asp Ser Tyr Gly
                245                 250                 255

Ala Pro Gly Gln Asn Gln Lys Pro Ser Asp Ser Tyr Gly Ala Pro Gly
            260                 265                 270

Ser Gly Asn Gly Asn Gly Gly Arg Pro Ser Ser Tyr Gly Ala Pro
            275                 280                 285

Gly Ser Gly Pro Gly Gly Arg Pro Ser Asp Ser Tyr Gly Pro Pro Ala
    290                 295                 300

Ser Gly Ser Gly Ala Gly Gly Ala Gly Gly Ser Gly Pro Gly Gly Ala
305                 310                 315                 320

Asp Tyr Asp Asn Asp Glu Pro Ala Lys Tyr Glu Phe Asn Tyr Gln Val
                325                 330                 335

Glu Asp Ala Pro Ser Gly Leu Ser Phe Gly His Ser Glu Met Arg Asp
            340                 345                 350

Gly Asp Phe Thr Thr Gly Gln Tyr Asn Val Leu Leu Pro Asp Gly Arg
            355                 360                 365

Lys Gln Ile Val Glu Tyr Glu Ala Asp Gln Gln Gly Tyr Arg Pro Gln
370                 375                 380

Ile Arg Tyr Glu Gly Asp Ala Asn Asp Gly Ser Gly Pro Ser Gly Pro
385                 390                 395                 400

Gly Gly Pro Gly Gly Gln Asn Leu Gly Ala Asp Gly Tyr Ser Ser Gly
            405                 410                 415
```

```
Arg Pro Gly Asn Gly Asn Gly Asn Gly Asn Gly Gly Tyr Ser Gly Gly
            420             425             430

Arg Pro Gly Gly Gln Asp Leu Gly Pro Ser Gly Tyr Ser Gly Gly Arg
            435             440             445

Pro Gly Gly Gln Asp Leu Gly Ala Gly Gly Tyr Ser Asn Gly Lys Pro
    450             455             460

Gly Gly Gln Asp Leu Gly Pro Gly Gly Tyr Ser Gly Gly Arg Pro Gly
465             470             475             480

Gly Gln Asp Leu Gly Arg Asp Gly Tyr Ser Gly Gly Arg Pro Gly Gly
                485             490             495

Gln Asp Leu Gly Ala Ser Gly Tyr Ser Asn Gly Arg Pro Gly Gly Asn
            500             505             510

Gly Asn Gly Gly Ser Asp Gly Gly Arg Val Ile Ile Gly Gly Arg Val
            515             520             525

Ile Gly Gly Gln Asp Gly Gly Asp Gln Gly Tyr Ser Gly Gly Arg Pro
        530             535             540

Gly Gly Gln Asp Leu Gly Arg Asp Gly Tyr Ser Ser Gly Arg Pro Gly
545             550             555             560

Gly Arg Pro Gly Gly Asn Gly Gln Asp Ser Gln Asp Gly Gln Gly Tyr
            565             570             575

Ser Ser Gly Arg Pro Gly Gln Gly Gly Arg Asn Gly Phe Gly Pro Gly
            580             585             590

Gly Gln Asn Gly Asp Asn Asp Gly Ser Gly Tyr Arg Tyr
            595             600             605
```